United States Patent
Tak et al.

(10) Patent No.: US 10,597,412 B2
(45) Date of Patent: Mar. 24, 2020

(54) EPOXY COMPOUND, MIXTURE, COMPOSITION, AND CURED PRODUCT COMPRISING SAME, METHOD FOR PREPARING SAME, AND USE THEREOF

(71) Applicant: KOREA INSTITUTE OF INDUSTRIAL TECHNOLOGY, Cheonan (KR)

(72) Inventors: Sang-Yong Tak, Busan (KR); Hyun-Aee Chun, Seongnam (KR); Yun-Ju Kim, Seoul (KR); Sung-Hwan Park, Gunpo (KR); Su-Jin Park, Ansan (KR); Sook-Yeon Park, Gunpo (KR); Hak-Jun Lee, Seoul (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 518 days.

(21) Appl. No.: 15/119,977

(22) PCT Filed: Feb. 17, 2015

(86) PCT No.: PCT/KR2015/001605
§ 371 (c)(1),
(2) Date: Aug. 18, 2016

(87) PCT Pub. No.: WO2015/126143
PCT Pub. Date: Aug. 27, 2015

(65) Prior Publication Data
US 2017/0066789 A1 Mar. 9, 2017

(30) Foreign Application Priority Data

Feb. 19, 2014 (KR) .................. 10-2014-0019179
Dec. 9, 2014 (KR) .................. 10-2014-0175937

(51) Int. Cl.
| | | |
|---|---|---|
| C08L 63/00 | (2006.01) | |
| C08G 59/30 | (2006.01) | |
| C08G 59/32 | (2006.01) | |
| C07D 303/12 | (2006.01) | |
| C07F 7/18 | (2006.01) | |

(52) U.S. Cl.
CPC .......... C07F 7/1804 (2013.01); C07D 303/12 (2013.01); C08G 59/306 (2013.01); C08G 59/3281 (2013.01); C08L 63/00 (2013.01)

(58) Field of Classification Search
CPC ..... C08L 63/00; C07D 303/02; C07D 303/12; C07D 407/12; C07F 7/18
See application file for complete search history.

(56) References Cited

U.S. PATENT DOCUMENTS

| | | | |
|---|---|---|---|
| 5,336,786 A | 8/1994 | Shiobara et al. | |
| 8,168,731 B2 | 5/2012 | Satou et al. | |
| 9,150,686 B2 * | 10/2015 | Chun ................. | C08K 7/14 |
| 9,670,309 B2 * | 6/2017 | Chun ................. | C07D 303/04 |
| 9,896,535 B2 * | 2/2018 | Chun ................. | C08K 7/14 |
| 9,902,803 B2 * | 2/2018 | Chun ................. | C08G 59/306 |
| 2014/0179836 A1 * | 6/2014 | Chun ................. | C08G 59/306 |
| | | | 523/466 |
| 2014/0308527 A1 | 10/2014 | Chun et al. | |
| 2015/0051316 A1 | 2/2015 | Chun et al. | |
| 2015/0105493 A1 | 4/2015 | Chun et al. | |
| 2015/0148452 A1 * | 5/2015 | Chun ................. | C07C 37/48 |
| | | | 523/458 |
| 2015/0203626 A1 | 7/2015 | Chun et al. | |
| 2015/0247033 A1 | 9/2015 | Chun et al. | |
| 2016/0229948 A1 * | 8/2016 | Chun ................. | C07F 7/1876 |

FOREIGN PATENT DOCUMENTS

| | | | | |
|---|---|---|---|---|
| JP | 06-345847 A | 12/1994 | | |
| JP | H11-343333 A | 12/1999 | | |
| JP | 2014-019736 A | 2/2014 | | |
| JP | 2015-502919 A | 1/2015 | | |
| KR | 10-2011-0043719 A | 4/2011 | | |
| KR | 10-2013-0111299 A | 10/2013 | | |
| KR | 10-2013-0112007 A | 10/2013 | | |
| KR | 10-2013-0135733 A | 12/2013 | | |
| KR | 10-2014-0009029 A | 1/2014 | | |
| KR | 10-2014-0036983 A | 3/2014 | | |
| WO | WO-2013028045 A2 * | 2/2013 | .............. | C08K 7/14 |
| WO | WO-2013137663 A1 * | 9/2013 | ........... | C08G 59/306 |
| WO | WO-2013180375 A1 * | 12/2013 | ............. | C07C 37/48 |
| WO | WO-2014007582 A1 * | 1/2014 | ........... | C07D 303/04 |

OTHER PUBLICATIONS

International Search Report for International Patent Application No. PCT/KR2015/001605 filed on Feb. 17, 2015.

* cited by examiner

*Primary Examiner* — Michael J Feely

(57) ABSTRACT

The present invention relates to a novel epoxy compound, a method for preparing same, a composition and cured product comprising same, and use thereof, wherein the compound shows excellent heat-resistant properties—specifically, a low thermal expansion property and a high glass transition temperature (including Tg-less which does not show a glass transition temperature), a flame retardant property and processability—specifically, a viscosity-control property, does not require a separate silane coupling agent, and has improved brittleness in a composite. According to one aspect of the present invention, provided are: an epoxy compound having at least one non-reactive silyl group, alkenyl group or combination thereof together with at least two epoxy groups and at least one alkoxysilyl group; a method for preparing the epoxy compound through alkoxysilylation and alkylsilylation; an epoxy composition comprising same; and a cured product.

17 Claims, 2 Drawing Sheets

EPOXY COMPOUND, MIXTURE, COMPOSITION, AND CURED PRODUCT COMPRISING SAME, METHOD FOR PREPARING SAME, AND USE THEREOF

CROSS-REFERENCE TO RELATED APPLICATIONS

The present specification is a U.S. National Stage of International Patent Application No. PCT/KR2015/001605 filed on Feb. 17, 2015, which claims priority to and the benefit of Korean Patent Application Nos. 10-2014-0019179 and 10-2014-0175937 filed in the Korean Intellectual Property Office on Feb. 19, 2014 and Dec. 9, 2014, respectively, the entire contents of which are incorporated herein by reference.

TECHNICAL FIELD

The present disclosure relates to a novel epoxy compound exhibiting the improved processability and/or brittleness as well as excellent heat-resistance when used in a composite obtained by the curing the composition including an epoxy compound and a filler (fibers and/or inorganic particles), a mixture, a composition and a cured product including the same, a production method thereof, and the use thereof. More particularly, in the composite described above, the present disclosure relates to a novel epoxy compound having excellent heat resistance, in detail, a low coefficient of thermal expansion and a high glass transition temperature (including Tg-less which does not exhibit a glass transition temperature), flame retardant property, and processability, specifically the controllable viscosity, not requiring a separate silane coupling agent, and having improved brittleness, a mixture, a composition and a cured product including the same, a production method thereof, and the use thereof.

BACKGROUND ART

Coefficient of thermal expansion of cured epoxy is higher several to tens times than those of ceramic materials and metals. Thus, in the case that an epoxy material is used in conjunction with an inorganic material or a metal, due to different coefficients of thermal expansion between the epoxy material and the inorganic material or between the epoxy material and the metal, the performance and processability of components are significantly limited. For example, in the case of semiconductor packaging or the like, when a silicon wafer and an epoxy substrate are adjacent to each other, due to a significant difference in coefficients of thermal expansion (CTE-mismatch) between constituent components during the processing and/or upon the change of temperatures, the defects, such as cracks, substrate warpage, peeling-off, substrate breakage, and the like, may occur.

Due to such a dimensional change arising from a high CTE of epoxy materials, the developments of next-generation semiconductor substrates, printed circuit boards (PCBs), packaging, organic thin film transistors (OTFT), flexible display substrates, and the like are restricted. Particularly, in the recent semiconductor and PCB industry, the design processing and reliability of next-generation components requiring high levels of integration, miniaturization, flexibility, high performance, and the like may be difficult due to epoxy with a significantly high CTE in comparison with metal/ceramic materials. In other words, in manufacturing components, defects may occur due to relatively high thermal expansion properties of polymer materials at processing temperatures for components, and furthermore, manufacturing processes may be limited. Further, achievements of a design, processability and reliability of components may be problematic. Accordingly, in order to assure the processibility and reliability of electronic components, an epoxy material having improved thermal expansion characteristics, for example, dimensional stability, is required.

To date, (1) the method of making an epoxy composite with inorganic particles (inorganic filler) and/or a fabric, or a (2) the method of designing a novel epoxy compound with a decreased CTE has been generally used, in order to decrease a coefficient of thermal expansion of cured epoxy products.

In the case that an epoxy compound makes composite with inorganic particles as a filler to improve thermal expansion characteristics, a large amount of inorganic silica particles with a diameter of about 2 μm-30 μm is required to reach the low CTE epoxy. However, a problem of the decreased processability and performance accompanies due to the addition of the a large amount of inorganic particles, In detail, a decrease in fluidity, the formation of voids when narrow gap is filled, and the like, due to a large amount of inorganic particles, may be problematic. In addition, the viscosity of a material may drastically increase due to the addition of inorganic particles. Furthermore, the size of inorganic particles tends to be reduced due to miniaturized semiconductor structures. However, in a case in which fillers with the diameter of 1 μm or less are used, the problem of increased viscosity may become much more severe. Further, in a case in which inorganic particles with a relatively large average diameter are used, the possibility that a composition including a resin and inorganic particles is not properly filled into applied component is increased. On the other hand, in a case in which a composition including an organic resin and a fiber as a filler is used, the CTE may be significantly reduced, but the CTE of composite is still higher as compared to a silicon chip or the like.

Due to the current limitations of composite technology of the aforementioned epoxy resin, the uses thereof in highly integrated, high-performance electronic components, such as next-generation semiconductors and PCBs, and the like, are limited. Therefore, the development of an epoxy composite with the improved thermal expansion properties, for example, a low CTE and high glass transition temperature is required to solve the problems, such as a high CTE in a current thermosetting polymer composite and insufficient heat resistance and processability caused by the high CTE of composite.

Thus, an epoxy compound having an alkoxysilyl group with the heat resistance, for example, a low coefficient of thermal expansion and a high glass transition temperature is disclosed in Korean Patent Application No. 2012-93320 and others, filed by the present inventor. However, when the epoxy compound is only composed of a very reactive alkoxysilyl group, the viscosity thereof may be rapidly increased during making a composite. Therefore, the development of an epoxy compound in which a rapid increase in viscosity during making a composite may be effectively controlled is required.

DISCLOSURE

Technical Problem

An aspect of the present disclosure may provide a novel epoxy compound exhibiting improved heat resistance in a composite and a mixture including the same.

An aspect of the present disclosure may provide a novel epoxy compound exhibiting excellent processability in a curing reaction and a mixture including the same.

An aspect of the present disclosure may provide a novel epoxy compound exhibiting improved brittleness in a composite and a mixture including the same.

An aspect of the present disclosure may provide a novel epoxy compound exhibiting excellent flame retardant property in a cured product and a mixture including the same.

An aspect of the present disclosure may provide a method of producing a novel epoxy compound exhibiting improved heat resistance in a composite.

An aspect of the present disclosure may provide a method of producing a novel epoxy compound having excellent processability in a curing reaction.

An aspect of the present disclosure may provide a method of producing a novel epoxy compound exhibiting improved brittleness properties in a composite.

An aspect of the present disclosure may provide a method of producing a novel epoxy compound exhibiting excellent flame retardant property in a cured product.

An aspect of the present disclosure may provide a composition (hereinafter, referred to as an "epoxy composition") containing a novel epoxy compound exhibiting improved heat resistance in a composite.

An aspect of the present disclosure may provide an epoxy composition having excellent processability in a curing reaction.

An aspect of the present disclosure may provide an epoxy composition exhibiting improved brittleness properties in a composite.

An aspect of the present disclosure may provide an epoxy composition having excellent flame retardant property in a cured product.

An aspect of the present disclosure may provide a cured product of the epoxy composition provided in the present disclosure.

An aspect of the present disclosure may provide the use of the epoxy composition provided in the present disclosure.

Technical Solution

According to a first aspect, there is provided an epoxy compound including, in a core, i) at least two epoxy groups selected from epoxy groups of the following Formulae E1 and E2; ii) at least one alkoxysilyl group selected from the group consisting of the following Formulae A1 to A5; and iii) at least one non-reactive silyl group, an alkenyl group, or a combination thereof, selected from the group consisting of the following Formulae A6 to A10.

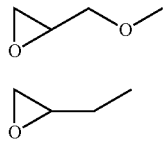
[Formula E1]

[Formula E2]

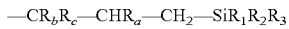
[Formula A1]

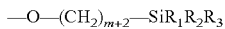
[Formula A2]

[Formula A3]

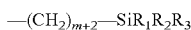
[Formula A4]

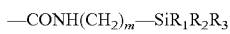
[Formula A5]

(In Formula A1, $R_a$, $R_b$ and $R_c$ are independently H or an alkyl group of 1 to 6 carbon atoms, and in the above Formulae A1 to A5, at least one of $R_1$ to $R_3$ is an alkoxy group of 1 to 6 carbon atoms, and the remainder are alkyl groups having 1 to 10 carbon atoms, wherein the alkyl groups and the alkoxy group may be linear or branched, may be cyclic or acyclic, and may or may not have an N, O, S, or P heteroatom, and m is an integer of 1 to 10.)

[Formula A6]

[Formula A7]

[Formula A8]

[Formula A9]

[Formula A10]

(In the above Formula A6, $R_a$, $R_b$ and $R_c$ are independently H or an alkyl group of 1 to 6 carbon atoms, and in the above Formulae A6 to A10, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom, and m is an integer of 1 to 10.)

According to a second aspect, in the first aspect, the alkenyl group may be selected from the group consisting of the following Formulae A11 to A13.

[Formula A11]

[Formula A12]

[Formula A13]

(In Formula A11, $R_a$, $R_b$ and $R_c$ are independently H or an alkyl group of 1 to 6 carbon atoms, wherein the alkyl group may be a linear or branched, may be cyclic or acyclic, and may or may not have an N, O, S, or P heteroatom, and m in Formulae A12 and A13 is an integer of 1 to 10.)

According to a third aspect, in the first aspect, the core may be selected from the group consisting of the following Formula AC to OC.

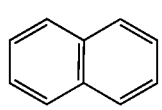
(AC)

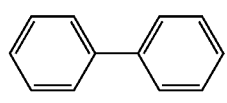
(BC)

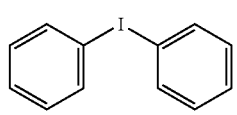
(CC)

(DC)

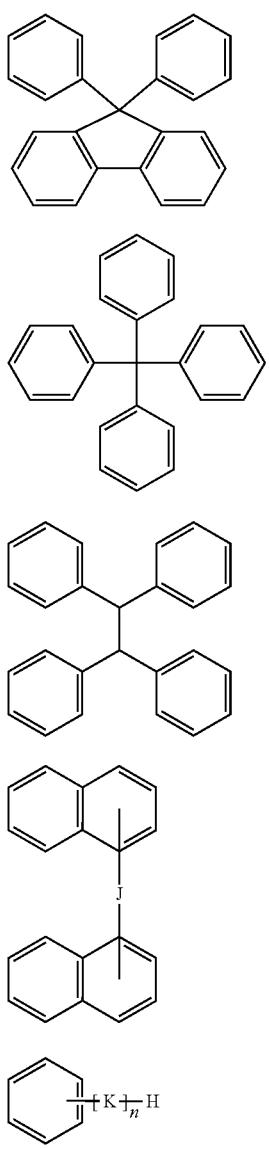
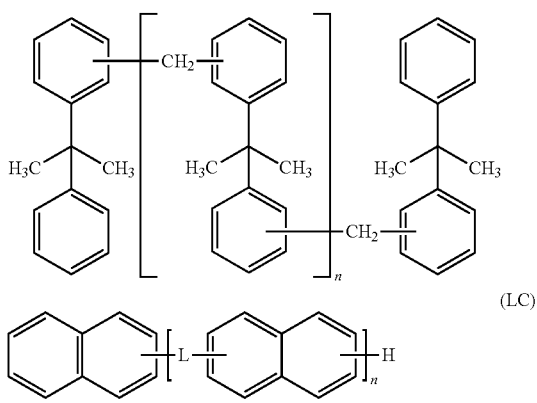
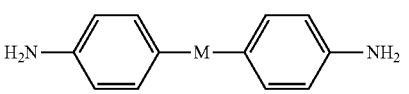
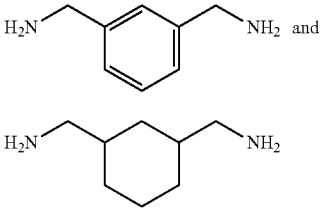
(In the above Formula DC, I is —CH$_2$—, —C(CH$_3$)$_2$-, —C(CF$_3$)$_2$-, —S—, —SO$_2$—,
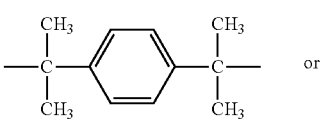 or
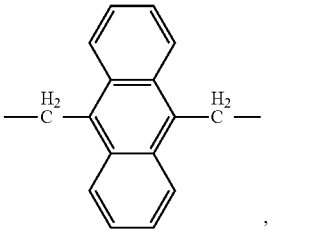
in the above Formula HC, J is a direct linkage, —CH$_2$—, or
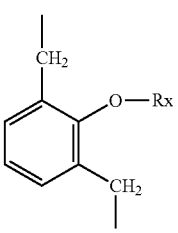
(Rx is H or a C$_1$-C$_3$ alkyl group),
in the above Formula IC, K is one of the group consisting of the following Formulae 1ac to 1fc,
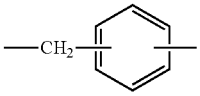
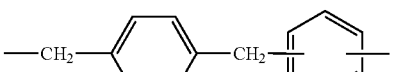
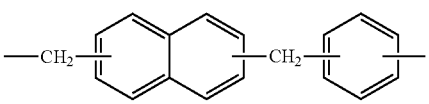

-continued

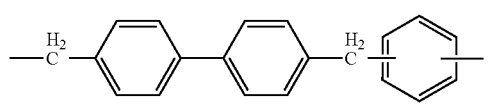
1dc

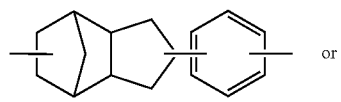
1ec

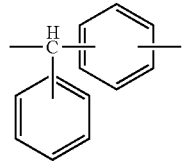
1fc in the above Formula LC, L is

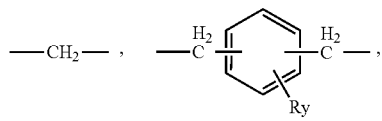

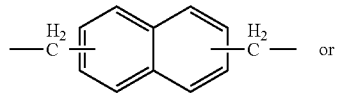

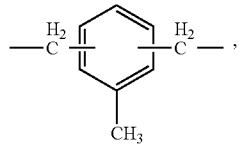

in

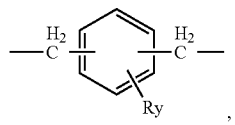,

Ry is a linear or branched C1-C10 alkyl group, in the above Formula MC, M is $CH_2-$, $-C(CH_3)_2-$, $-C(CF_3)_2-$, $-S-$, $-SO_2-$, or

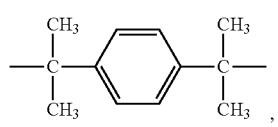

and R is H or $C_1$-$C_3$ alkyl,
in the above Formula IC, when K is 1ac to 1ec, n is an integer of 3 or more, and when K is 1fc, n is an integer of 2 or more,
in the above Formula JC, n is an integer of 2 or more,
in the above Formula KC, n is an integer of 0 or more, in the above Formula LC, when L is

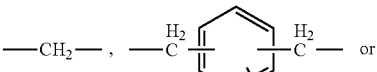 or

, n is an integer of 3 or more, and
when L is

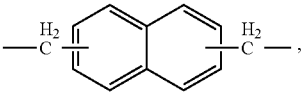, n is an integer of 2 or more,

According to a fourth aspect, in the third aspect, when the same type of cores selected from the above Formulae AC to HC and Formulae MC to OC are two or more, a core of the above Formulae AC to HC may be connected by the following linking group LG1, and a core of the above Formulae MC to OC may be connected by the following linking group LG2.

[Formula LG1]

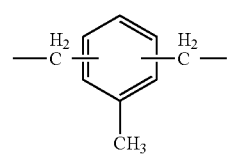

[Formula LG2]

According to a fifth aspect, in the first aspect, the epoxy compound may be represented by any one of the following Formulae AF to OF.

(AF)
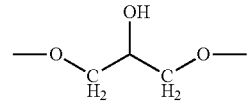

(BF)
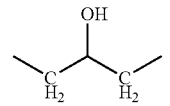

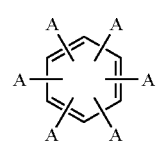

(CF)
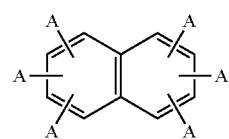

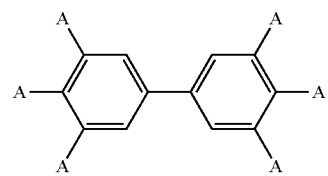

-continued (DF) 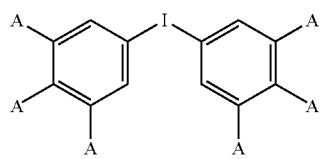

(EF) 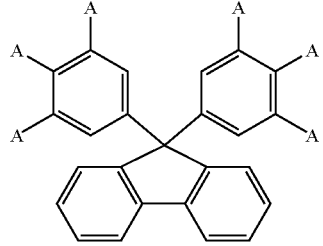

(FF) 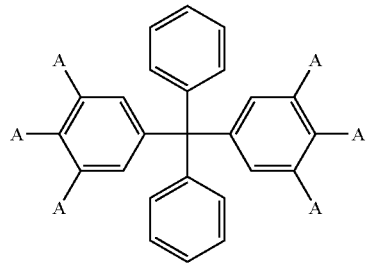

(GF) 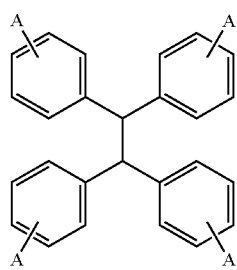

(HF) 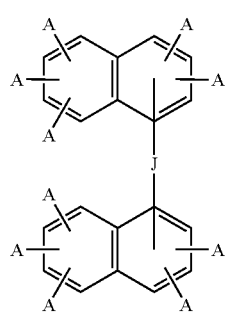

(IF) 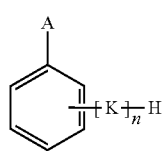

(JF) 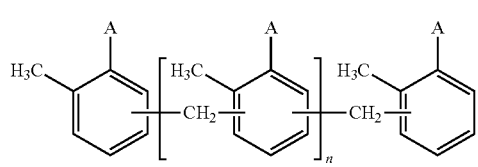

-continued (KF) 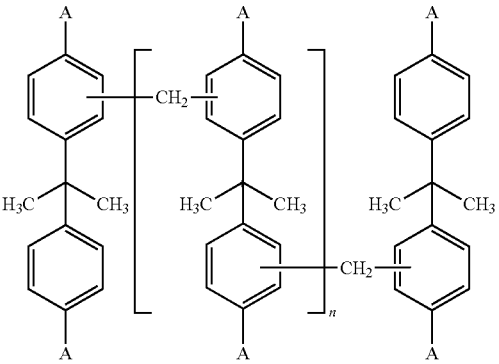

(LF) 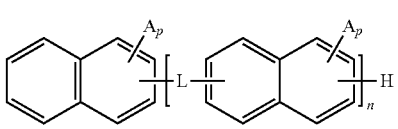

(MF) 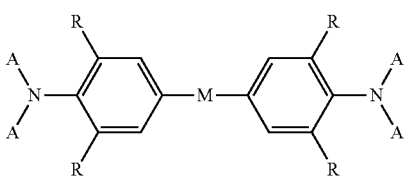

(NF) 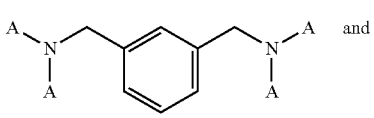 and (OF) 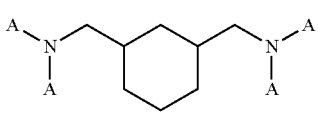

(At least two of substituents A of the above Formulae AF to FF may be selected from the following Formulae E1 and E2, at least one of substituents A thereof may be selected from the group consisting of the following Formulae A1 to A3, and the remainder thereof may be independently selected from the group consisting of the above Formulae A6 to A8, Formula A11, Formula A12, and hydrogen, at least two of substituents A of the above Formulae GF to LF may be represented by the following Formula E1, at least one of substituents A thereof may be represented by the following Formula A2 or Formula A3, and the remainder thereof may be independently selected from the group consisting of the following Formula A7, the following Formula A8, the following Formula A12, and hydrogen, and at least two of substituents A of the above Formulae MF to OF may be represented by the following Formula E2, at least one of substituents A thereof may be selected from the following Formulae A4 and A5, and the remainder thereof may be independently selected from the group consisting of the following Formula A9, the following Formula A10, the following Formula A13, and hydrogen, in the above Formula DF, I is —$CH_2$—, —$C(CH_3)_2$—, —$C(CF_3)_2$—, —S—, —$SO_2$—,

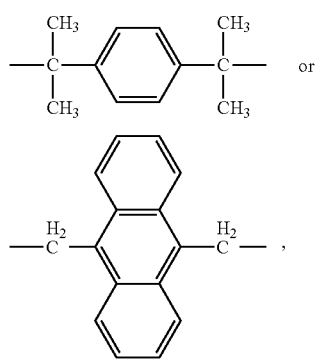 or

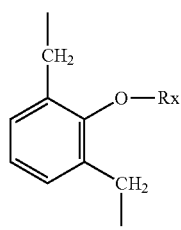, in the above Formula HF, J is a direct linkage, —CH$_2$—, or

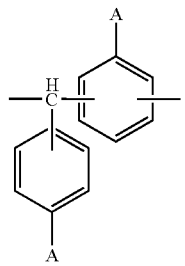

(Rx is H or a C$_1$-C$_3$ alkyl group), in the above Formula IF, K is one of the group consisting of the following formulae 1A to 1F,

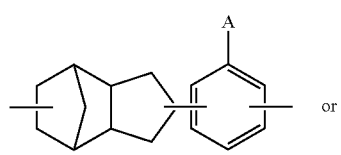

-continued

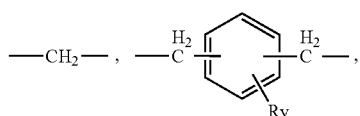

in the above Formula LF, L is

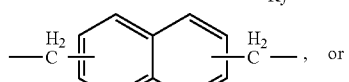

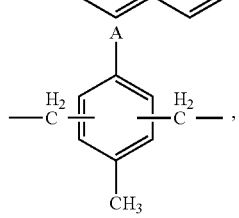

and in

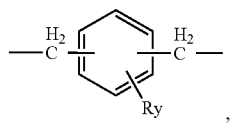

Ry is a linear or branched C1-C10 alkyl group, in the above Formula MF, M is —CH$_2$—, —C(CH$_3$)$_2$—, —C(CF$_3$)$_2$—, —S—, —SO$_2$—, or

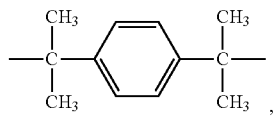

and R is H or C$_1$-C$_3$ alkyl, in the above Formula IF, when K is 1A to 1E, n is an integer of 3 or more,
when K is 1F, n is an integer of 2 or more,
In the above Formula JF, n is an integer of 2 or more,
in the above Formula KF, n is an integer of 0 or more,
in the above Formula LF, when L is

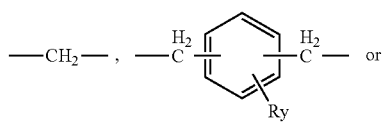

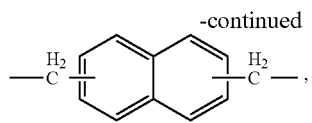

n is an integer of 3 or more, and when L is

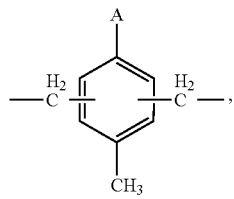

n is an integer of 2 or more, and in the above Formula LF, p is 1 or 2.

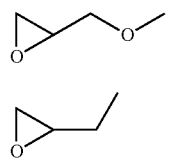 [Formula E1]

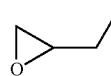 [Formula E2]

—$CR_bR_c$—$CHR_a$—$CH_2$—$SiR_1R_2R_3$ [Formula A1]

—O—$(CH_2)_{m+2}$—$SiR_1R_2R_3$ [Formula A2]

—O—$CONH(CH_2)_m$—$SiR_1R_2R_3$ [Formula A3]

—$(CH_2)_{m+2}$—$SiR_1R_2R_3$ [Formula A4]

—$CONH(CH_2)_m$—$SiR_1R_2R_3$ [Formula A5]

(In Formula A1, $R_a$, $R_b$ and $R_c$ are independently H or an alkyl group of 1 to 6 carbon atoms, and in the above Formulae A1 to A5, at least one of $R_1$ to $R_3$ is an alkoxy group of 1 to 6 carbon atoms, and the remainder are alkyl groups having 1 to 10 carbon atoms, wherein the alkyl groups and the alkoxy group may be linear or branched, may be cyclic or acyclic, and may or may not have an N, O, S, or P heteroatom, and m is an integer of 1 to 10.)

—$CR_bR_c$—$CHR_a$—$CH_2$—$SiR_4R_5R_6$ [Formula A6]

—O—$(CH_2)_{m+2}$—$SiR_4R_5R_6$ [Formula A7]

—O—$CONH(CH_2)_m$—$SiR_4R_5R_6$ [Formula A8]

—$(CH_2)_{m+2}$—$SiR_4R_5R_6$ [Formula A9]

—$CONH(CH_2)_m$—$SiR_4R_5R_6$ [Formula A10]

(In the above Formula A6, $R_a$, $R_b$ and $R_c$ are independently H or an alkyl group of 1 to 6 carbon atoms, and in the above Formulae A6 to A10, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom, and m is an integer of 1 to 10.)

—$CR_bR_c$—$CR_a$=$CH_2$ [Formula A11]

—O—$(CH_2)_m$—CH=$CH_2$ [Formula A12]

—$(CH_2)_m$—CH=$CH_2$ [Formula A13]

(In Formula A11, $R_a$, $R_b$ and $R_c$ are independently H or an alkyl group of 1 to 6 carbon atoms, wherein the alkyl group may be a linear or a branched, may be cyclic or acyclic, and may or may not have an N, O, S or P heteroatom, and in Formula A12 and Formula A13, m is an integer of 1 to 10).

According to a sixth aspect, in the first aspect, the epoxy compound may include, in a core, i) at least two epoxy groups represented by the following Formula E1

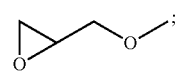 [Formula E1]

ii) at least one alkoxysilyl group represented by the following Formula A1

—$CR_bR_c$—$CHR_a$—$CH_2$—$SiR_1R_2R_3$ [Formula A1]

(In Formula A1, $R_a$, $R_b$ and $R_c$ are independently H or an alkyl group of 1 to 6 carbon atoms, at least one of $R_1$ to $R_3$ is an alkoxy group of 1 to 6 carbon atoms, and the remainder thereof are alkyl groups having 1 to 10 carbon atoms, wherein the alkyl groups and the alkoxy group may be linear or branched, may be cyclic or acyclic, and may or may not have an N, O, S, or P heteroatom, and m is an integer of 1 to 10); and iii) at least one alkenyl group represented by the following Formula A11

—$CR_bR_c$—$CR_a$=$CH_2$ [Formula A11]

(In Formula A11, $R_a$, $R_b$ and $R_c$ are independently H or an alkyl group of 1 to 6 carbon atoms, wherein the alkyl group may be a linear or a branched, may be cyclic or acyclic, and may or may not have an N, O, S or P heteroatom.)

According to a seventh aspect, in the first aspect, at least one of $R_1$ to $R_3$ in the alkoxysilyl group represented by the above Formulae A1 to A5 may be an alkoxy group of 2 to 4 carbon atoms.

According to an eighth aspect, in the first aspect, $R_1$ to $R_3$ in the alkoxysilyl group represented by the above Formulae A1 to A5 may be ethoxy groups.

According to a ninth aspect, when in the first aspect, all of $R_1$ to $R_3$ in the alkoxysilyl group represented by the above Formulae A1 to A5 are methoxy groups, the epoxy compound may include at least one alkenyl group.

According to a tenth aspect, there is provided a mixture of an epoxy compound, including the epoxy compound of any one of the first to ninth aspects, wherein when the epoxy compound includes a non-reactive silyl group, a ratio of the alkoxysilyl group to the non-reactive silyl group is 1:99 to 99:1.

According to an eleventh aspect, there is provided a method of producing an epoxy compound of any one of the following Formulae AF to OF, including the reaction of a starting material of any one of the following Formulae AS1 to OS1 and alkoxysilane of the following Formula AS5, or the reaction of the starting material, alkoxysilane of the following Formula AS5, and non-reactive silane of the following Formula AS6, in the presence of a platinum catalyst and an optional solvent.

$HSiR_1R_2R_3$ [Formula AS5]

(In the above Formula AS5, at least one of $R_1$ to $R_3$ is a C1-C6 alkoxy group, in detail, an ethoxy group, and the remainder thereof are C1-C10 alkyl groups, wherein the alkoxy group and the alkyl groups may be linear or branched, may be cyclic or acyclic, and may or may not have an N, O, S, or P heteroatom.)

HSiR4R5R6 [Formula AS6]

(In the above Formula AS6, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom.)

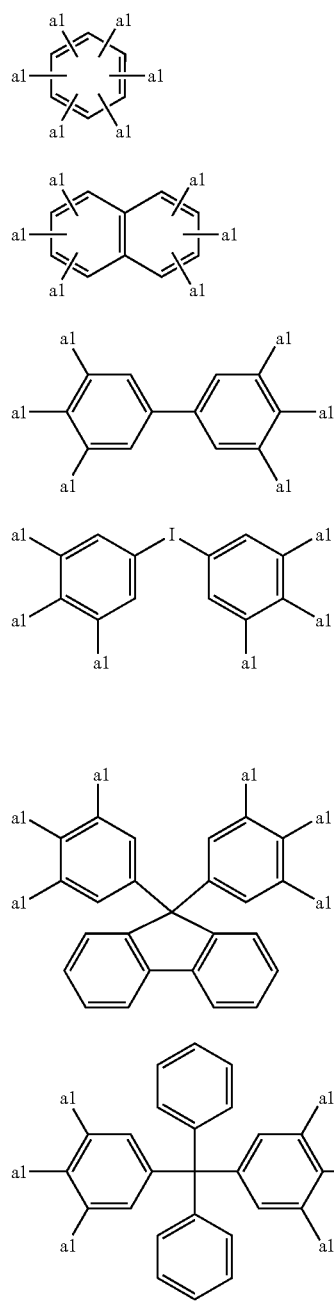

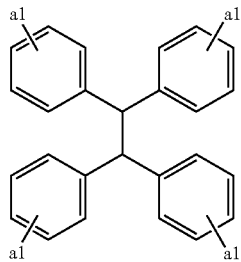

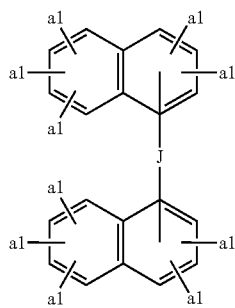

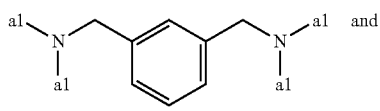  (NS1)

and

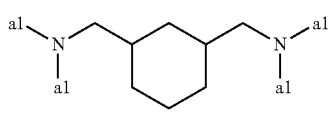  (OS1)

(At least two of a plurality of substituents a1 of the above Formulae AS1 to FS1 may be represented by the following Formula E1 or E2, at least two of the plurality of substituents a1 may be represented by the following Formula A11 or A12, and the remainder thereof may be hydrogen, at least two of substituents a1 of the above Formulae GS1 to LS1 may be represented by the following Formula E1, at least two of the substituents a1 may be represented by the following Formula A12, and the remainder thereof may be hydrogen, at least two of substituents a1 of the above Formulae MS1 to OS1 may be represented by the above Formula E2, and the remainder thereof may be represented by the above Formula A13, in the above Formula DS1, I is $-CH_2-$, $-C(CH_3)_2-$, $-C(CF_3)_2-$, $-S-$, $-SO_2-$,

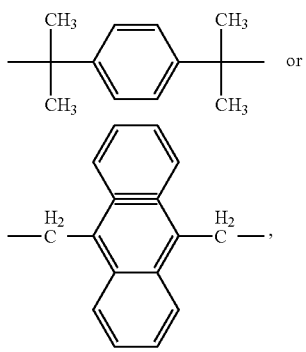

in the above Formula HS1, J is a direct linkage, $-CH_2-$, or

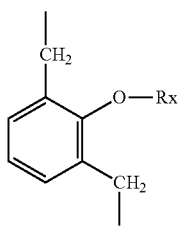

(Rx is H or a $C_1$-$C_3$ alkyl group), in the above Formula IS1, K is one of the group consisting of the following Formulae 1a1 to 1f1,

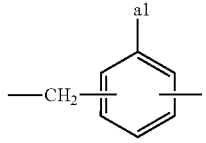  1a1

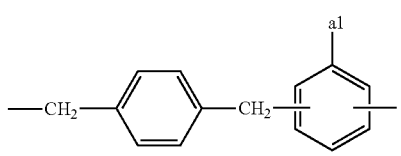  1b1

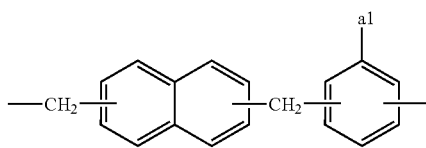  1c1

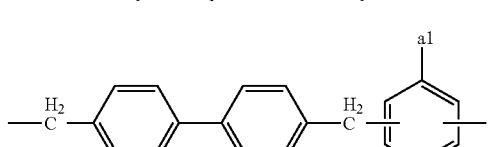  1d1

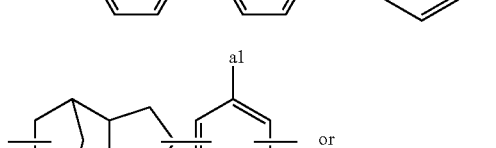  1e1 or

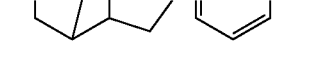  1f1 in the above Formula LS1, L is

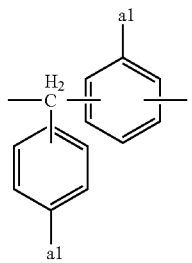

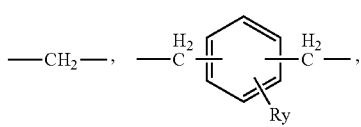  or

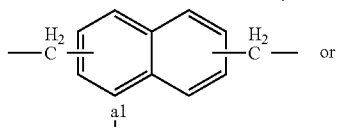

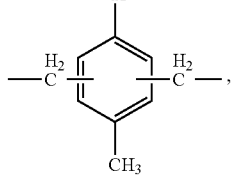

and in

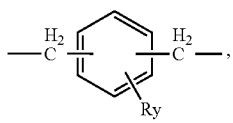

Ry is a linear or branched C1-C10 alkyl group,
in the above Formula MS1, M is —CH$_2$—, —C(CH$_3$)$_2$—, —C(CF$_3$)$_2$—, —S—, —SO$_2$—, or

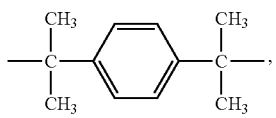

and R is H or C$_1$-C$_3$ alkyl,
in the above Formula IS1, when K is 1a1 to 1e1, n is an integer of 3 or more,
when K is 1f1, n is an integer of 2 or more,
in the above Formula JS1, n is an integer of 2 or more,
in the above Formula KS1, n is an integer of 0 or more,
in the above Formula LS1, when L is

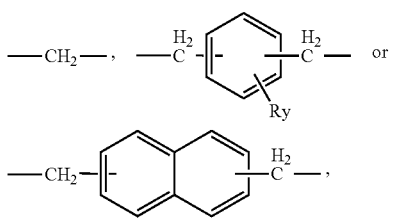

n is an integer of 3 or more, and
when L is

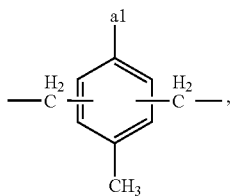

n is an integer of 2 or more,
in the above Formula LS1, p is 1 or 2.

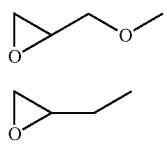  [Formula E1]

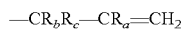  [Formula E2]

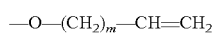  —CR$_b$R$_c$—CR$_a$=CH$_2$  [Formula A11]

—O—(CH$_2$)$_m$—CH=CH$_2$  [Formula A12]

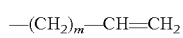  —(CH$_2$)$_m$—CH=CH$_2$  [Formula A13]

(In Formula A11, R$_a$, R$_b$ and R$_c$ are independently H or an alkyl group of 1 to 6 carbon atoms, wherein the alkyl group may be a linear or a branched, may be cyclic or acyclic, and may or may not have an N, O, S or P heteroatom, and in Formulae A12 and A13, m is an integer of 1 to 10).

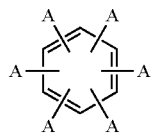 (AF)

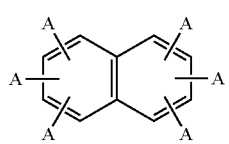 (BF)

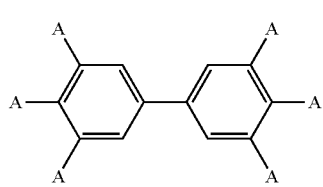 (CF)

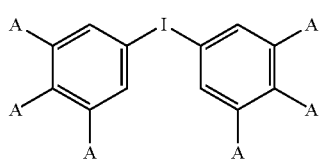 (DF)

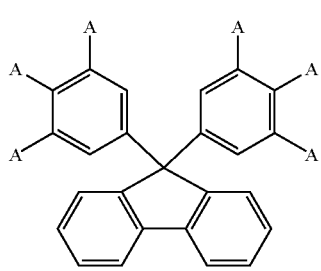 (EF)

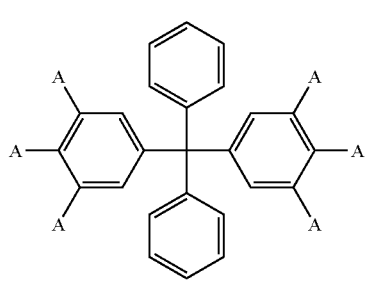 (FF)

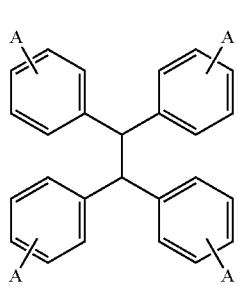 (GF)

-continued

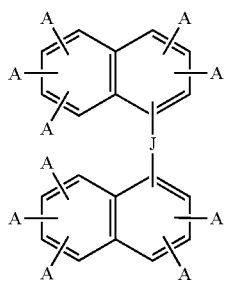 (HF)

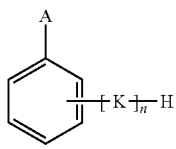 (IF)

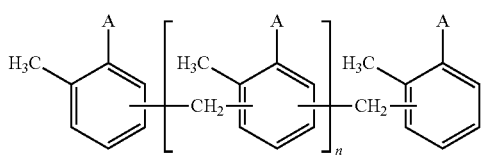 (JF)

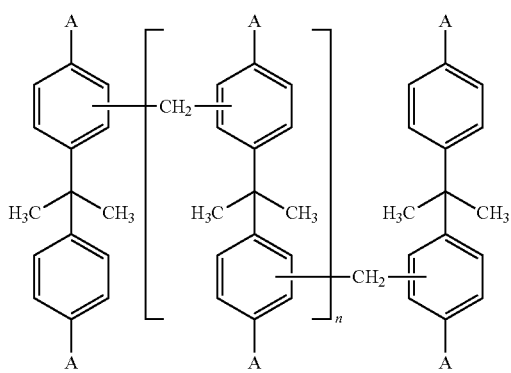 (KF)

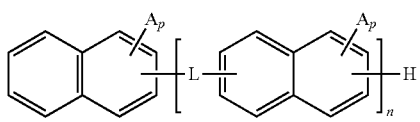 (LF)

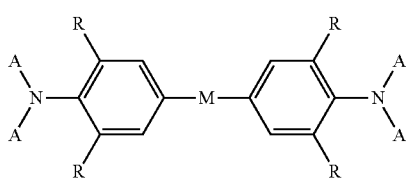 (MF)

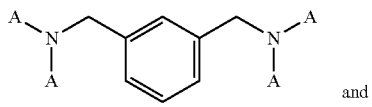 (NF)

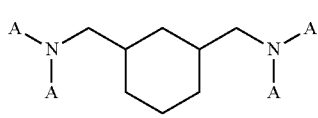 and (OF)

(At least two of substituents A of the above Formulae AF to FF may be represented by the above Formula E1 or E2, at least one of substituents A thereof may be selected from the group consisting of the following Formulae A1 and A2, and the remainder thereof may be independently selected from the group consisting of the following Formulae A6, A7, A11, A12 and hydrogen, at least two of substituents A of the above Formulae GF to LF may be represented by the following Formula E1, at least one of substituents A thereof may be represented by the following Formula A2, and the remainder thereof may be independently selected from the group consisting of the following Formulae A7 and A12, and hydrogen, at least two of substituents A of the above Formulae MF to OF may be represented by the following Formula E2, at least one of substituents A thereof may be represented by the following Formula A4, and the remainder thereof may be independently selected from the group consisting of the following Formulae A9 and A13, and hydrogen, in the above Formula DF, I is —CH$_2$—, —C(CH$_3$)$_2$—, —C(CF$_3$)$_2$—, —S—, —SO$_2$—,

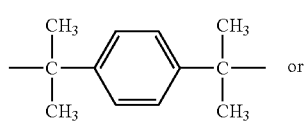 or

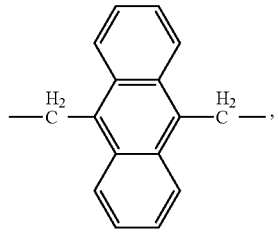

and in the above Formula HF, J is a direct linkage, —CH$_2$—, or

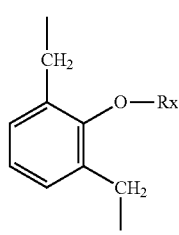

(Rx is H or a C$_1$-C$_3$ alkyl group),
in the above Formula IF, K is one of the group consisting of the following formulae 1A to 1F,

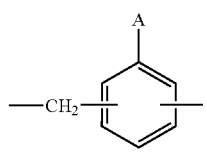 1A

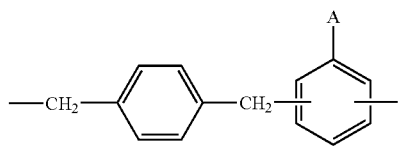 1B

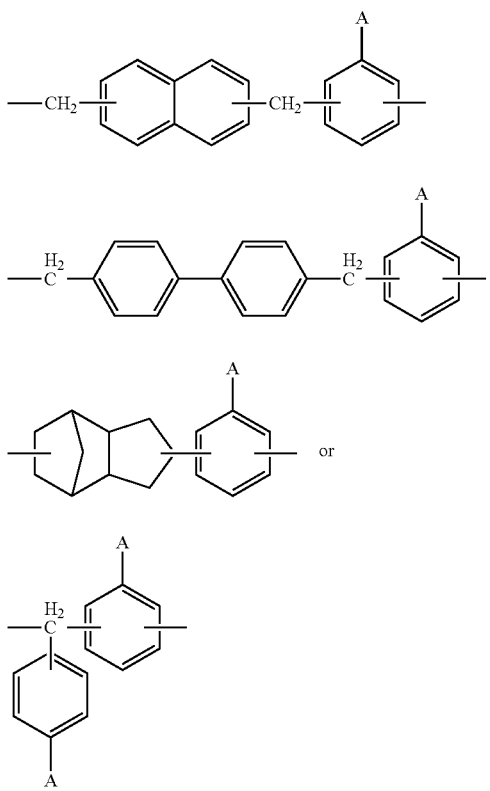

In the above Formula LF, L is

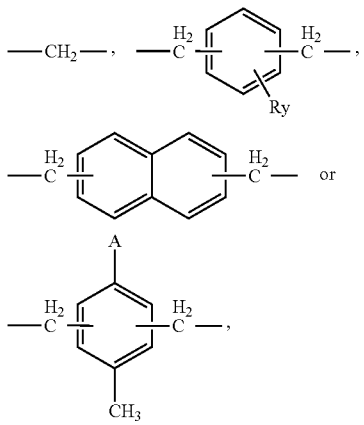

and in

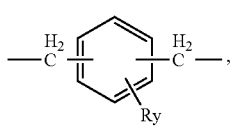

Ry is a linear or branched C1-C10 alkyl group,
in the above Formula MF, M is —CH$_2$—, —C(CH$_3$)$_2$—, —C(CF$_3$)$_2$—, —S—, —SO$_2$—, or

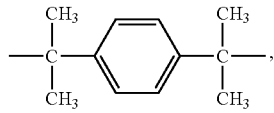

and R is H or C$_1$-C$_3$ alkyl,
in the above Formula IF, when K is 1A to 1E, n is an integer of 3 or more,
when K is 1F, n is an integer of 2 or more,
in the above Formula JF, n is an integer of 2 or more,
in the above Formula KF, n is an integer of 0 or more,
in the above Formula LF, when L is

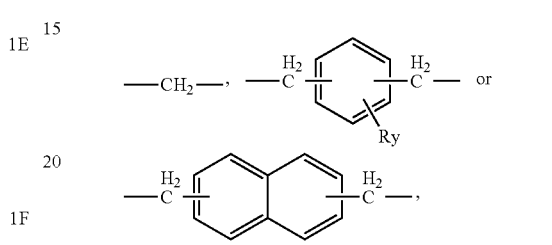

n is an integer of 3 or more, and
when L is

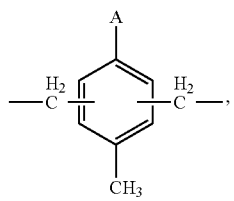

n is an integer of 2 or more, and
in the above Formula LF, p is 1 or 2.

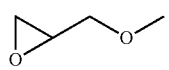 [Formula E1]

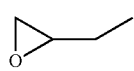 [Formula E2]

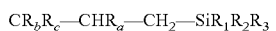 [Formula A1]

 [Formula A2]

 [Formula A4]

(In Formula A1, R$_a$, R$_b$ and R$_c$ are independently H or an alkyl group of 1 to 6 carbon atoms, and in the above Formulae A1, A2, and A4, at least one of R$_1$ to R$_3$ is an alkoxy group of 1 to 6 carbon atoms, and the remainder are alkyl groups having 1 to 10 carbon atoms, wherein the alkyl groups and the alkoxy group may be linear or branched, may be cyclic or acyclic, and may or may not have an N, O, S, or P heteroatom, and m is an integer of 1 to 10.)

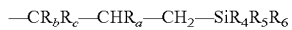 [Formula A6]

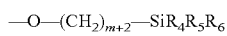 [Formula A7]

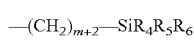 [Formula A9]

(In the above Formula A6, $R_a$, $R_b$ and $R_c$ are independently H or an alkyl group of 1 to 6 carbon atoms, and in the above Formulae A6, A7 and A9, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom, and m is an integer of 1 to 10.)

—$CR_bR_c$—$CR_a$=$CH_2$  [Formula A11]

—O—$(CH_2)_m$—CH=$CH_2$  [Formula A12]

—$(CH_2)_m$—CH=$CH_2$  [Formula A13]

(In Formula A11, $R_a$, $R_b$ and $R_c$ are independently H or an alkyl group of 1 to 6 carbon atoms, wherein the alkyl group may be a linear or a branched, may be cyclic or acyclic, and may or may not have an N, O, S or P heteroatom, and in Formulae A12 and A13, m is an integer of 1 to 10).

According to a twelfth aspect, in the eleventh aspect, there is provided the method of producing an epoxy compound, in which the starting material and alkoxysilane of the above Formula AS5 react with each other, such that the alkoxysilane of the above Formula AS5 with respect to 1 equivalent of an alkenyl group of the starting material may be within a range of 0.1 equivalent to 5 equivalents.

According to a thirteenth aspect, in the eleventh aspect, there is provided the method of producing an epoxy compound, in which when all of $R_1$ to $R_3$ of the alkoxysilane of the above Formula AS5 are methoxy, the starting material and alkoxysilane of the above Formula AS5 react with each other, such that the alkoxysilane of the above Formula AS5 with respect to 1 equivalent of an alkenyl group of the starting material may be within a range of 0.1 equivalent or more and less than 1 equivalent.

According to a fourteenth aspect, in the first aspect, there is provided the method of producing an epoxy compound of any one of the following Formulae AF to OF, including the reaction of a starting material of any one of the above Formulae AS2 to OS2 and alkoxysilane of the following Formula AS3, or the reaction of the starting material, alkoxysilane of the following Formula AS3, and non-reactive silane of the following Formula AS4, in the presence of an optional solvent.

OCN—$(CH_2)_m$—$SiR_1R_2R_3$  [Formula AS3]

(In the above Formula AS3, at least one of $R_1$ to $R_3$ is a C1-C6 alkoxy group, in detail, an ethoxy group, and the remainder thereof are C1-C10 alkyl groups, wherein the alkoxy group and the alkyl groups may be linear or branched, may be cyclic or acyclic, and may or may not have an N, O, S, or P heteroatom. m is an integer of 1 to 10, in detail, an integer of 3 to 6.)

OCN—$(CH_2)_m$—$SiR_4R_5R_6$  [Formula AS4]

(In the above Formula AS4, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom, and m is integers of 1 to 10, in detail, integers of 3 to 6.)

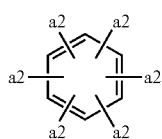
(AS2)

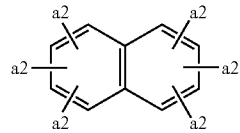
(BS2)

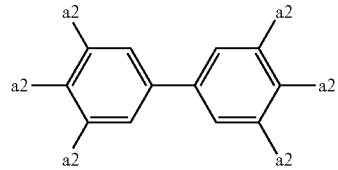
(CS2)

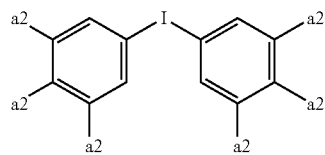
(DS2)

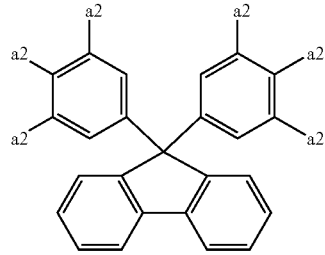
(ES2)

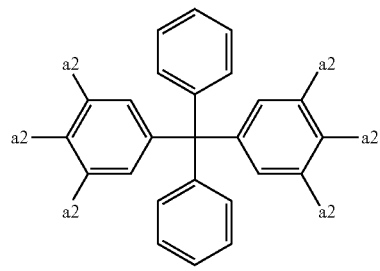
(FS2)

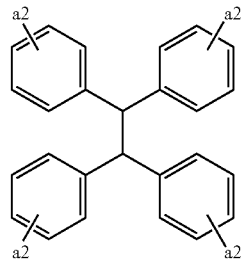
(GS2)

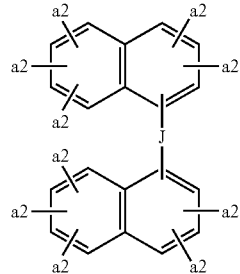
(HS2)

-continued (IS2)
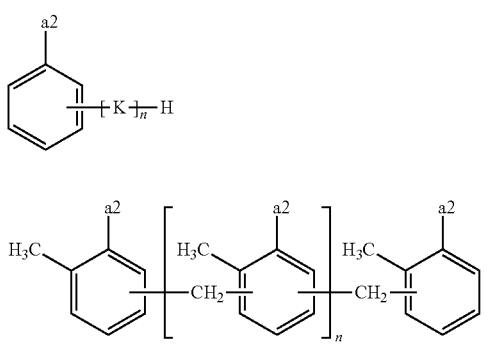

(JS2)

(KS2)

(LS2)

(MS2)

(NS2)

and (OS2)

(At least two of substituents a2 of the above Formulae AS2 to FS2 may be represented by the following Formula E2, at least two of the substituents a2 may be hydroxy groups, and the remainder thereof may be independently selected from the group consisting of hydrogen and the following Formula A11, at least two of substituents a2 of the above Formulae GS2 to LS2 may be represented by the above Formula E1, at least two of the substituents a2 may be hydroxy groups, and the remainder thereof may be hydrogen, at least two of substituents a2 of the above Formulae MS2 to OS2 may be represented by the above Formula E2, and the remainder thereof may be hydrogen, in the above Formula DS2, I is —CH$_2$—, —C(CH$_3$)$_2$—, —C(CF$_3$)$_2$—, —S—, —SO$_2$,

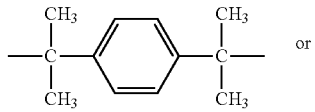 or

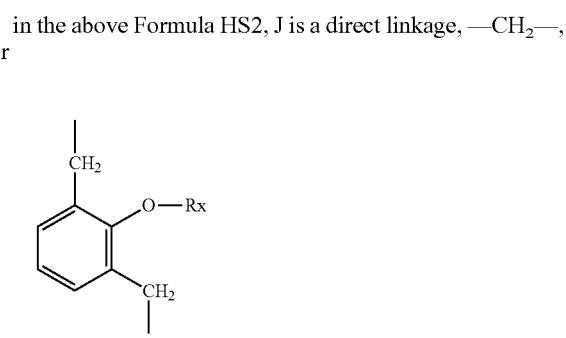

in the above Formula HS2, J is a direct linkage, —CH$_2$—, or

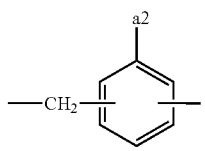

(Rx is H or a C$_1$-C$_3$ alkyl group), in the above Formula IS2, K is one of the group consisting of the following Formulae 1a2 to 1f2, 1a2
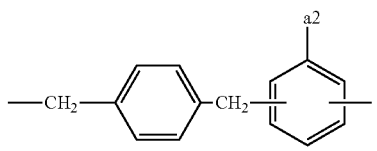

1b2
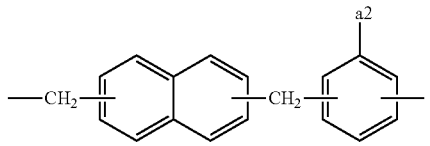

1c2
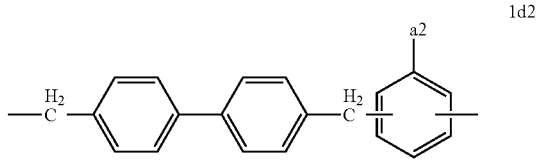

1d2
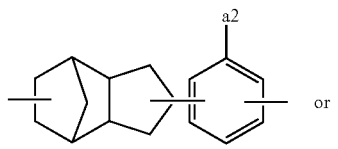

1e2

-continued

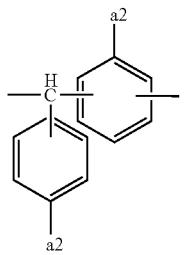

in the above Formula LS2, L is

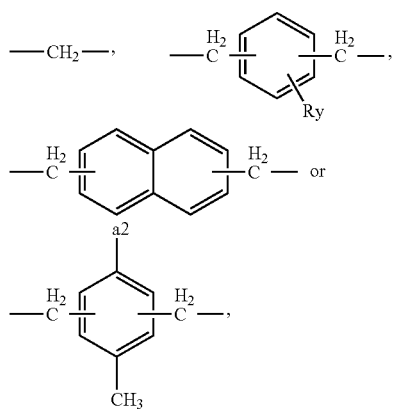

in

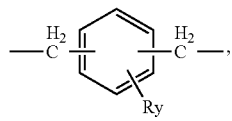

Ry is a linear or branched C1-C10 alkyl group,
in the above Formula MS2, M is —CH$_2$—, —C(CH$_3$)$_2$—, —C(CF$_3$)$_2$—, —S—, —SO$_2$—, or

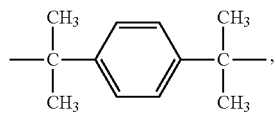

and, R is H or C$_1$-C$_3$ alkyl,
in the above Formula IS2, when K is 2a to 2e, n is an integer of 3 or more,
when K is 2f, n is an integer of 2 or more,
in the above Formula JS2, n is an integer of 2 or more,
in the above Formula KS2, n is an integer of 0 or more,
in the above Formula LS2, when L is

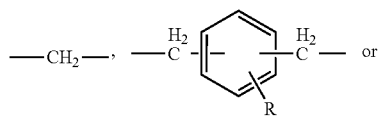

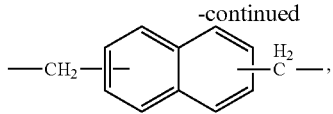

n is an integer of 3 or more,
and
when L is

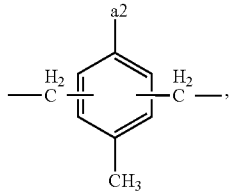

n is an integer of 2 or more, and
in the above Formula LS2, p is 1 or 2.)

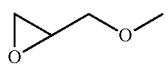 [Formula E1]

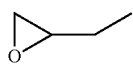 [Formula E2]

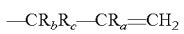 [Formula A11]

(In Formula A11, R$_a$, R$_b$ and R$_c$ are independently H or an alkyl group of 1 to 6 carbon atoms, wherein the alkyl group may be a linear or a branched, may be cyclic or acyclic, and may or may not have an N, O, S or P heteroatom.)

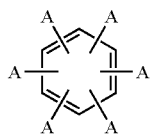 (AF)

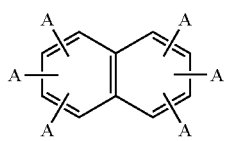 (BF)

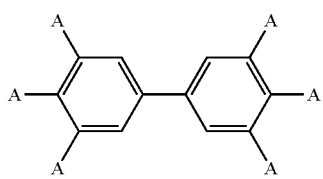 (CF)

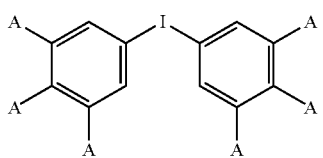 (DF)

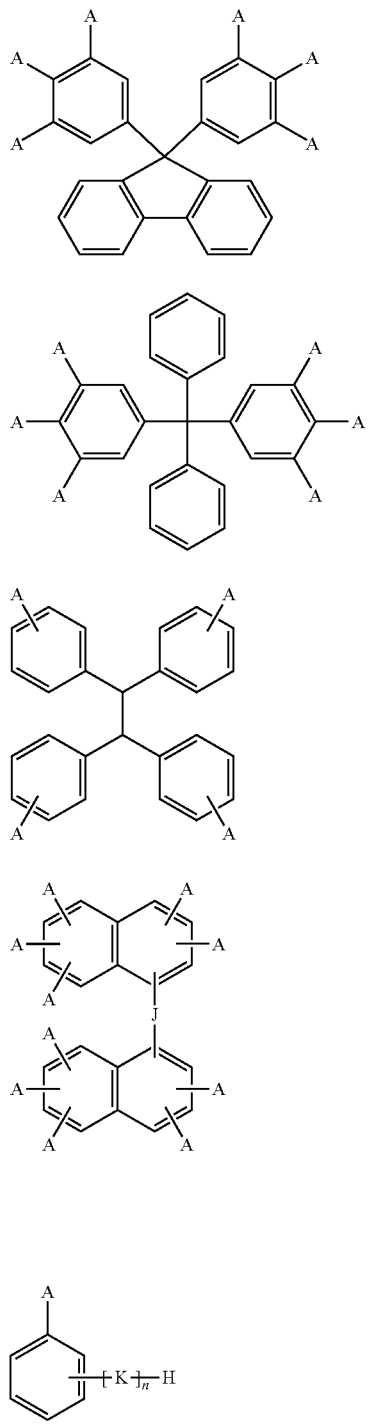

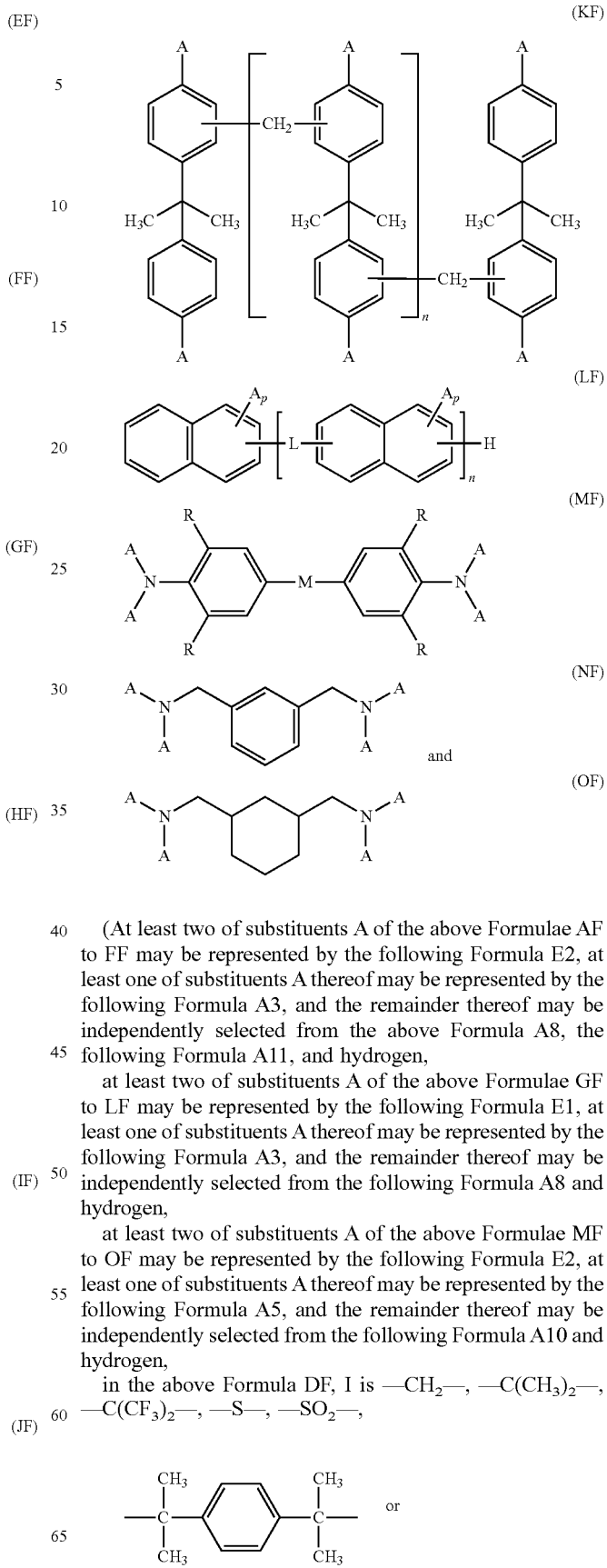

(At least two of substituents A of the above Formulae AF to FF may be represented by the following Formula E2, at least one of substituents A thereof may be represented by the following Formula A3, and the remainder thereof may be independently selected from the above Formula A8, the following Formula A11, and hydrogen, at least two of substituents A of the above Formulae GF to LF may be represented by the following Formula E1, at least one of substituents A thereof may be represented by the following Formula A3, and the remainder thereof may be independently selected from the following Formula A8 and hydrogen, at least two of substituents A of the above Formulae MF to OF may be represented by the following Formula E2, at least one of substituents A thereof may be represented by the following Formula A5, and the remainder thereof may be independently selected from the following Formula A10 and hydrogen, in the above Formula DF, I is $-CH_2-$, $-C(CH_3)_2-$, $-C(CF_3)_2-$, $-S-$, $-SO_2-$,

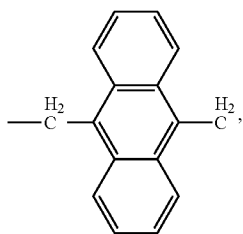

in the above Formula HF, J is a direct linkage, —CH$_2$—, or

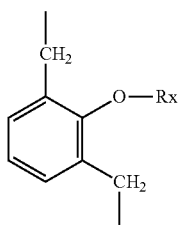

(Rx is H or a C$_1$-C$_3$ alkyl group), in the above Formula IF, K is one of the group consisting of the following formulae 1A to 1F,

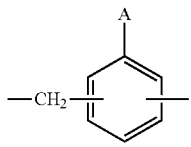  1A

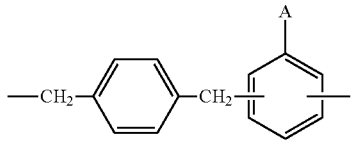  1B

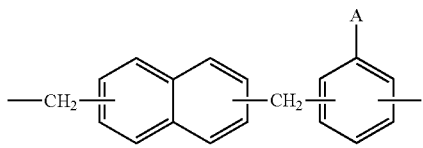  1C

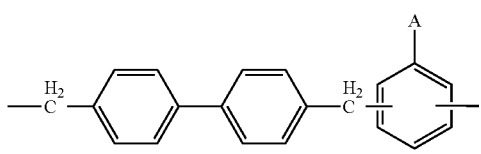  1D

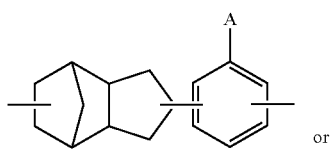  1E

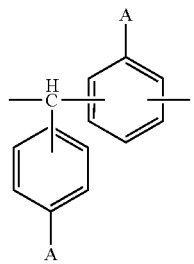  1F

In the above Formula LF, L is

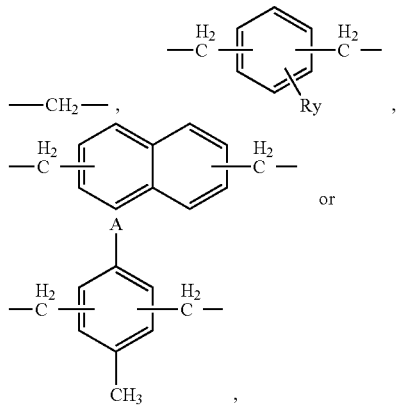

Ry is a linear or branched C1-C10 alkyl group, in the above Formula MF, M is —CH$_2$—, —C(CH$_3$)$_2$—, —C(CF$_3$)$_2$—, —S—, —SO$_2$—, or $$-\underset{\underset{CH_3}{|}}{\overset{\overset{CH_3}{|}}{C}}-\hspace{-2pt}\underset{}{\text{⬡}}-\underset{\underset{CH_3}{|}}{\overset{\overset{CH_3}{|}}{C}}-$$

and, R is H or C$_1$-C$_3$ alkyl, in the above Formula IF, when K is 1A to 1E, n is an integer of 3 or more, and when K is 1F, n is an integer of 2 or more, in the above Formula JF, n is an integer of 2 or more, in the above Formula KF, n is an integer of 0 or more, in the above Formula LF, when L is —CH$_2$—,  —C$H_2$—⬡$_{Ry}$—C$H_2$—  or -continued

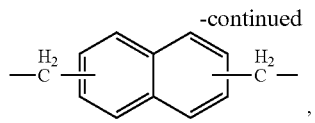

n is an integer of 3 or more, and
when L is

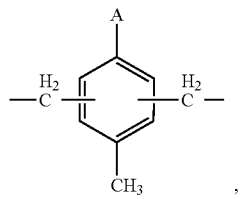

n is an integer of 2 or more, and
in the above Formula LF, p is 1 or 2.

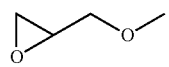 [Formula E]

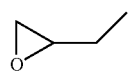 [Formula E2]

 [Formula A3]

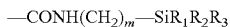 [Formula A5]

(In the above Formulae A3 and A5, at least one of $R_1$ to $R_3$ is an alkoxy group of 1 to 6 carbon atoms, and the remainder thereof are alkyl groups having 1 to 10 carbon atoms, wherein the alkyl groups and the alkoxy group may be linear or branched, may be cyclic or acyclic, and may or may not have an N, O, S, or P heteroatom, and m is an integer of 1 to 10.)

 [Formula A8]

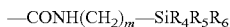 [Formula A10]

(In the above Formulae A8 and A10, $R_4$ to $R_6$ are non-reactive groups of the aliphatic, alicyclic, or aromatic moieties of 1 to 20 carbon atoms, wherein the non-reactive groups may be linear or branched, may be cyclic or acyclic, and may or may not have an N, O, S, or P heteroatom, and m is an integer of 1 to 10.)

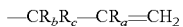 [Formula A11]

(In Formula A11, $R_a$, $R_b$ and $R_c$ are independently H or an alkyl group of 1 to 6 carbon atoms, wherein the alkyl group may be a linear or a branched, may be cyclic or acyclic, and may or may not have an N, O, S or P heteroatom.)

According to a fifteenth aspect, in the fourteenth aspect, there is provided the method of producing an epoxy compound, in which the starting material and alkoxysilane of the above Formula AS3 react with each other, such that the alkoxysilane of the above Formula AS3 with respect to 1 equivalent of an amine group or a hydroxy group of the starting material may be within a range of 0.1 equivalent to 5 equivalents.

According to a sixteenth aspect, in the fourteenth aspect, there is provided the method of producing an epoxy compound, in which when all of $R_1$ to $R_3$ of the alkoxysilane of the above Formula AS3 are methoxy, the starting material and alkoxysilane of the above Formula AS3 react with each other, such that the alkoxysilane of the above Formula AS3 with respect to 1 equivalent of an amine group or a hydroxy group of the starting material may be within a range of 0.1 equivalent or more and less than 1 equivalent.

According to a seventeenth aspect, there is provided an epoxy composition including the epoxy compound of any one of the first to ninth aspects.

According to an eighteenth aspect, there is provided an epoxy composition including the epoxy mixture of the tenth aspect.

According to a nineteenth aspect, in the seventeenth and eighteenth aspects, the epoxy composition may further include at least one type of epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound, and an aliphatic glycidyl amine-based epoxy compound.

According to a 20th aspect, in the 19th aspect, the epoxy compound may include, in a core structure, a bisphenol, a biphenyl, a naphthalene, abenzene, a thiodiphenol, a fluorene, anthracene, an isocyanurate, a triphenylmethane, a 1,1,2,2-tetraphenyl ethane, a tetraphenyl-methane, a 4,4'-diaminodiphenylmethane, an aminophenol, an alicyclic, an aliphatic, or a novolac unit.

According to a 21st aspect, in the 19th aspect, the epoxy composition may include, based on a total weight of the epoxy compound, 10 to 100 wt % of the epoxy compound having alkoxysilyl group, and 0 wt % to 90 wt % of at least one type of epoxy compound selected from the group consisting of a glycidyl ether-based epoxy compound, a glycidyl-based epoxy compound, a glycidyl amine-based epoxy compound, a glycidyl ester-based epoxy compound, a rubber-modified epoxy compound, an aliphatic polyglycidyl-based epoxy compound, and an aliphatic glycidyl amine-based epoxy compound.

According to a 22nd aspect, in any one of the 17th to 21st aspects, the epoxy composition may further include at least one type of filler selected from the group consisting of inorganic particles or fiber.

According to a 23rd aspect, in the 22nd aspect, the inorganic particles may be at least one selected from the group consisting of, at least one type of metal oxide selected from the group consisting of silica, zirconia, titania, alumina, silicon nitride and aluminum nitride, and silsesquioxane.

According to a 24th aspect, in the 22nd aspect, the fiber may be at least one selected from the group consisting of glass fiber and organic fiber, the glass fiber being selected from the group consisting of an E glass fiber, a T glass fiber, an S glass fiber, an NE glass fiber, an H glass fiber, and quartz, and the organic fiber being selected from the group consisting of liquid-crystal polyester fiber, polyethylene terephthalate fiber, wholly aromatic fiber, polybenzoxazole fiber, nylon fiber, polyethylene naphthalate fiber, polypropylene fiber, polyethersulfone fiber, polyvinylidene fluoride fiber, polyethylene sulfide fiber, and polyether ether ketone fiber.

According to a 25th aspect, when the fiber is included in the 22nd aspect, the epoxy composition may further include inorganic particles.

According to a 26th aspect, there is provided an electronic material including the epoxy composition of any one of the 17th to 25th aspects.

According to a 27th aspect, there is provided a substrate including the epoxy composition of any one of the 17th to 25th aspects.

According to a 28th aspect, there is provided a film including the epoxy composition of any one of the 17th to 25th aspects.

According to a 29th aspect, there is provided a laminate plate including a metal layer on a base layer formed of the epoxy composition of any one of the 17th to 25th aspects.

According to a 30th aspect, there is provided a printed wiring board including the laminate plate of the 29th aspect.

According to a 31st aspect, there is provided a semiconductor device including the printed wiring board of the 30th aspect.

According to a 32nd aspect, there is provided a semiconductor packaging material including the epoxy composition of any one of the 17th to 25th aspects.

According to a 33rd aspect, there is provided a semiconductor device including the semiconductor packaging material of the 32nd aspect.

According to a 34th aspect, there is provided an adhesive including the epoxy composition of any one of the 17th to 25th aspects.

According to a 35th aspect, there is provided a paint including the epoxy composition of any one of the 17th to 25th aspects.

According to a 36th aspect, there is provided a composite material including the epoxy composition of any one of the 17th to 25th aspects.

According to a 37th aspect, there is provided a prepreg including the epoxy composition of any one of the 13rd to 25th aspects.

According to a 38th aspect, there is provided a laminate plate in which a metal layer is disposed on the prepreg of the 37th aspect.

According to a 39th aspect, there is provided a cured product of the epoxy composition of any one of the 17th to 25th aspects.

According to a 40th aspect, in the 39th aspect, the cured product of the epoxy composition may have a coefficient of thermal expansion of 60 ppm/° C. or lower.

According to a 41st aspect, in the 39th aspect, the cured product of the epoxy composition may have a glass transition temperature higher than 100° C. or may not exhibit a glass transition temperature.

Advantageous Effects

As set forth above, according to an exemplary embodiment in the present disclosure, an epoxy composition including a novel epoxy compound may exhibit improved heat resistance, for example, reduction in a CTE of an epoxy composite, and increase of a glass transition temperature (including an effect in which a glass transition temperature is not observed (hereinafter, referred to as 'Tg-less')), in a composite and/or a cured product. In addition, a cured product of the epoxy composition according to an exemplary embodiment in the present disclosure may provide excellent flame retardant property due to the introduction of an alkoxysilyl group. Further, the epoxy composition according to an exemplary embodiment in the present disclosure may exhibit excellent processibility in a curing reaction. In detail, an increase in viscosity in a curing reaction may be easily controlled. Furthermore, a cured product of the epoxy composition may exhibit improved brittleness.

Furthermore, due to the improved efficiency of a chemical bond via the epoxy compound, a composition including an epoxy compound according to an exemplary embodiment in the present disclosure does not require a silane coupling agent, which has been generally used in an epoxy composition according to the related art.

BEST MODE FOR INVENTION

Figure 1A:
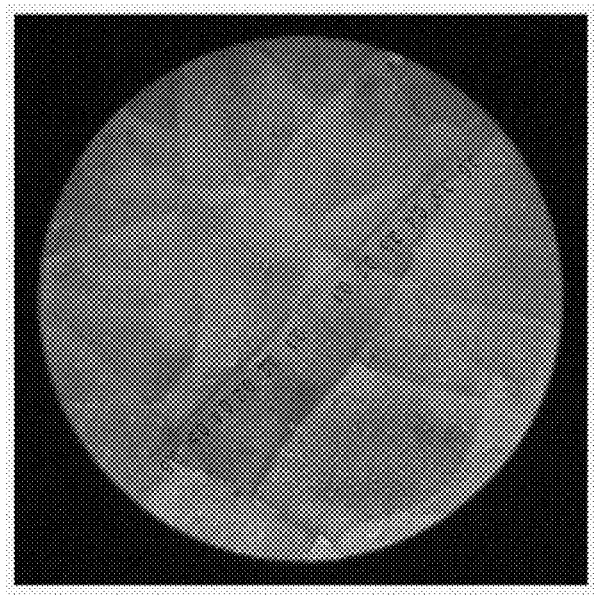
FIG. 1A is a microscope image (100× magnification) of the surface of a glass fiber composite produced using Comparative Synthesis Example 1.

The present disclosure provides a novel epoxy compound with the improved heat-resistant properties, in particular, a low coefficient of thermal expansion (CTE), and a high Tg (including Tg-less) when a composite is made by curing an epoxy composition, and/or excellent flame-retardant properties in a cured product, improved brittleness in a cured product, and/or curing reaction properties, such as viscosity increasing controllability, a method of producing the same, an epoxy composition and a cured product including the same, and a use thereof.

In the present disclosure, "composite" refers to a cured product of a composition including an epoxy compound and a filler (a fiber and/or inorganic particles). In the present disclosure, "cured product" refers to a cured product of a composition including an epoxy compound in a general sense, for example, a cured product of a composition including at least one selected from the group consisting of a filler, an optional and additional curing agent, an optional curing catalyst, and other additives as well as the epoxy compound and the curing agent. In addition, the cured product may include a partially-cured product. Generally, since a cured product reinforced with inorganic particles and/or a fiber is known as a composite, the cured product has a wider meaning than the composite. However, the cured product reinforced with inorganic particles and/or a fiber may be understood to have the same meaning as the composite.

A novel epoxy compound according to an exemplary embodiment may have a reactive group and a non-reactive group. Thus, when a composite is formed during a curing, crosslinking reaction occurs by the reaction of an epoxy group with a curing agent, and the reactive group may form interfacial bonding with the surface of a filler (a fiber and/or inorganic particles). Therefore, very high efficiency of good chemical bonding formation of an epoxy composite system may be exhibited, which results in a low CTE and a increase of the glass transition temperature (including Tg-less). Thus, dimensional stability may be improved. Furthermore, a separate silane coupling agent may not be required. In addition, a cured product including an epoxy compound according to an exemplary embodiment may exhibit excellent flame-retardant properties. Moreover, the non-reactive group may be present as a free end of a dangled moiety in a cured product, which leads to the improvements in the viscosity in the curing process and/or brittleness of a final cured product. The reactive group may be, in particular, an alkoxysilyl group, and the non-reactive group may be, for example, an alkylsilyl group.

1. Epoxy Compound

A novel epoxy compound according to an exemplary embodiment in the present disclosure may have, in a core, at least two epoxy groups; at least one alkoxysilyl group; and at least one non-reactive silyl group, an alkenyl group, or combinations thereof.

The epoxy group may be selected independently of Formulae E1 and E2.

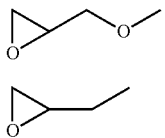

[Formula E1]

[Formula E2]

The alkoxysilyl group may be at least one selected from the group consisting of Formulae A1 to A5.

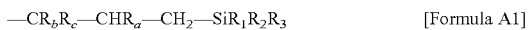  [Formula A1]

  [Formula A2]

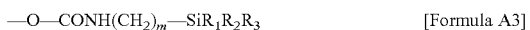  [Formula A3]

  [Formula A4]

  [Formula A5]

In Formula A1, each of $R_a$, $R_b$, and $R_c$ is independently hydrogen (H) or an alkyl group of 1 to 6 carbon atoms. In Formulae A1 to A5, at least one of $R_1$ to $R_3$ is an alkoxy group of 1 to 6 carbon atoms. The remainder thereof is an alkyl group of 1 to 10 carbon atoms. Each of the alkyl group and the alkoxy group may be linear or branched, may be cyclic or acyclic, and may or may not have an N, O, S, or P heteroatom. Moreover, m is an integer of 1 to 10.

The non-reactive silyl group may be at least one selected from the group consisting of Formulae A6 to A10.

In a preferable range of a ratio of the alkoxysilyl group to the non-reactive silyl group, improved heat-resistant properties (a reduction in CTE and/or an increase in a glass transition temperature), increasing the controllability of viscosity increase effect, and a brittleness reducing effect in a composite intended according to an exemplary embodiment are exhibited, these physical properties may be more preferable within the preferable range, and the preferable range may be suitable in a case in which the epoxy composite is used as semiconductor packaging.

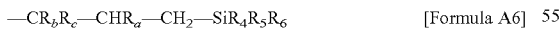  [Formula A6]

  [Formula A7]

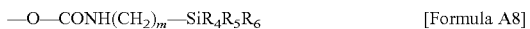  [Formula A8]

  [Formula A9]

  [Formula A10]

In Formula A6, each of $R_a$, $R_b$, and $R_c$ is independently hydrogen (H) or an alkyl group of 1 to 6 carbon atoms. In Formulae A6 to A10, $R_4$ to $R_6$ are a non-reactive groups of an aliphatic, alicyclic, or aromatic moieties of 1 to 20 carbon atoms. The non-reactive group may be linear or branched, may be cyclic or acyclic, and may or may not have an N, O, S, or P heteroatom. Moreover, m is an integer of 1 to 10.

Meanwhile, the alkenyl group may be selected from the group consisting of Formulae A11 to A13.

  [Formula A11]

  [Formula A12]

  [Formula A13]

In Formula A11, each of $R_a$, $R_b$, and $R_c$ is independently hydrogen (H) or an alkyl group of 1 to 6 carbon atoms. The alkyl group may be linear or branched, may be cyclic or acyclic, and may or may not have an N, O, S, or P heteroatom. In Formulae A12 and A13, m is an integer of 1 to 10.

According to an exemplary embodiment, an alkenyl group includes all chemical groups able to be obtained by removing a single hydrogen atom from an alkene compound or a derivative thereof, includes an allyl group, a butenyl group, a pentenyl group, or the like, and these terms may be used interchangeably.

A structure of the core may be bisphenol, biphenyl, naphthalene, benzene, thiodiphenol, fluorene, tetraphenylethane, tetraphenylmethane, diaminodiphenylmethane, alicyclic, aliphatic, or novolak unit, etc.

More particularly, the core is an aromatic core, and may be at least one selected from the group consisting of Formulae AC to OC. According to an exemplary embodiment, the core is understood as including both of structures of Formulae AC to HC and Formulae MC to OC and repeating units of Formulae IC to LC.

  (AC)

  (BC)

  (CC)

  (DC)

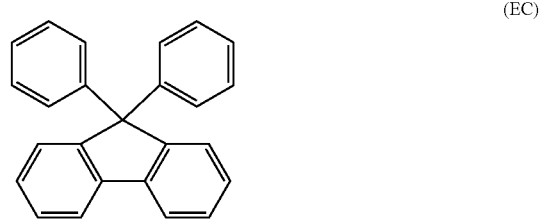  (EC)

-continued
(FC) 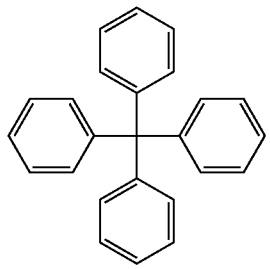
(GC) 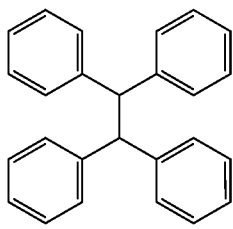
(HC) 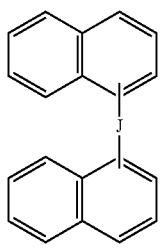
(IC) 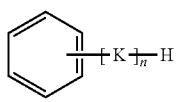
(LC) 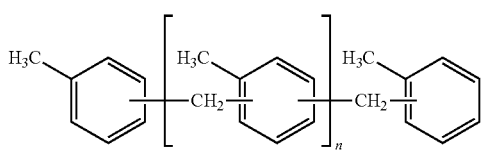
(KC) 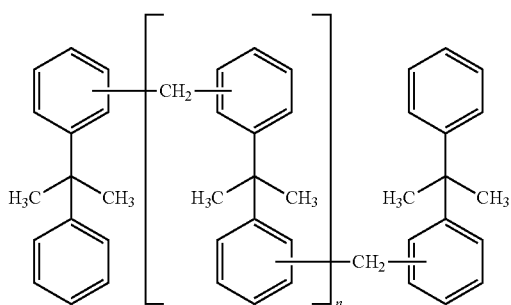
(LC) 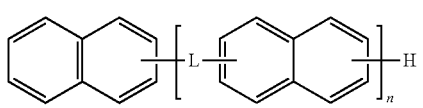
(MC) 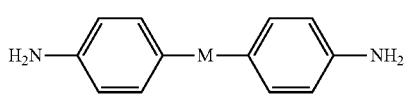
-continued
(NC) 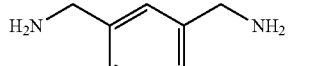
and
(OC) 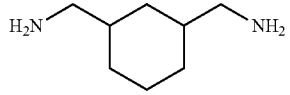
In Formula DC, I is —CH$_2$—, —C(CH$_3$)$_2$—, —C(CF$_3$)$_2$—, —S—, —SO$_2$—, or
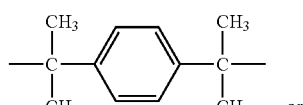
or
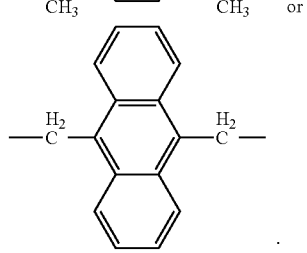
In Formula HC, J is direct linkage, —CH$_2$— or—
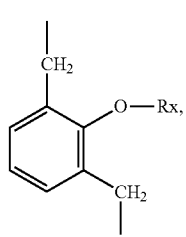
wherein Rx is hydrogen (H) or an alkyl group of C1-C3.
In Formula IC, K is at least one selected from the group consisting of Formulae 1ac to 1fc.
1ac 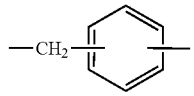
1bc 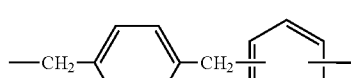
1cc 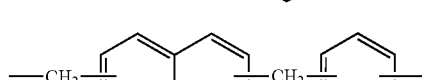
1dc 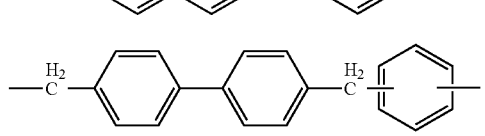

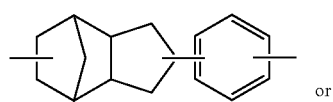

or

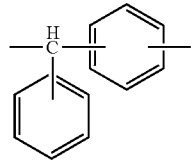

In Formula LC, L is

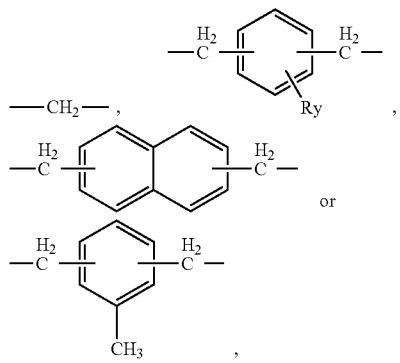

and in

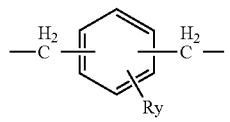

Ry is a linear or branched alkyl group of C1-C10.

In Formula MC, M is —CH$_2$—, —C(CH$_3$)$_2$—, —C(CF$_3$)$_2$—, —S—, —SO$_2$—, or—

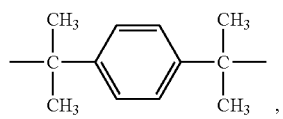

and R is hydrogen (H) or an alkyl group of C1-C3.

In Formula IC, when K is Formulae 1ac to 1ec, n is an integer of 3 or more, and when K is Formula 1fc, n is an integer of 2 or more.

In Formulae JC, n is an integer of 2 or more.

In Formulae KC, n is an integer of 0 or more.

In Formula LC, when L is

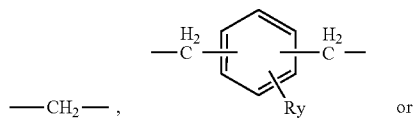

n is an integer of 3 or more, and when L is—

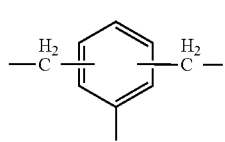

n is an integer of 2 or more.

In Formulae IC to LC, maximum of n is 1,000.

Furthermore, in the epoxy compound, when cores of Formulae AC to HC and Formulae MC to OC are two or more (in this case, the cores are the same type, and when cores according to an exemplary embodiment are two or more, the above is applied thereto in the same manner), the cores may be connected by a linking group (LG). As occasion demands, 1 to 1,000 of core structures may be additionally connected. In particular, the cores of Formulae AC to HC may be connected by a linking group of Formula LG1, and the cores of Formulae MC to OC may be connected by a linking group of Formula LG2.

[Formula LG1]

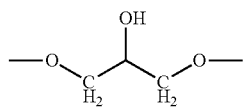

[Formula LG2]

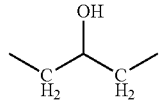

In particular, a novel epoxy compound according to an exemplary embodiment in the present disclosure may be Formulae AF to OF.

(AF)

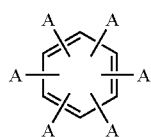

(BF)

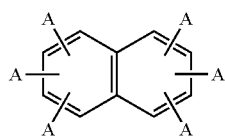

(CF)

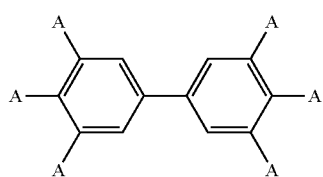

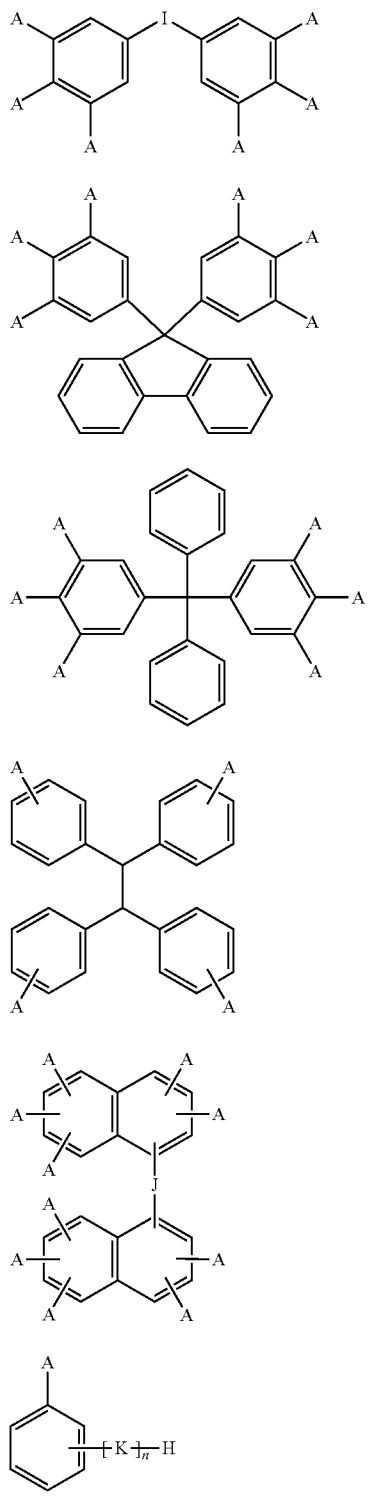
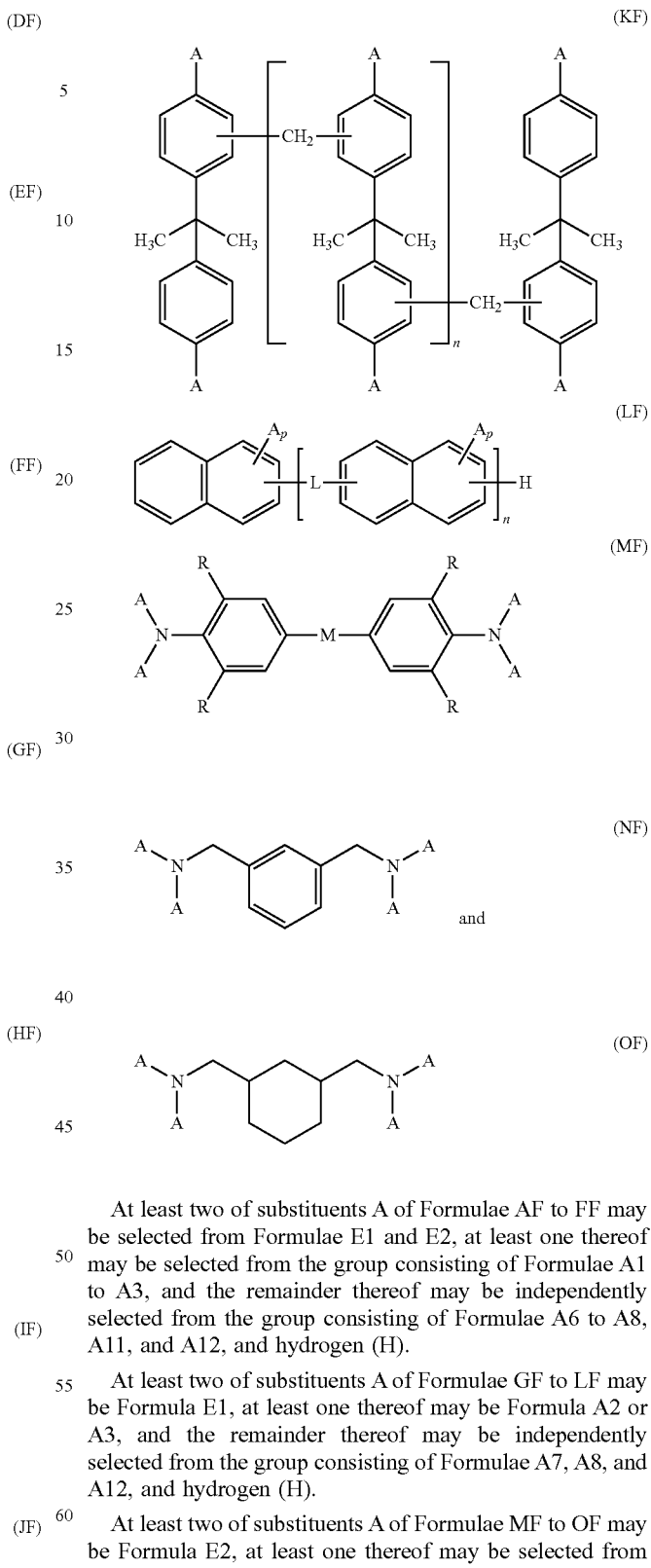

At least two of substituents A of Formulae AF to FF may be selected from Formulae E1 and E2, at least one thereof may be selected from the group consisting of Formulae A1 to A3, and the remainder thereof may be independently selected from the group consisting of Formulae A6 to A8, A11, and A12, and hydrogen (H).

At least two of substituents A of Formulae GF to LF may be Formula E1, at least one thereof may be Formula A2 or A3, and the remainder thereof may be independently selected from the group consisting of Formulae A7, A8, and A12, and hydrogen (H).

At least two of substituents A of Formulae MF to OF may be Formula E2, at least one thereof may be selected from Formulae A4 and A5, and the remainder thereof may be independently selected from the group consisting of Formulae A9, A10, and A13, and hydrogen (H).

In Formula DF, I is —CH$_2$—, —C(CH$_3$)$_2$—, —C(CF$_3$)$_2$—, —S—, —SO$_2$—,

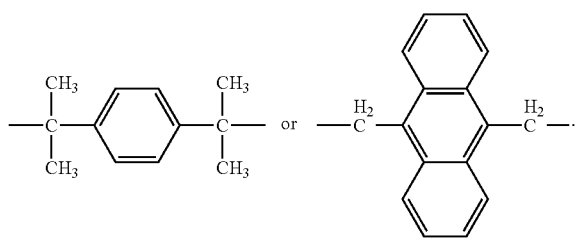

In Formula HF, J is direct linkage, —CH$_2$— or—

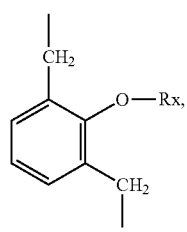

wherein, Rx is hydrogen (H) or an alkyl group of C1-C3.

In Formula IF, K is at least one selected from the group consisting of Formulae 1A to 1F.

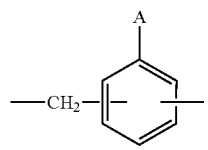
1A

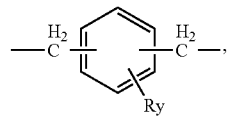
1B

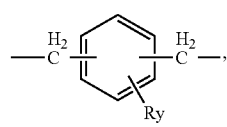
1C

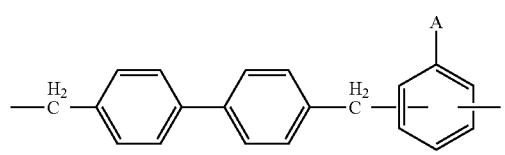
1D

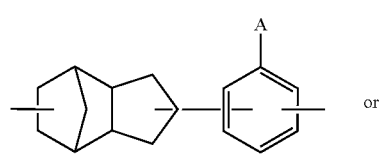
1E

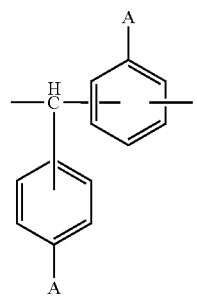
1F

In Formula LF, L is

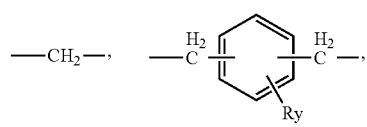

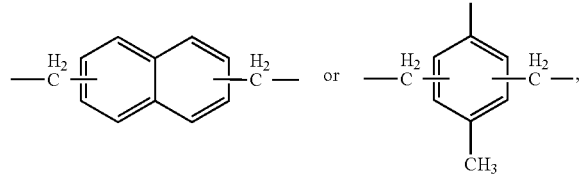

and in

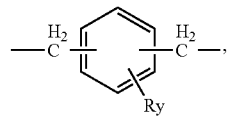

Ry is a linear or branched alkyl group of C1-C10.

In Formula MF, M is —CH$_2$—, —C(CH$_3$)$_2$—, —C(CF$_3$)$_2$—, —S—, —SO$_2$—, or

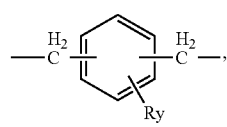

and R is hydrogen (H) or an alkyl group of C1-C3.

In Formula IF, when K is Formulae 1A to 1E, n is an integer of 3 or more, and when K is Formula 1F, n is an integer of 2 or more.

In Formulae JF, n is an integer of 2 or more.

In Formulae KF, n is an integer of 0 or more.

In Formula LF, when L is

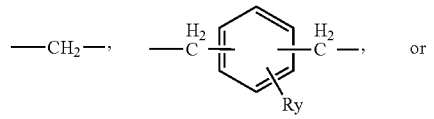

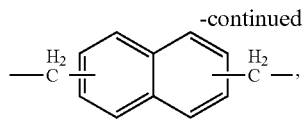

n is an integer of 3 or more, and when L is

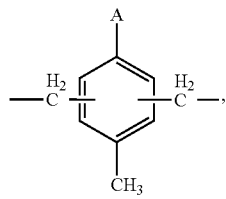

n is an integer of 2 or more.

In Formula LF, p is 1 or 2. In Formulae IF to LF, n is a maximum of 1,000.

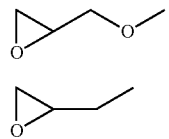 [Formula E1]

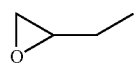 [Formula E2]

—$CR_bR_c$—$CHR_a$—$CH_2$—$SiR_1R_2R_3$ [Formula A1]

—O—$(CH_2)_{m+2}$—$SiR_1R_2R_3$ [Formula A2]

—O—$CONH(CH_2)_m$—$SiR_1R_2R_3$ [Formula A3]

—$(CH_2)_{m+2}$—$SiR_1R_2R_3$ [Formula A4]

—$CONH(CH_2)_m$—$SiR_1R_2R_3$ [Formula A5]

In Formula A1, each of $R_a$, $R_b$, and $R_c$ is independently hydrogen (H) or an alkyl group of 1 to 6 carbon atoms. In Formulae A1 to A5, at least one of $R_1$ to $R_3$ is an alkoxy group of 1 to 6 carbon atoms. The remainder thereof is an alkyl group of 1 to 10 carbon atoms. Each of the alkyl group and the alkoxy group may be linear or branched, may be cyclic or acyclic, and may or may not have an N, O, S, or P heteroatom. Moreover, m is an integer of 1 to 10.

—$CR_bR_c$—$CHR_a$—$CH_2$—$SiR_4R_5R_6$ [Formula A6]

—O—$(CH_2)_{m+2}$—$SiR_4R_5R_6$ [Formula A7]

—O—$CONH(CH_2)_m$—$SiR_4R_5R_6$ [Formula A8]

—$(CH_2)_{m+2}$—$SiR_4R_5R_6$ [Formula A9]

—$CONH(CH_2)_m$—$SiR_4R_5R_6$ [Formula A10]

In Formula A6, each of $R_a$, $R_b$, and $R_c$ is independently hydrogen (H) or an alkyl group of 1 to 6 carbon atoms. In Formulae A6 to A10, $R_4$ to $R_6$ are a non-reactive groups of an aliphatic, alicyclic, or aromatic moieties of 1 to 20 carbon atoms. The non-reactive group may be linear or branched, may be cyclic or acyclic, and may or may not have an N, O, S, or P heteroatom. Moreover, m is an integer of 1 to 10.

—$CR_bR_c$—$CR_a$=$CH_2$ [Formula A11]

—O—$(CH_2)_m$—CH=$CH_2$ [Formula A12]

—$(CH_2)_m$—CH=$CH_2$ [Formula A13]

In Formula A11, each of $R_a$, $R_b$, and $R_c$ is independently hydrogen (H) or an alkyl group of 1 to 6 carbon atoms. The alkyl group may be linear or branched, may be cyclic or acyclic, and may or may not have an N, O, S, or P heteroatom. In Formulae A12 and A13, m is an integer of 1 to 10.

The epoxy compound may be an epoxy compound, which has, for example, in a core, (i) at least two epoxy groups represented by Formula E1

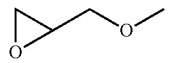 [Formula E1]

(ii) at least one alkoxysilyl group represented by Formula A1:

—$CR_bR_c$—$CHR_a$—$CH_2$—$SiR_1R_2R_3$ [Formula A1]

In Formula A1, each of $R_a$, $R_b$, and $R_c$ is independently hydrogen (H) or an alkyl group of 1 to 6 carbon atoms. At least one thereof is an alkoxy group of 1 to 6 carbon atoms. The remainder thereof is an alkyl group of 1 to 10 carbon atoms. Each of the alkyl group and the alkoxy group may be linear or branched, may be cyclic or acyclic, and may or may not have an N, O, S, or P heteroatom. Moreover, m is an integer of 1 to 10; and (iii) at least one alkenyl group represented by Formula A11:

—$CR_bR_c$—$CR_a$=$CH_2$ [Formula A11]

In Formula A11, each of $R_a$, $R_b$, and $R_c$ is independently hydrogen (H) or an alkyl group of 1 to 6 carbon atoms. The alkyl group may be linear or branched, may be cyclic or acyclic, and may or may not have an N, O, S, or P heteroatom.

In the epoxy compound, at least one of $R_1$ to $R_3$ in an alkoxysilyl group represented by Formulae A1 to A5 may be an alkoxy group of 2 to 4 carbon atoms, and may preferably be an ethoxy group in the alkoxysilyl group represented by Formulae A1 to A5.

Meanwhile, when all of $R_1$ to $R_3$ are methoxy groups in the alkoxysilyl group represented by Formulae A1 to A5, an epoxy compound according to an exemplary embodiment may preferably include at least one alkenyl group. When all of $R_1$ to $R_3$ are methoxy groups in the alkoxysilyl group and do not include at least one alkenyl group, reactivity of a methoxysilyl group is excessively high so that control of the reaction rate thereof is difficult due to a rapid increase in viscosity, or the like, and brittleness of a cured sample are excessively high so that the application for a material is difficult. In contrast, when all of $R_1$ to $R_3$ are methoxy groups in the alkoxysilyl group and include at least one alkenyl group, the reaction rate may be controlled, and brittleness of a cured sample may be reduced due to an alkenyl group present in a cured structure.

According to an exemplary embodiment in the present disclosure, an epoxy mixture including a novel epoxy compound according to an exemplary embodiment in the present disclosure is also provided.

In a mixture including a novel epoxy compound according to an exemplary embodiment, when the novel epoxy compound includes a non-reactive silyl group, a ratio of an alkoxysilyl group to the non-reactive silyl group is 1:99 to 99:1, and may preferably be 5:95 to 95:5. When the ratio of the alkoxysilyl group to the non-reactive silyl group is lower than 1:99, a concentration of the alkoxysilyl group is excessively low so that a sufficient level of physical properties is not secured. When the ratio of the alkoxysilyl group to the non-reactive silyl group is greater than 99:1, a concentration of the non-reactive silyl group is excessively low so that brittleness properties are not substantially reduced. A ratio of an epoxy group to the alkoxysilyl group in the mixture including the novel epoxy compound may be 10:1 to 1:10. When the ratio of the epoxy group to the alkoxysilyl group is lower than 1:10, crosslinking density of a cured epoxy product may be decreased to cause a degradation in physical properties thereof. When the ratio of the epoxy group to the alkoxysilyl group is lower than 10:1, a heat resistance improvement effect by the alkoxysilyl group may be reduced. Furthermore, the ratio of the alkoxysilyl group to the non-reactive silyl group in the mixture including the novel epoxy compound is 1:99 to 99:1, and may preferably be 5:95 to 95:5, and the ratio of the epoxy group to the alkoxysilyl group is 10:1 to 1:10, and may be, for example, 1:1 to 5:1.

In addition, the ratio of the alkoxysilyl group to the non-reactive silyl group and/or the ratio of the epoxy group to the alkoxysilyl group is preferably the same as defined above in an epoxy composition according to an exemplary embodiment in the present disclosure to be described below. Accordingly, an epoxy compound included in the epoxy composition to be described below may be the abovementioned epoxy compound.

Meanwhile, when an epoxy compound according to an exemplary embodiment includes an alkenyl group, a reaction between a starting material and the alkoxysilane of Formula AS5 where 0.1 to 5 equivalents of the alkoxysilane of Formula AS5 are used with respect to 1 equivalent of the alkenyl group of the starting material is more preferable. When the reaction is performed using less than 0.1 equivalent of the alkoxysilane of Formula AS5 with respect to 1 equivalent of the alkenyl group of the starting material, a rate of the reaction of the alkoxysilyl group and a degree of silylation in a final epoxy compound structure may be significantly reduced. When the reaction is performed using more than 5 equivalents of the alkoxysilane of Formula AS5 with respect to 1 equivalent of the alkenyl group of the starting material, a concentration of an unreacted alkoxysilyl group included in an excessive amount may be significantly increased.

In addition, particularly, when all of $R_1$ to $R_3$ of the alkoxysilane of Formula AS5 are methoxy groups, the reaction where 0.1 equivalent or more and less than 1 equivalent of the alkoxysilane of Formula AS5 is used with respect to 1 equivalent of the alkenyl group of the starting material is more preferable.

When the reaction is performed using less than 0.1 equivalent of the alkoxysilane of Formula AS5 with respect to 1 equivalent of the alkenyl group of the starting material, a rate of the reaction of the methoxysilyl group and a degree of silylation in the final epoxy compound structure may be significantly reduced. When the reaction is performed using more than 1 equivalent of the alkoxysilane of Formula AS5 with respect to 1 equivalent of the alkenyl group of the starting material, a concentration of the methoxysilyl group in the final epoxy compound structure may be significantly increased.

For example, a novel epoxy compound according to an exemplary embodiment in the present disclosure may allow a non-reactive starting material and a reactive by-product (for example, a compound only having an epoxy group and an alkoxysilyl group or a compound only having an epoxy group and a non-reactive silyl group) that does not meet the definition of an epoxy compound defined according to an exemplary embodiment in the present disclosure to be obtained in a state of a mixture, due to a non-reaction and/or incomplete reaction, in a process of producing the novel epoxy compound, as described below in detail. In the entirety of the mixture of the epoxy compound, a ratio of an alkoxysilyl group to a non-reactive silyl group and/or a ratio of an epoxy group to an alkoxysilyl group may be the abovementioned range, and the mixture of the epoxy compound itself may be used in an epoxy composition to be described below.

In the present application, "alkoxy group" denotes a monovalent group of —OR (R is an alkyl group) and may be linear or branched.

In the present application, "alkyl group" denotes a monovalent hydrocarbon group and may be linear or branched.

When a plurality of substituents are present in the abovementioned or following Formula, each of the substituents may be independently selected. For example, when at least two of substituents A of Formulae AF to FF are selected from Formulae A1 to A3, each of a plurality of substituents A may each be independently selected from Formulae A1 to A3. Also, when all of the A's are Formula A2, $R_1$ to $R_3$ of Formula A2 may be the same or different.

Furthermore, an epoxy compound according to an exemplary embodiment in the present disclosure may exhibit a low CTE and a high glass transition temperature or Tg-less in a composite of a composition including the epoxy compound. Moreover, the non-reactive silyl group and the alkenyl group may not participate in additional chemical bonding and may be present as dangled moieties on a crosslinking network of a epoxy cured product, which leads to thus improvements of viscosity in a curing process and/or brittleness of a final cured product.

2. Method of Producing Epoxy Compound

The epoxy compound of Formulae AF to OF according to an exemplary embodiment in the present disclosure may be synthesized by two methods as described below.

Namely, the epoxy compound according to an exemplary embodiment may be synthesized by the hydrosilylation method of of double bond, that is, alkoxysilylation and non-reactive silylation of an epoxy compound having an epoxy group and an alkenyl group (Method 1) or of the reaction of a hydroxy group or an amine group with isocyanate silane coupling agent, that is, silylation of epoxy compound with a hydroxy group and/or an amine group (Method 2).

(1) Method 1

As described above, an epoxy compound according to an exemplary embodiment is manufactured by alkoxysilylation and non-reactive silylation of an alkenyl group of a starting material, for example, the epoxy compound with an epoxy group and the alkenyl group.

The epoxy compound with the epoxy group and the alkenyl group is hereinafter referred to as a starting material for convenience. The starting material may particularly be a compound of Formulae AS1 to OS1.

(Starting material 1)

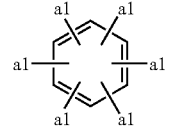

(AS1)

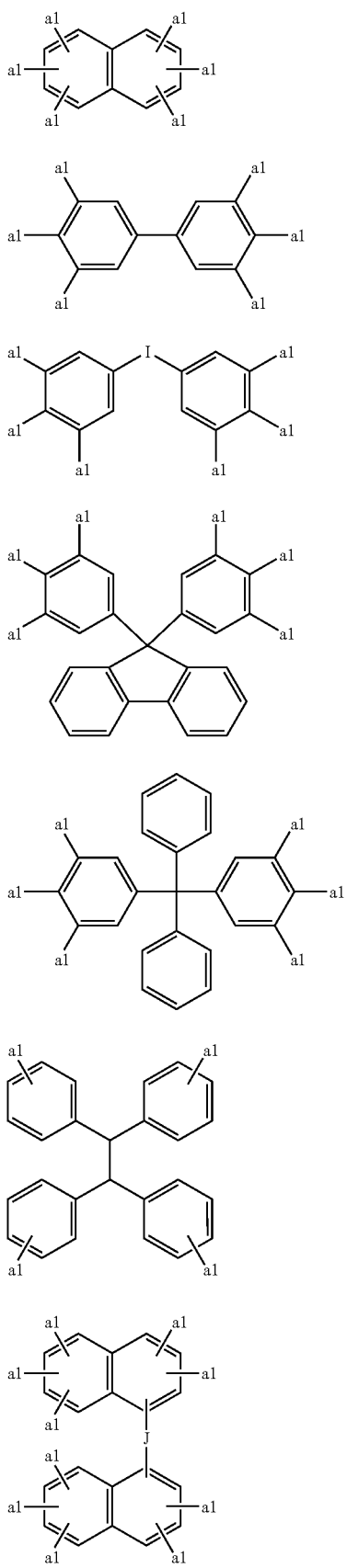
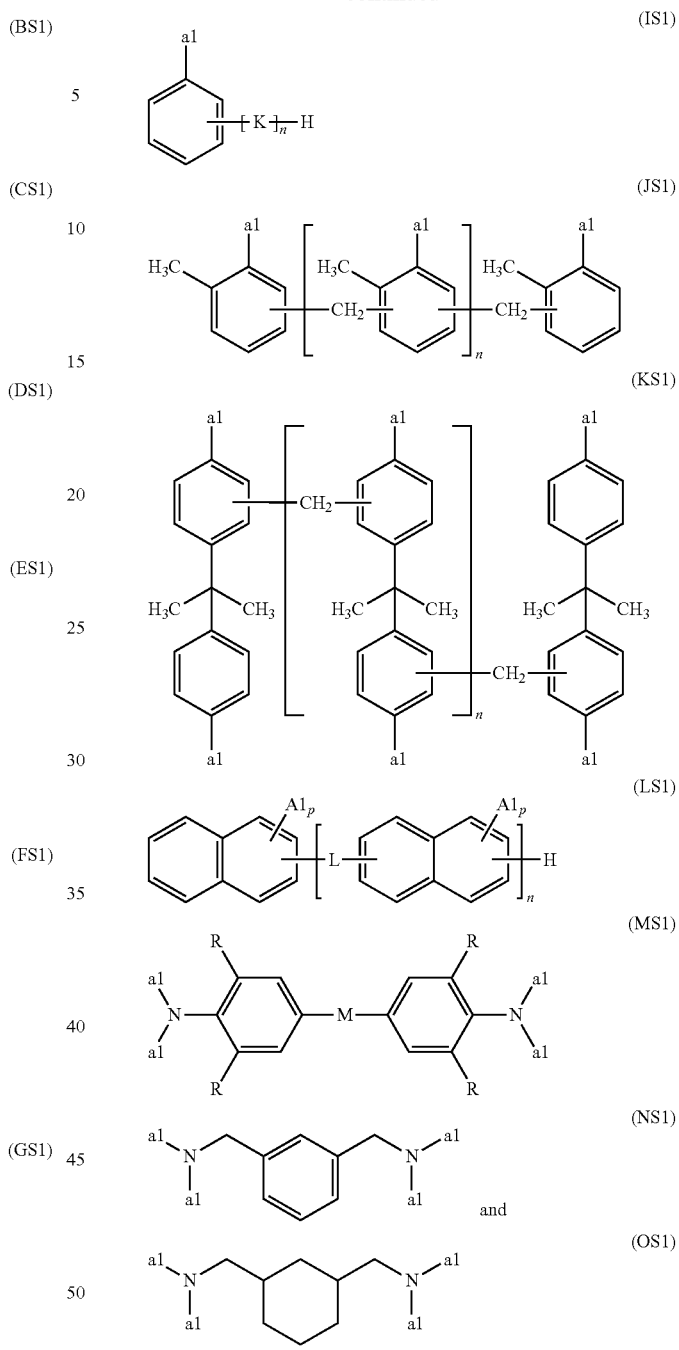

At least two of a plurality of substituents a1 of Formulae AS1 to FS1 are Formula E1 or E2, at least two thereof are Formula A11 or A12, and the remainder thereof may be hydrogen (H).

At least two of a plurality of substituents a1 of Formulae GS1 to LS1 are Formula E1, at least two thereof are Formula A12, and the remainder thereof may be hydrogen (H).

At least two of a plurality of substituents a1 of Formulae MS1 to OS1 are Formula E2, and the remainder thereof may be Formula A13.

In Formula DS1, I is —CH$_2$—, —C(CH$_3$)$_2$—, —C(CF$_3$)$_2$—, —S—, —SO$_2$—,

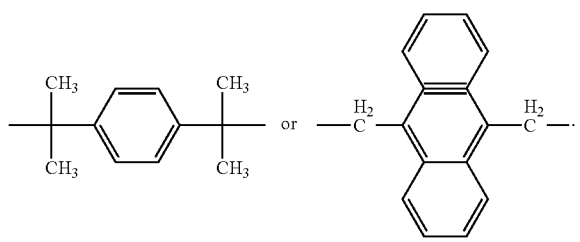

In Formula HS1, J is direct linkage, —CH$_2$— or

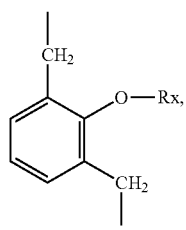

and Rx is hydrogen (H) or an alkyl group of C1-C3. In Formula IS1, K is at least one selected from the group consisting of Formulae 1a1 to 1f1.

1a1

—CH$_2$—〈a1〉

1b1

—CH$_2$—〈 〉—CH$_2$—〈a1〉

1c1

—CH$_2$—〈naphthalene〉—CH$_2$—〈a1〉

1d1

—CH$_2$—〈 〉—〈 〉—CH$_2$—〈a1〉

1e1

—〈norbornane-indane〉—〈a1〉 or

1f1

—CH〈a1〉〈a1〉 (methine with two a1 aryl groups)

In Formula LS1, L is

—CH$_2$—, —C(H$_2$)—〈 〉Ry—C(H$_2$)—,

—C(H$_2$)—〈naphthalene〉—C(H$_2$)— or —C(H$_2$)—〈a1, CH$_3$〉—C(H$_2$)—, and in

—C(H$_2$)—〈Ry〉—C(H$_2$)—,

Ry is a linear or branched alkyl group of C1-C10.

In Formula MS1, M is —CH$_2$—, —C(CH$_3$)$_2$—, —C(CF$_3$)$_2$—, —S—, —SO$_2$—, or—

—C(CH$_3$)$_2$—〈 〉—C(CH$_3$)$_2$—, and R is hydrogen (H) or an alkyl group of C1-C3.

In Formula IS1, when K is Formulae 1a1 to 1e1, n is an integer of 3 or more, and when K is Formula 1f1, n is an integer of 2 or more.

In Formulae JS1, n is an integer of 2 or more.

In Formulae KS1, n is an integer of 0 or more.

In Formula LS1, when L is

—CH$_2$— , —C(H$_2$)—〈Ry〉—C(H$_2$)— or

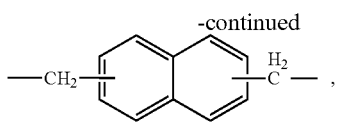

n is an integer of 3 or more, and when L is—

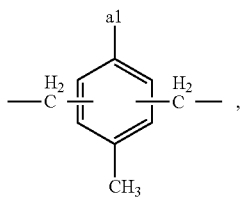

n is an integer of 2 or more.

In Formula LS1, p is 1 or 2. In Formulae IS1 to LS1, n is a maximum of 1,000.

In particular, the alkoxysilylation and non-reactive silylation of the alkenyl group of the starting material is performed in the presence of a platinum catalyst and optional solvent to obtain an epoxy compound with at least two epoxy groups, at least one alkoxysilyl group, and at least one non-reactive functional group, particularly, a non-reactive silyl group and an alkenyl group according to an exemplary embodiment in the present disclosure.

Since the reaction between the alkenyl group of the starting material and alkoxysilane of Formula AS5 is performed in accordance with stoichiometry thereof, the reaction between the starting material and the alkoxysilane of Formula AS5 is performed using 0.1 to 5 equivalents of the alkoxysilane with respect to 1 equivalent of the alkenyl group of the starting material in consideration of stoichiometry.

Particularly, when all of $R_1$ to $R_3$ of the alkoxysilane of Formula AS5 are methoxy groups, the reaction where 0.1 equivalent or more and less than 1 equivalent of the alkoxysilane of Formula AS5 is used with respect to 1 equivalent of the alkenyl group of the starting material is more preferable. In the case of using below the concentration range of the alkoxysilane, a reaction rate of a methoxysilyl group and a degree of silylation in a final epoxy compound structure may be excessively low. In the case of using the above the concentration range of alkoxysilane, a concentration of the methoxysilyl group may be excessively high in the final epoxy compound structure.

$$HSiR_1R_2R_3 \quad \text{[Formula AS5]}$$

In Formula AS5, at least one of $R_1$ to $R_3$ is an alkoxy group of C1 to C6, preferably an ethoxy group, the remainder thereof is an alkyl group of C1 to C10, the alkoxy group and the alkyl group may be linear or branched, may be cyclic or acyclic, and may or may not have an N, O, S, or P heteroatom.

In addition, since the reaction between the alkenyl group of the starting material and non-reactive silane of Formula AS6 is performed in accordance with stoichiometry thereof, the reaction between the starting material and the non-reactive silane is performed using 0.1 to 5 equivalents of the non-reactive silane with respect to 1 equivalent of the alkenyl group of the starting material in consideration of the stomichiometry.

$$HSiR_4R_5R_6 \quad \text{[Formula AS6]}$$

In Formula A6, $R_4$ to $R_6$ are a non-reactive groups of an aliphatic, alicyclic, or aromatic moieties of 1 to 20 carbon atoms, the non-reactive group may be linear or branched, may be cyclic or acyclic, and may or may not have an N, O, S, or P heteroatom.

The reaction between the starting material, the alkoxysilane and the non-reactive silane may include (1) the reaction of the starting material with the alkoxysilane and the non-reactive silane, simultaneously and (2) the reaction of the starting material with the alkoxysilane and then in-situ reaction of a reaction product with the non-reactive silane.

A reaction temperature and a reaction time of the starting material and the alkoxysilane may be changed depending on the structure of the reacting material, and the reaction may be performed, for example, at a temperature of from −20° C. to 120° C. for 1 hour to 72 hours. By performing the reaction at the reaction temperature for the reaction time, a desired reaction may be completed.

The platinum catalyst may be, for example, $PtO_2$ or chloroplatinic acid ($H_2PtCl_6$), without limitation. $1 \times 10^{-4}$ to 0.05 equivalents of the platinum catalyst with respect to 1 equivalent of the alkenyl group of the starting material may preferably be used in consideration of reaction efficiency.

The solvent may be used optionally as occasion demands. For example, the solvent may not be used in a case in which viscosity of the reacting material at the reaction temperature is appropriate for carrying out the reaction without a separate solvent. Namely, when the viscosity of the reacting material is so low that mixing and stirring of the reacting material may be smoothly performed without a solvent, a separate solvent is not required. This may be easily determined by a person skilled in the art. In a case in which the solvent is used, any aprotic solvent may be used, as an available solvent, if able to dissolve the reacting material properly, not inducing any adverse influence on the reaction, and being easily removed after the reaction. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used, without limitation. These solvents may be used alone or as a mixture of two or more thereof. The use amount of the solvent may not be particularly limited, and an appropriate amount and/or concentration of the solvent may be used within a range suitable for sufficiently dissolving the reacting material and not adversely affecting the reaction. A person skilled in the art may select an appropriate amount and/or concentration of the solvent in consideration of the above-mentioned points.

A reaction scheme of a novel epoxy compound according to an exemplary embodiment is as follows.

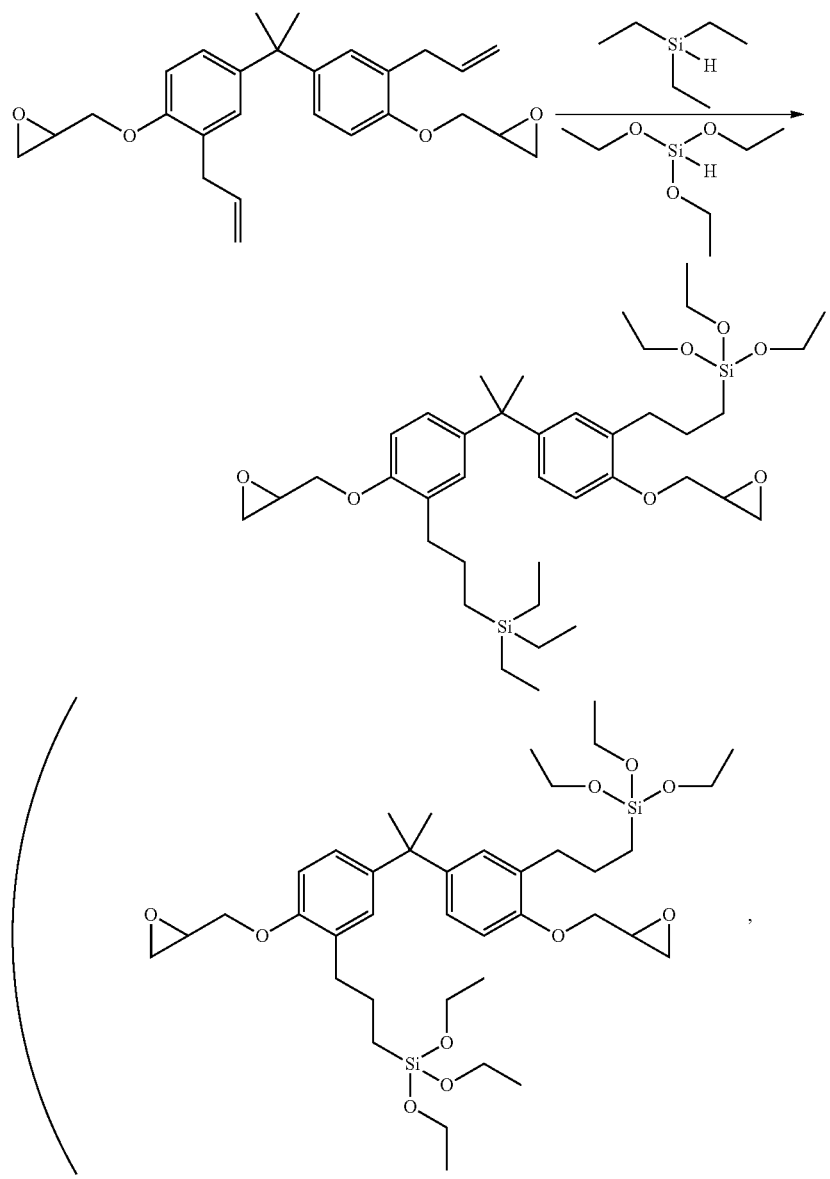
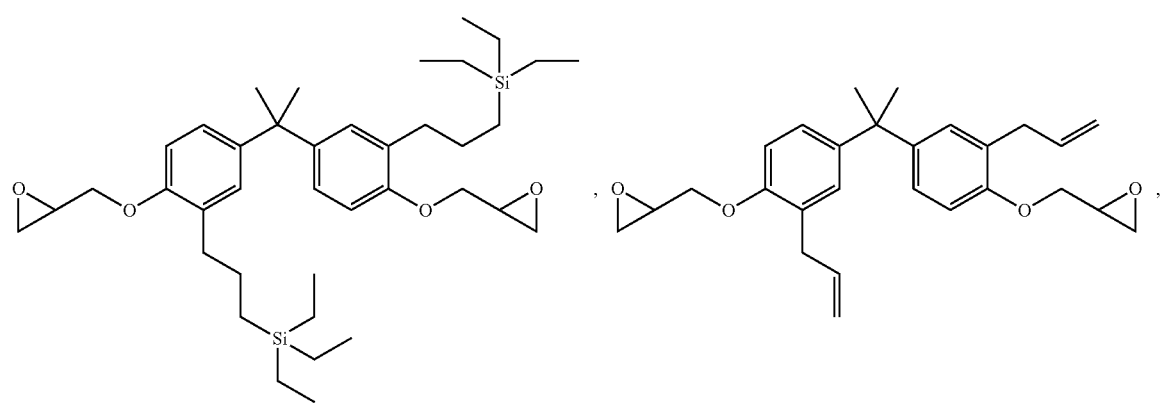

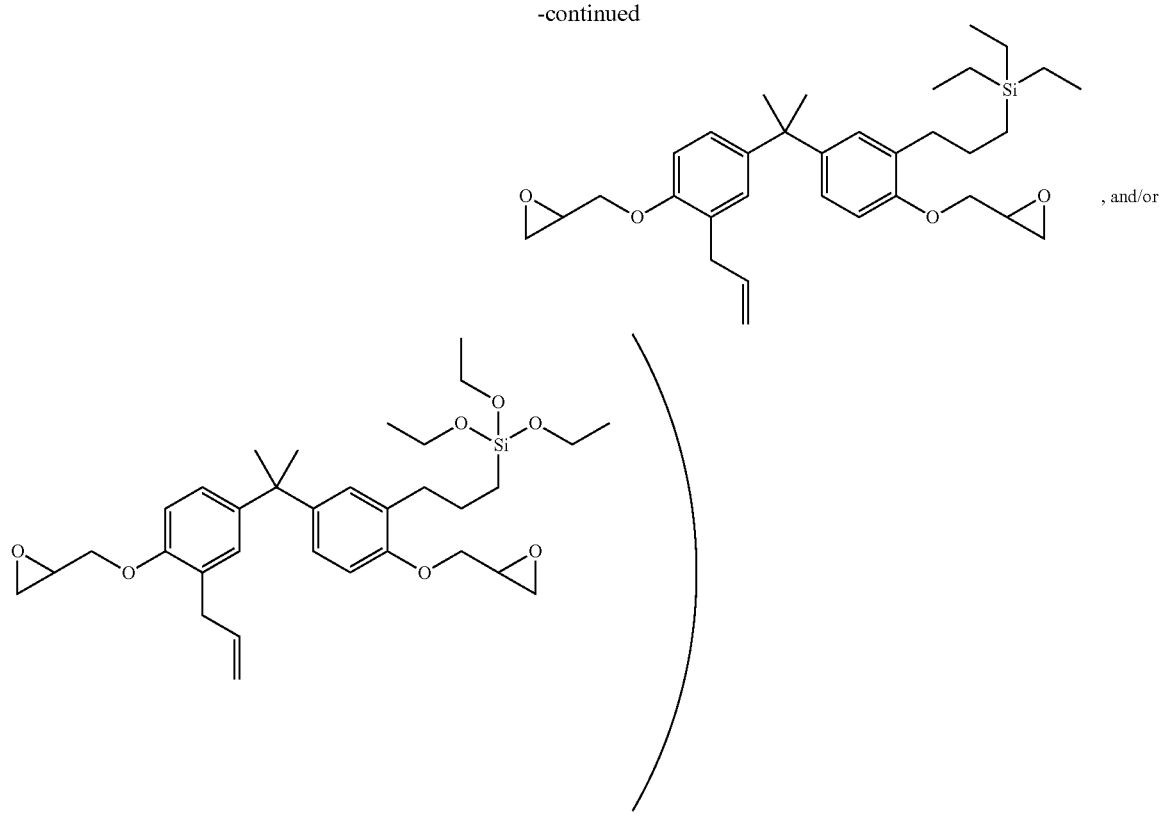

As can be seen in the above reaction formula, by-products as described within parentheses of the above reaction formula is formed together during the synthesis of a novel epoxy compound by a producing method according to an exemplary embodiment. A non-reactive starting material may also be existed in the mixture.

For reference, the starting material may also be synthesized by any method known in the art. For example, the starting material may be synthesized by the methods disclosed in Korean Patent Applications Nos. 2012-93320, 2013-11711, 2013-27308, 2013-35546, 2013-78347 and 2013-111473 applied for by the present applicant, the contents of which are included in this application by reference.

(2) Method 2

As described above, an epoxy compound according to an exemplary embodiment is produced by alkoxysilylation and non-reactive silylation of an alkenyl group of a starting material, for example, an epoxy compound with an epoxy group, and a hydroxy group or an amine group.

The starting material, for example, the epoxy compound with the epoxy group, and the hydroxy group or the amine group, may be a compound of Formulae AS2 to OS2.

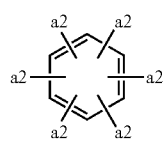

(AS2)

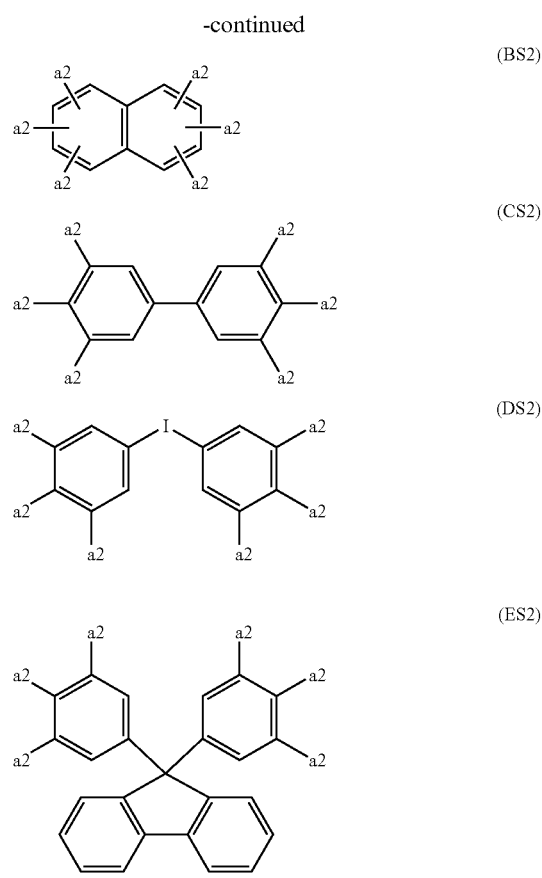

-continued (FS2)
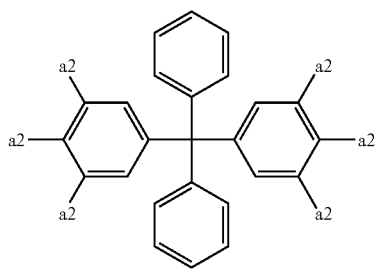

(GS2)
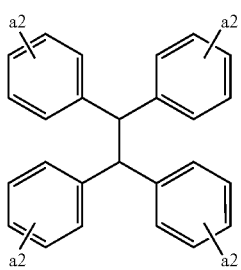

(HS2)
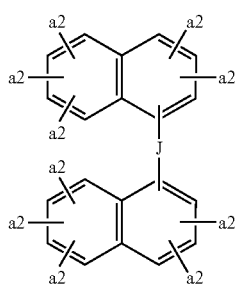

(IS2)
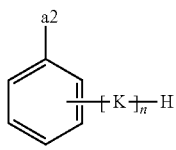

(JS2)
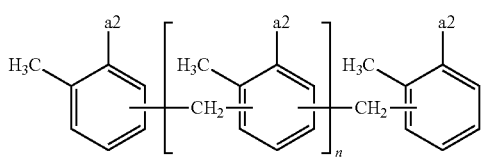

(KS2)
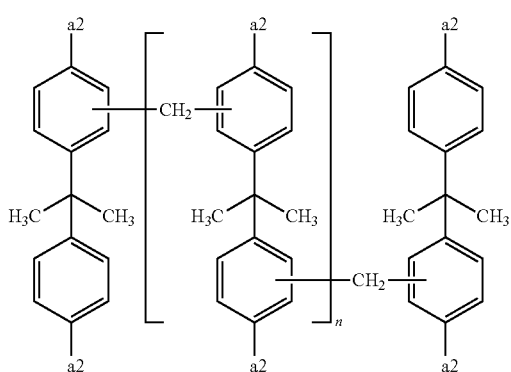

-continued (LS2)
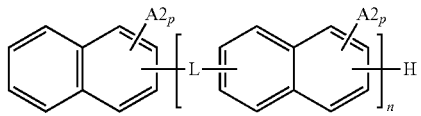

(MS2)
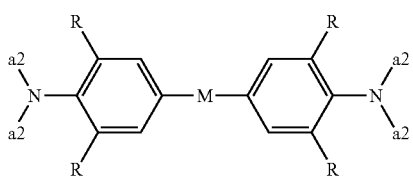

(NS2)
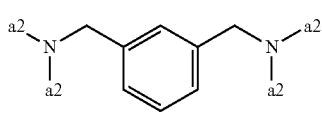

and (OS2)
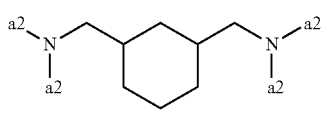

At least two of a plurality of substituents a2 of Formulae AS2 to FS2 are Formula E2, at least two thereof are hydroxy groups, and the remainder thereof may each be selected independently of hydrogen (H) and Formula A11.

At least two of a plurality of substituents a2 of Formulae GS2 to LS2 are Formula E1, at least two thereof are hydroxy groups, and the remainder thereof may be hydrogen (H).

At least two of a plurality of substituents a2 of Formulae MS2 to OS2 are Formula E2, and the remainder thereof may be hydrogen (H).

In Formula DS2, I is —CH$_2$—, —C(CH$_3$)$_2$—, —C(CF$_3$)$_2$—, —S—, —SO$_2$,

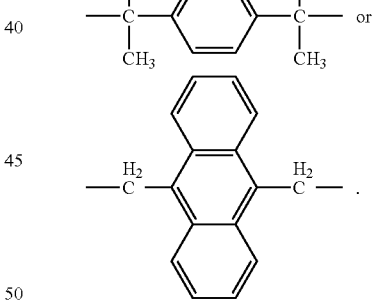 or

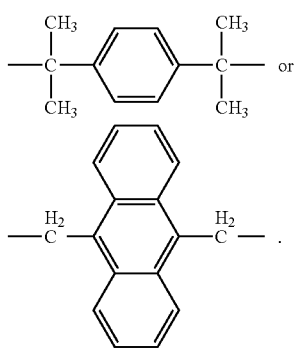.

In Formula HS2, J is direct linkage, —CH$_2$— or

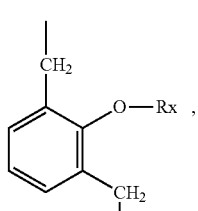
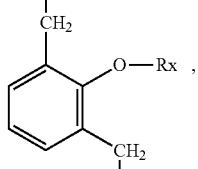

and Rx is hydrogen (H) or an alkyl group of C1-C3.

In Formula IS2, K is one selected from the group consisting of Formulae 1a2 to 1f2.

1a2

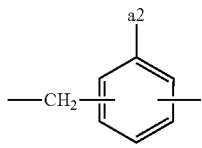

1b2

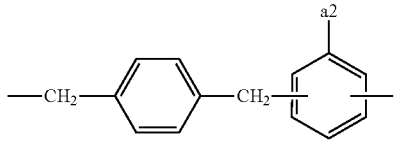

1c2

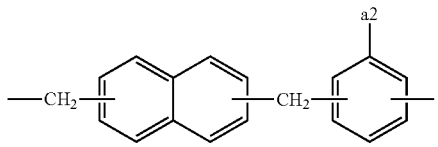

1d2

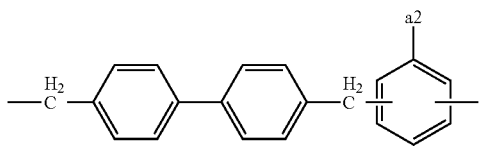

1e2

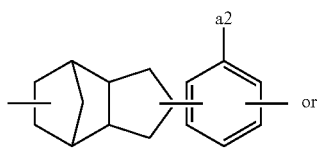

1f2

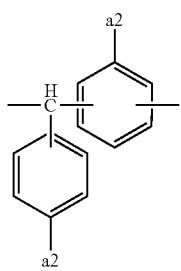

In Formula LS2, L is

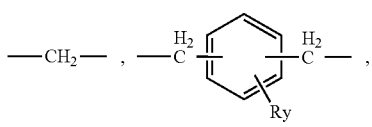

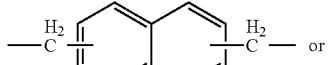

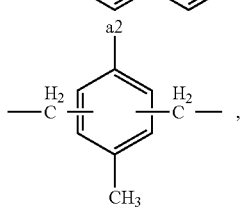

and in

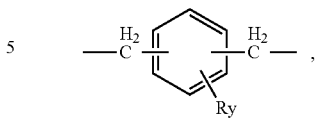

Ry is a linear or branched alkyl group of C1-C10.

In Formula MS2, M is —$CH_2$—, —$C(CH_3)_2$—, —$C(CF_3)_2$—, —S—, —$SO_2$—, or—

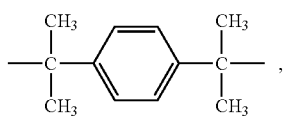

R is hydrogen (H) or an alkyl group of C1-C3.

In Formula IS2, when K is Formulae 2a to 2e, n is an integer of 3 or more, and when K is Formula 2f, n is an integer of 2 or more.

In Formulae JS2, n is an integer of 2 or more.

In Formulae KS2, n is an integer of 0 or more.

In Formula LS2, when L is

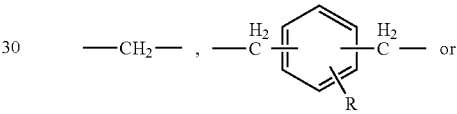

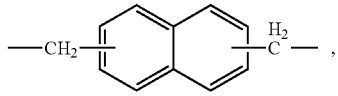

n is an integer of 3 or more, and when L is—

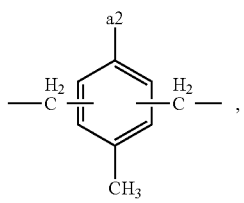

n is an integer of 2 or more.

In Formula LS2, p is 1 or 2. In Formulae IS2 to LS2, n is a maximum of 1,000.

In particular, the alkoxysilylation and non-reactive silylation of the hydroxy group or the amine group of the starting material is performed in the presence of optional solvent to obtain an epoxy compound with at least two epoxy groups, at least one alkoxysilyl group, and at least one non-reactive functional group according to an exemplary embodiment in the present disclosure, particularly, a non-reactive silyl group and an alkenyl group.

Since the reaction between the hydroxy group or the amine group of the starting material and alkoxysilane of Formula AS3 is performed in accordance with stoichiometry thereof, the reaction between the starting material and the alkoxysilane of Formula AS3 is performed using 0.1 to 5 equivalents of the alkoxysilane with respect to 1 equivalent of the hydroxy group or the amine group of the starting material in consideration of stomichiometry.

Particularly, when all of $R_1$ to $R_3$ of the alkoxysilane of Formula AS3 are methoxy groups, the reaction where 0.1 equivalent or more and less than 1 equivalent of the alkoxysilane of Formula AS3 is used with respect to 1 equivalent of the hydroxy group or the amine group of the starting material is more preferable. In the case of using below the concentration range of the alkoxysilane, a reaction rate of a methoxysilyl group and a degree of silylation of a final epoxy compound structure may be excessively low. In the case of using above the concentration range of the alkoxysilane, a concentration of the methoxysilyl group may be excessively high in the final epoxy compound structure.

OCN—(CH$_2$)$_m$—SiR$_1$R$_2$R$_3$    [Formula AS3]

In Formula AS3, at least one of $R_1$ to $R_3$ is an alkoxy group of C1 to C6, preferably an ethoxy group, the remainder thereof is an alkyl group of C1 to C10, the alkoxy group and the alkyl group may be linear or branched, may be cyclic or acyclic, and may or may not have an N, O, S, or P heteroatom. Moreover, m is an integer of 1 to 10, preferably an integer of 3 to 6.

In addition, since the reaction between the hydroxy group or the amine group of the starting material and non-reactive silane of Formula AS4 is performed in accordance with stoichiometry thereof, the reaction between the starting material and the non-reactive silane of Formula AS4 is performed using 0.1 to 5 equivalents of the non-reactive silane with respect to 1 equivalent of the hydroxy group or the amine group of the starting material in consideration of stoichiometry.

OCN—(CH$_2$)$_m$—SiR$_4$R$_5$R$_6$    [Formula AS4]

In Formula AS4, $R_4$ to $R_6$ are a non-reactive groups of an aliphatic, alicyclic, or aromatic moieties of 1 to 20 carbon atoms, the non-reactive group may be linear or branched, may be cyclic or acyclic, and may or may not have an N, O, S, or P heteroatom. Moreover, m is an integer of 1 to 10, preferably an integer of 3 to 6.

The reaction between the starting material, the alkoxysilane and the non-reactive silane may include (1) the reaction of the starting material with the alkoxysilane and the non-reactive silane, simultaneously and (2) reaction of the starting material with the alkoxysilane and then in-situ reaction of a reaction product with the non-reactive silane.

A reaction temperature and a reaction time of the starting material and the alkoxysilane may be changed depending on a type of a reacting material, and the reaction may be performed, for example, at a temperature of from −20° C. to 120° C. for 1 hour to 72 hours. By performing the reaction at the reaction temperature for the reaction time, a desired reaction may be completed.

The reaction related to a method of producing an epoxy compound according to an exemplary embodiment may be performed in the presence of a base as occasion demands. The reaction may proceed without a separate base, and in this case, a rate of the reaction is decreased, and the rate of the reaction may be increased using a base. The base used may include, for example, $K_2CO_3$, $Na_2CO_3$, $KHCO_3$, $NaHCO_3$, triethylamine, diisopropylethylamine, or the like, without limitation. These bases may be used alone or as a combination of two or more thereof. 1 to 5 equivalents of the base may be used with respect to 1 equivalent of the hydroxyl group or the amine group of the starting material in consideration of reaction efficiency.

Meanwhile, the solvent may be used optionally as occasion demands. For example, the solvent may not be used in a case in which viscosity of the reacting material at the reaction temperature is appropriate for carrying out the reaction without a separate solvent. Namely, when the viscosity of the reacting material is so low that mixing and stirring of the reacting material may be smoothly performed without a solvent, a separate solvent is not required. This may be easily determined by a person skilled in the art. In the case in which the solvent is used, any aprotic solvent may be used, as an available solvent, if able to dissolve the reacting material properly, not inducing any adverse influence to the reaction, and being easily removed after the reaction. For example, toluene, acetonitrile, tetrahydrofuran (THF), methyl ethyl ketone (MEK), dimethyl formamide (DMF), dimethyl sulfoxide (DMSO), methylene chloride (MC), or the like, may be used without limitation. These solvents may be used alone or as a mixture of two or more thereof. The use amount of the solvent may not be particularly limited, and an appropriate amount of the solvent may be used within a range suitable for sufficiently dissolving the reacting material and not adversely affecting the reaction. A person skilled in the art may select an appropriate amount of the solvent in consideration of the above-mentioned points.

A reaction scheme of a novel epoxy compound according to the present disclosure is as follows.

(a) In a case in which a starting material includes a hydroxyl group:

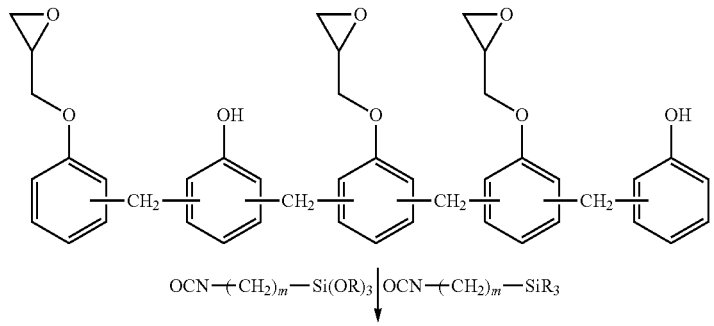

-continued
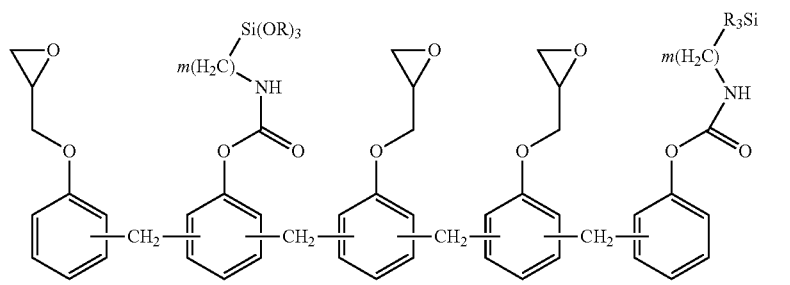
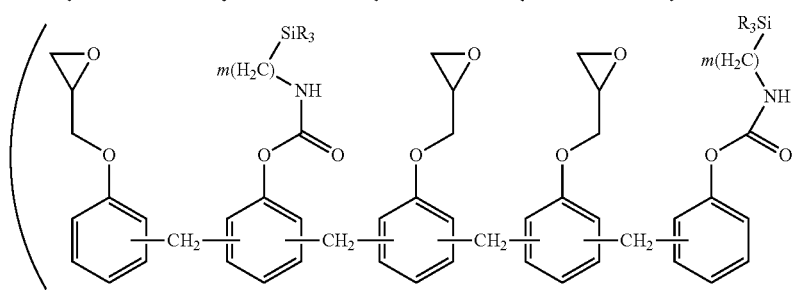
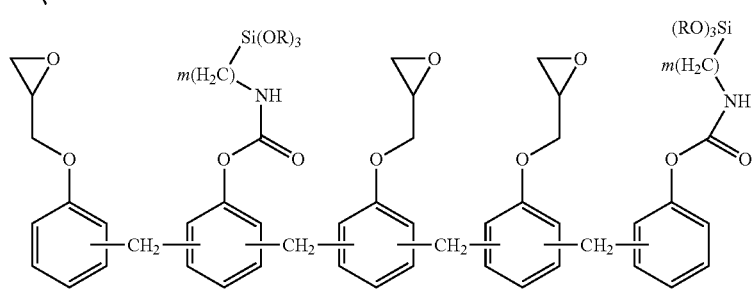
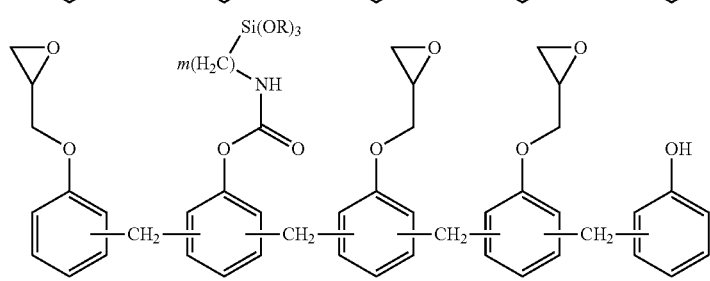
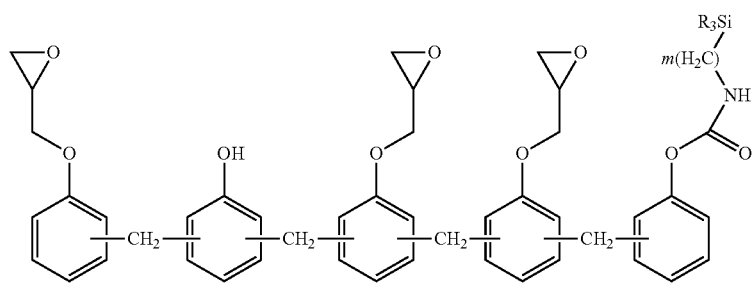
and/or
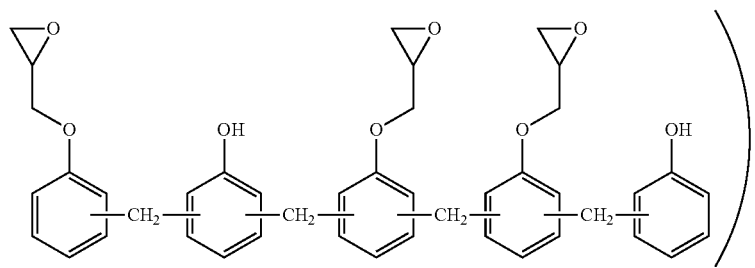

(b) In a case in which a starting material includes an amine group:

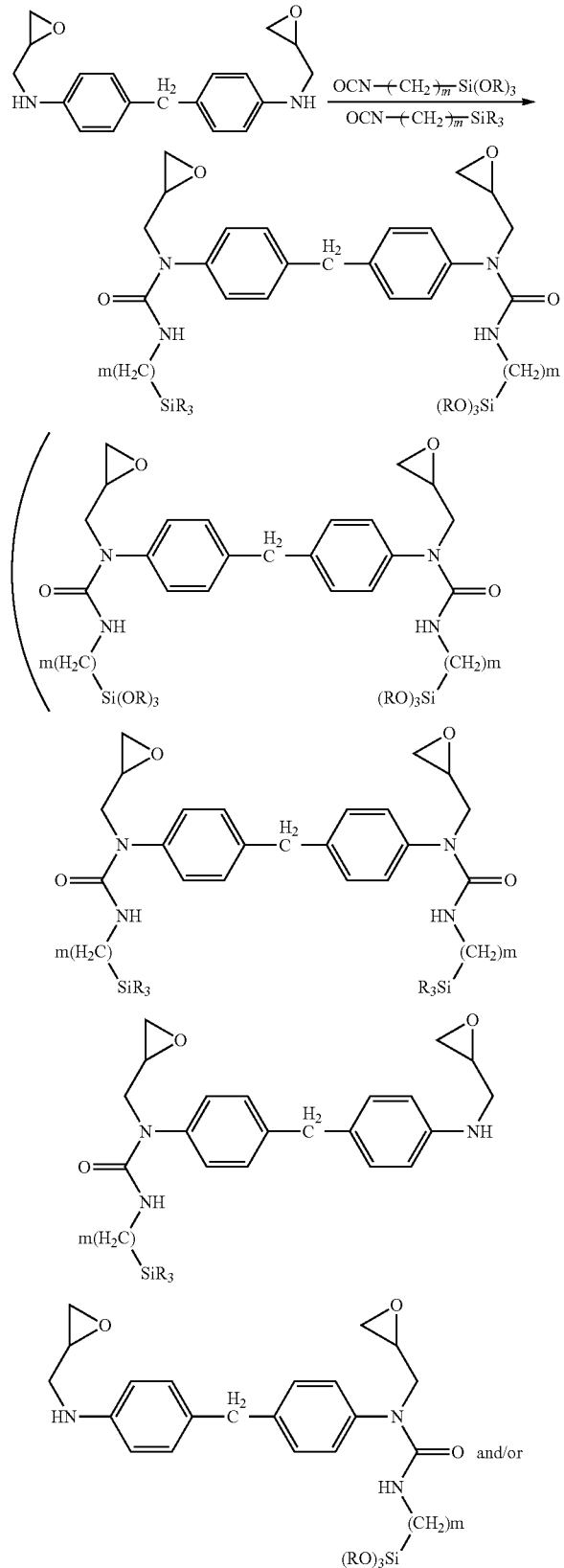

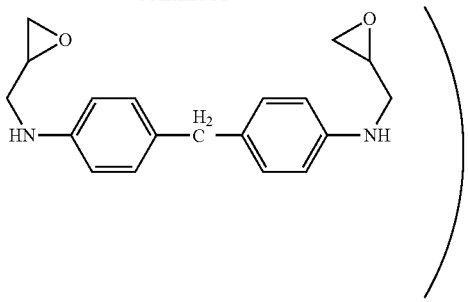

As can be seen in a reaction scheme above, during a process of producing a novel epoxy compound using a production method according to the present disclosure, a byproduct as illustrated in parentheses in the reaction scheme above is also generated. An unreacted starting material may also coexist.

The starting material may also be synthesized using a method known in the art. For example, the starting material may be synthesized using a method disclosed in Korean patent applications 2012-93320, 2013-11711, 2013-27308, 2013-35546, 2013-78347, and 2013-111473, applied for by the applicant. Details recorded in the patent applications are included in the present application for reference.

3. An Epoxy Composition According to another exemplary embodiment in the present disclosure, an epoxy composition including a novel epoxy compound provided according to an aspect in the present disclosure is provided.

Any composition provided in the present disclosure may be used in various applications, such as in an electronic material, for example, a semiconductor substrate such as an integrated circuit (IC) substrate or a build-up film, an encapsulating material (packaging material), an electronic part such as a printed circuit board, an adhesive, a paint, a composite material, or the like, without limitation. In addition, any composition provided in the present disclosure may be provided as a curable composition and/or a curable composition including an inorganic material.

An epoxy composition according to an aspect described above or later in the present disclosure may include any type and/or any formulation of epoxy compound known in the related art as long as novel epoxy compound according to an exemplary embodiment in the present disclosure, specifically at least one novel epoxy compound selected from a group consisting of formulae AF to OF according to an exemplary embodiment in the present disclosure is included therein. In this case, the type and the mixing ratio of a curing agent, a curing accelerator (catalyst), an inorganic material (filler) (for example, inorganic particles and/or a fiber), other general epoxy compounds, and other additives included in the epoxy composition are not limited.

Furthermore, in the art, the epoxy composition, a cured product and/or a composite may be used along with various types of general epoxy compounds depending on an application and/or purpose thereof in terms of controlling physical properties. Therefore, the epoxy compound according to an aspect in the present disclosure described above or later may include at least one novel epoxy compound (hereinafter, referred to as 'an epoxy compound in the present disclosure') selected from a group consisting of formulae AF to OF according to an exemplary embodiment in the present disclosure, and may include any type of epoxy compound (hereinafter, referred to as 'an epoxy compound in the prior art') known in the prior art, as the epoxy compound.

The epoxy compound of the prior art is not limited, but may be any epoxy compound known in the prior art. For example, the epoxy compound in the prior art may be at least one selected from a group consisting of a glycidyl ether-based epoxy compound, a glycidyl-based epoxy compound, a glycidyl amine-based epoxy compound, a glycidyl ester-based epoxy compound, a rubber-modified epoxy compound, an aliphatic polyglycidyl-based epoxy compound, and an aliphatic glycidyl amine-based epoxy compound. Furthermore, the epoxy compound in the prior art may be at least one selected from a group consisting of a glycidyl ether-based epoxy compound, a glycidyl-based epoxy compound, a glycidyl amine-based epoxy compound, a glycidyl ester-based epoxy compound, a rubber-modified epoxy compound, an aliphatic polyglycidyl-based epoxy compound, and an aliphatic glycidyl amine-based epoxy compound including bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, an alicyclic, an aliphatic, or a novolac unit, as a core structure.

For example, the epoxy compound in the prior art may be at least one selected from a group consisting of a glycidyl ether-based epoxy compound, a glycidyl-based epoxy compound, a glycidyl amine-based epoxy compound, and a glycidyl ester-based epoxy compound including bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, an alicyclic, an aliphatic, or, novolac unit as a core structure.

For example, any epoxy composition according to an exemplary embodiment in the present disclosure may include 1 wt % to 100 wt % of the epoxy compound in the present disclosure and 0 wt % to 99 wt % of the epoxy compound in the prior art; for example, 10 wt % to 100 wt % of the epoxy compound in the present disclosure and 0 wt % to 90 wt % of the epoxy compound in the prior art; for example, 30 wt % to 100 wt % of the epoxy compound in the present disclosure and 0 wt % to 70 wt % of the epoxy compound in the prior art; for example, 50 wt % to 100 wt % of the epoxy compound in the present disclosure and 0 wt % to 50 wt % of the epoxy compound in the prior art; for example, 10 wt % to less than 100 wt % of the epoxy compound in the present disclosure and greater than 0 wt % to 90 wt % of the epoxy compound in the prior art; for example, 30 wt % to less than 100 wt % of the epoxy compound in the present disclosure and greater than 0 wt % to 70 wt % of the epoxy compound in the prior art; and for example, 50 wt % to less than 100 wt % of the epoxy compound in the present disclosure and greater than 0 wt % to 50 wt % of the epoxy compound in the prior art, based on the total weight of the epoxy compound, but is not limited thereto.

Furthermore, any epoxy composition according to an aspect in the present disclosure described above or later may also further include an inorganic material (filler) (for example, inorganic particles and/or a fiber).

Any inorganic particles known for being used to reinforce physical properties of an organic resin in the related art may be used. Examples of the inorganic particles may include, without limitation, at least one selected from a group consisting of at least one metal oxide selected from a group consisting of silica (including, for example, fused silica and crystalline silica), zirconia, titania, alumina, silicon nitride, and aluminum nitride, and silsesquioxane. The inorganic particles may be used alone, or as a mixture of two or more thereof.

In a case in which a particularly large amount of silica is mixed, the fused silica is required to be used. The fused silica may have either of a cataclastic shape or a spherical shape. However, the spherical shape is required to be used to increase a mixing ratio of the fused silica and to suppress the melt viscosity of a forming material from being increased.

The inorganic particles having a particle size of 0.5 nm to several tens of μm (for example, from 50 μm to 100 μm) may be used, without limitation, in consideration of an application of a composite, in detail, dispersibility of the inorganic particles, and the like. Since the inorganic particles are dispersed in the epoxy compound, and the dispersibility thereof is different according to a particle size, inorganic particles having the above-described sizes are required to be used in combination. In addition, a distribution range of particle size of the inorganic particles to be mixed is required to be increased to increase an amount of inorganic particles in a mixture.

In the epoxy composition according to an exemplary embodiment in the present disclosure, an amount of the inorganic particles added with respect to the epoxy compound may be appropriately controlled in accordance of CTE decrease of epoxy composite, appropriate viscosity required in an application of the epoxy composition, and usage thereof. For example, an amount of the inorganic particles may be 5 wt % to 95 wt %, for example, 5 wt % to 90 wt %, for example 10 wt % to 90 wt %, for example, 30 wt % to 95 wt %, for example, 30 wt % to 90 wt %, for example, 5 wt % to 60 wt %, for example, 10 wt % to 50 wt % based on the total weight of a solids content of the epoxy composition (meanwhile, based on the total weight of the epoxy cured product, in the case of an epoxy cured product).

In more detail, in an exemplary embodiment, in a case in which the epoxy composition is used as a semiconductor encapsulating material, or the like, an amount of the inorganic particles may be, for example, 30 wt % to 95 wt %, for example, 30 wt % to 90 wt %, without limitation, in consideration of a CTE and processability, based on the total weight of a solids content of the epoxy composition (meanwhile, based on the total weight of the epoxy cured product, in the case of an epoxy cured product). In an exemplary embodiment, in a case in which the epoxy composition is used as a semiconductor substrate, or the like, the amount of the inorganic particles may be, for example, 5 wt % to 85 wt %, for example, 10 wt % to 80 wt %, in consideration of the CTE value and strength and the like of a substrate, based on the total weight of a solids content of the epoxy composition (meanwhile, based on the total weight of the epoxy cured product, in the case of the epoxy cured product).

Meanwhile, in a case in which a fiber is used as an inorganic material, since a composite is commonly made in such a manner that the fiber is impregnated with the epoxy composition, a size of fiber, and the like, is not particularly limited. In addition, any type and dimensions of a fiber commonly used in the art, may be used.

Any commonly used fibers used for the improvement of physical properties of an organic resin cured product in the related art may be used without limitation. In detail, a glass fiber, an organic fiber, or a mixture thereof may be used. In addition, the term 'glass fiber' used in the present application may include a woven glass fiber fabric, a non-woven glass fiber fabric, or the like as well as a glass fiber. Examples of the glass fiber may be, without limitation, an E-glass fiber, a T-glass fiber, an S-glass fiber, an NE-glass fiber, a D-glass fiber, a quartz glass fiber, or the like. For example, an E or T glass fiber may be included therein. An organic fiber may be, without limitation, one selected from a group consisting of a liquid crystal polyester fiber, a polyethyleneterephthalate fiber, a wholly aromatic fiber, a polybenzoxazole fiber, a nylon fiber, a polyethylene naphthalate fiber, a polypropylene fiber, a polyether sulfone fiber, a polyvinylidene fluoride fiber, a polyethylene sulfide fiber, a polyether ether ketone fiber. These fibers may be used alone or as a combination of two or more thereof.

In the epoxy composition according to an aspect in the present disclosure, for example, in a glass fiber composite, an amount of a fiber may be 10 wt % to 90 wt %, for example, 30 wt % to 70 wt %, in addition, for example, 35 wt % to 70 wt % based on the total weight of a cured product. Thus, a content of a resin may be 10 wt % to 90 wt %, for example, 30 wt % to 70 wt %, in addition, for example, 35 wt % to 70 wt %. The amount of the fiber is required to be within the above-described range in consideration of an increase in thermal resistance and a processability aspect. Meanwhile, in the epoxy composition, the cured product, or the like, including a fiber, a solids content part excluding the fiber from the total solids content is commonly referred to as a resin content (R/C).

Furthermore, in the epoxy composition including the fiber according to an aspect in the present disclosure, inorganic particles may be additionally included as occasion demands. In this case, the inorganic particles may be mixed with the epoxy composition in an amount of 1 wt % to 80 wt % based on the weight of a resin content in consideration of improvement of physical properties and processability. In this case, the type of the inorganic particles which may be used, is not specifically limited, and any inorganic particles known in the art may be used. For example, the type of the above-described inorganic particles may be used.

In the meantime, in the epoxy composition of an aspect in the present disclosure described above or later, a curing agent may be additionally included.

Any curing agent commonly known as a curing agent used for an epoxy compound may be used as the curing agent without limitation, and for example, an amine, a polyphenol, an acid anhydride, or the like, may be used.

In more detail, an aliphatic amine, an alicyclic amine, an aromatic amine, other amines and a modified polyamine may be used as an amine curing agent without limitation. In addition, an amine compound including two or more primary amine groups may be used. Specific examples of the amine curing agent may include at least one aromatic amine selected from a group consisting of 4,4'-dimethylaniline (diamino diphenyl methane, DAM or DDM), diamino diphenyl sulfone (DDS), and m-phenylene diamine, at least one aliphatic amine selected from a group consisting of diethylene triamine (DETA), diethylene tetramine, triethylene tetramine (TETA), m-xylene diamine (MXDA), methane diamine, (MDA), N,N'-diethylenediamine (N,N'-DEDA), tetraethylenepentaamine (TEPA), and hexamethylenediamine, at least one alicyclic amine selected from a group consisting of isophorone diamine (IPDI), N-aminoethyl piperazine (AEP), bis (4-amino 3-methylcyclohexyl) methane (larominc 260), other amines such as dicyandiamide (DICY), or the like, and a modified amine such as a polyamide-based compound, an epoxide-based compound, or the like.

Examples of a polyphenol curing agent may include, without limitation, a phenol novolac resin, a cresol novolac resin, a bisphenol A novolac resin, a xylene novolac resin, a triphenyl novolac resin, a biphenyl novolac resin, a dicyclopentadiene novolac resin, a naphthalene novolac resin, or the like.

Examples of an acid anhydride-based curing agent may include, without limitation, an aliphatic acid anhydride such as dodecenyl succinic anhydride (DDSA), poly azelaic poly anhydride, or the like, an alicyclic acid anhydride such as hexahydrophthalic anhydride (HHPA), methyl tetrahydrophthalic anhydride (MeTHPA), methylnadic anhydride (MNA), or the like, an aromatic acid anhydride such as trimellitic anhydride (TMA), pyromellitic acid dianhydride (PMDA), benzophenonetetracarboxylic dianhydride (BTDA), or the like, and a halogen-based acid anhydride such as tetrabromophthalic anhydride (TBPA), chlorendic anhydride, or the like.

In general, a degree of curing of an epoxy composite may be controlled by the reaction degree of the curing agent and the epoxy group. According to a range of a target degree of curing, an amount of the curing agent may be controlled based on a concentration of the epoxy group of the epoxy compound. For example, when an amine curing agent is used, a ratio of an epoxy equivalent/amine equivalent is required to be controlled to be 0.5 to 2.0, or for example, 0.8 to 1.5 in an equivalent reaction of the curing agent and the epoxy group.

A description of a mixing amount of the curing agent was provided using the amine curing agent as an example. However, a polyphenol curing agent, an acid anhydride-based curing agent, and any curing agents not separately described in the present application but used for curing an epoxy compound may be used by mixing an appropriate stoichiometric amount of the epoxy functional group and the reactive functional group of the curing agent based on a concentration of the total epoxy group in the epoxy composition according to the required range of the degree of curing. The above-described elements are commonly known in the art.

In addition, an imidazole described below is commonly used as a curing accelerator, but may also be used as a curing agent alone. In a case in which the imidazole is used as a curing agent, 0.1 phr to 10 phr of the imidazole may be used with respect to the epoxy compound.

An optional curing accelerator (curing catalyst) may be additionally included as occasion demands to promote a curing reaction, in the epoxy composition according to an aspect in the present disclosure described above or later. In addition, any catalysts known for being commonly used for curing the epoxy composition in the art may be used as a curing accelerator (curing catalyst). The curing accelerator, without limitation, for example, an imidazole, a tertiary amine, quaternary ammonium, an organic acid salt, a Lewis acid, a phosphorus compound, or the like, may be used.

In more detail, for example, an imidazole such as a dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, 2-heptadecylimidazole (2HDI), or the like; a tertiary amine compound, such as benzyl dimethyl amine (BDMA), tris dimethylaminomethyl phenol (DMP-30), diazacycloundecene (DBU), triethylenediamine, or the like; a quaternary ammonium salt, such as tetrabutylammonium bromide, or the like; an organic acid salt of diazabicycloundecene (DBU); a phosphorus-based compound such as triphenyl phosphine, phosphoric acid ester, or the like, and a Lewis acid such as $BF_3$-monoethylamine ($BF_3$-MEA), or the like, may be used without limitation. These curing accelerators, latent due to microcapsule coating thereof, a complex salt formation, or the like, may be used. These compounds may be used alone or as a mixture of two or more thereof according to curing conditions.

An amount of mixing the curing accelerator may be used in a mixing amount commonly used in the art without limitation.

For example, the amount of mixing the curing accelerator may be 0.1 phr to 10 phr (parts per hundred resin, parts by weight based on 100 parts by weight of an epoxy compound), for example, 0.2 phr to 5 phr based on the epoxy compound. The above-described amount of the curing accelerator is required to be used in consideration of a curing reaction accelerating effect and curing reaction rate controlling aspect. Through using the above-described range of the amount of mixing the curing accelerator, curing may be rapidly carried out, and an improvement of throughput may be expected.

In the epoxy composition, other additives such as a releasing agent, a surface treating agent, a flame retardant, a plasticizer, bactericides, a leveling agent, a defoaming agent, a colorant, a stabilizer, a coupling agent, a viscosity controlling agent, a diluent, a rubber, a thermoplastic resin, or the like, may be mixed to commonly control physical properties of the epoxy composition within a range not damaging physical properties of the epoxy composition, as occasion demands.

For example, in order to improve flexibility in any compositions according to an exemplary embodiment, a rubber and/or a thermoplastic resin may be added to the epoxy composition according to an aspect. The thermoplastic resin and a rubber-modified epoxy resin, commonly known in the art, may be used. As a rubber, any rubber known in the art may be used as long as the rubber is not dissolved by a solvent used in the composition and maintains a dispersed state in the composition. The type of the rubber may include, for example, an acrylonitrile butadiene rubber, a butadiene rubber, an acryl rubber, core-shell type rubber particles, cross-linked acrylonitrile butadiene rubber particles, cross-linked styrene butadiene rubber particles, acryl rubber particles, and the like, without limitation. These materials may be used alone or as a combination of two or more thereof. In the case of using a rubber particle, an average particle diameter is required to be from 0.005 µm to 1 µm, and in more detail, from 0.2 µm to 0.6 µm in consideration of improvement of physical properties. The rubber particles may be mixed in, for example, an amount of 0.5 wt % to 10 wt % thereof in consideration of physical properties based on weight of a solids content of the epoxy composition.

As a thermoplastic resin, a phenoxy resin, a polyvinyl acetal resin, a polyimide resin, a polyamideimide resin, a polyether sulfone resin, a polysulfone resin, or the like may be used without limitation. These materials may used alone or as a mixture of two or more thereof. The thermoplastic resin may be mixed in, for example, 0.5 wt % to 60 wt %, and in more detail, 3 wt % to 50 wt % based on weight of a solids content of the epoxy composition in consideration of physical properties.

As described above, the term "epoxy composition" used in the present application will be understood to include an epoxy compound according to an exemplary embodiment in the present disclosure, and other constituents composing the epoxy composition as occasion demands, for example, other additives mixed as occasion demands in the art other than an optional curing agent, a curing accelerator (catalyst), an inorganic material (filler) (for example, inorganic particles and/or a fiber), other general epoxy compounds, and a solvent. Thus, generally, in the epoxy composition, the solvent may optionally be used to appropriately control a solids content of the epoxy composition and/or viscosity thereof in consideration of processability and the like of the epoxy composition. Meanwhile, the term "total weight of solids content of epoxy composition" used in the present disclosure refers to total weight of a component except the solvent in components composing the epoxy composition.

Any epoxy compositions provided according to an aspect in the present disclosure may be used as a composition for an electronic material. The electronic material may include, without limitation, for example, a substrate for a semiconductor, a film, a prepreg, a laminated plate in which a metal layer is disposed on a base formed using the composition according to an exemplary embodiment in the present disclosure, an encapsulating material (packaging material), an electronic component such as a printed circuit board, or the like. In addition, the epoxy composition may be used in various applications such as in an adhesive, a paint, a composite material, and the like. According to another exemplary embodiment in the present disclosure, an electronic material including or formed using any compositions including the epoxy compound according to an exemplary embodiment in the present disclosure, is provided. Furthermore, a semiconductor device including, or necessarily formed using, or formed using the electronic material, is provided. In detail, the semiconductor device may be a semiconductor device including a printed circuit board (for example, a printed circuit board on which a semiconductor element is mounted) and/or a semiconductor device including a semiconductor packaging material, including, or necessarily formed using, or formed using the composition including the epoxy compound according to an exemplary embodiment in the present disclosure. In addition, a cured product, an adhesive, a paint, or a composite material including, or necessarily formed using, or formed using any epoxy compositions provided in an aspect in the present disclosure, may be provided.

According to another exemplary embodiment in the present disclosure, a cured product including, or necessarily formed using, or formed using the epoxy composition according to an exemplary embodiment in the present disclosure, provided in an aspect in the present disclosure, may be provided. In a case in which the epoxy composition provided in an aspect in the present disclosure, is practically used, for example, when the epoxy composition is practically used as an electronic material or the like, the epoxy composition is used as a cured product. In the art, the cured product formed of the composition including the epoxy compound and the filler which is an inorganic component, may be commonly referred to as a composite.

The epoxy compound provided in an exemplary embodiment in the present disclosure described above may have excellent thermal resistance properties in a composite and/or excellent flame retardant in a cured product.

In detail, the composite may exhibit a relatively low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. Physical properties of the composite are improved as a CTE value is reduced, whereby a lower limit value of a CTE is not particularly limited.

For example, a composite including the any epoxy compound according to an exemplary embodiment in the present disclosure, a glass fiber, for example, an E-glass and/or a T-glass glass fiber as an inorganic material having a resin content of 30 wt % to 60 wt % (the resin content may include or may not include inorganic particles), may exhibit a CTE of, for example, 10 ppm/° C. or less, for example, 8 ppm/° C. or less, for example, 6 ppm/° C. or less, for example, 4 ppm/° C. or less.

In addition, for example, a composite including any epoxy compound according to an exemplary embodiment in the present disclosure as an epoxy compound, and inorganic particles as an inorganic material, for example, 60 wt % to 80 wt %, for example, 70 wt % to 80 wt % of silica particles, may exhibit a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (cured product including an inorganic material) according to an exemplary embodiment in the present disclosure, may be higher than 100° C., for example, 130° C. or higher, in addition, for example, 250° C. or higher. Otherwise, the composite may be Tg-less. Physical properties of the composite are improved as a Tg value is higher, whereby an upper limit value of Tg is not particularly limited.

In the meantime, the cured product (cured product not including an inorganic material) of the epoxy compound according to an exemplary embodiment may have a CTE of 50 ppm/° C. to 150 ppm/° C.

In the present application, the values delimited by the range include the lower limit value, the upper limit value, any subranges in the range, and all numerals included in the range, unless otherwise specifically stated. For example, C1 to C10 will be understood to include all of C1, C2, C3, C4, C5, C6, C7, C8, C9, and C10. In addition, in a case in which the lower limit value or the upper limit value of the numerical range is not defined, it will be understood that a smaller or larger value may provide the better properties. In addition, it would be understood that the limit is not defined and any values may be included. For example, a CTE of 4 ppm/° C. or less will be understood to include all values in the range such as the CTE of 4, 3.5, 3, 2.7, 2, 1.4, 1, 0.5 ppm/° C., and the like.

Hereinafter, the present disclosure will be described in detail through examples. The following examples are for illustrating the present disclosure and are not intended to limit the present disclosure.

Synthetic Example 1: Synthesis of a Bisphenol A-Based Epoxy Compound Including an Ethoxysilyl Group and an Ethylsilyl Group (Si(OEt)$_3$:Si(Et)$_3$=3:1)

To a 500 ml flask, 17.17 g of bisphenol A epoxy with an allyl group (Structural formula 1), 11.01 ml of triethoxysilane, 6.54 ml of triethylsilane, 185 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 1]

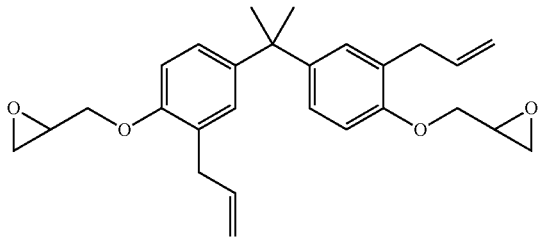

$^1$H NMR (400 MHz, CDCl$_3$): δ=0.42-0.53 (m, 10H), 0.84 (t, J=8.0 Hz, 4.5H), 1.20 (t, J=7.0 Hz, 13.5H), 1.60 (s, 6H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 6.70 (d, J=7.6 Hz, 2H), 6.94 (dd, J=2.8 Hz, 2H), 6.99 (d, J=7.6 Hz, 2H)

Synthetic Example 2: Synthesis of a Bisphenol A-Based Epoxy Compound Including an Ethoxysilyl Group, an Ethylsilyl Group, and an Allyl Group (Si(OEt)$_3$:Si(Et)$_3$:Allyl=2:1:1)

To a 500 ml flask, 17.17 g of bisphenol A epoxy with an allyl group (Structural formula 1), 7.34 ml of triethoxysilane, 3.27 ml of triethylsilane, 185 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.42-0.53 (m, 9H), 0.84 (t, J=8.0 Hz, 4.5H), 1.20 (t, J=7.0 Hz, 9H), 1.60 (s, 6H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 4H), 3.97 (dd, J=5.2 Hz, 2H), 4.14 (dd, J=3.2 Hz, 2H), 4.93-5.01 (m, 1H), 5.80-5.95 (m, 0.5H), 6.59-6.71 (m, 0.4H), 6.87-7.04 (m, 5.6H)

Synthetic Example 3: Synthesis of a Bisphenol A-Based Epoxy Compound Including an Ethoxysilyl Group and an Allyl Group (Si(OEt)$_3$:Allyl=1:1)

To a 500 ml flask, 5.31 g of bisphenol A epoxy with an allyl group (Structural formula 1), 2.33 ml of triethoxysilane, 28 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 2H), 1.20 (t, J=7.0 Hz, 9H), 1.60 (s, 6H), 1.62-1.72 (m, 2H), 2.61 (t, J=7.6 Hz, 2H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 4.93-5.01 (m, 2H), 5.80-5.95 (m, 1H), 6.87-7.04 (m, 6H)

Synthetic Example 4: Synthesis of a Bisphenol A-Based Epoxy Compound Including an Ethoxysilyl Group and an Allyl Group (Si(OEt)$_3$:Allyl=1:1.5)

To a 500 ml flask, 10.66 g of bisphenol A epoxy with an allyl group (Structural formula 1), 3.59 ml of triethoxysilane, 58 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 1.6H), 1.20 (t, J=7.0 Hz, 7.2H), 1.60 (s, 6H), 1.62-1.72 (m, 1.6H), 2.61 (t, J=7.6 Hz, 1.6H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 4.8H), 3.97 (dd, J=5.2 Hz, 2H), 4.14 (dd, J=3.2 Hz, 2H), 4.93-5.01 (m, 2.4H), 5.80-5.95 (m, 1.2H), 6.87-7.04 (m, 6H)

Synthetic Example 5: Synthesis of a Bisphenol A-Based Epoxy Compound Including an Ethoxysilyl Group and an Allyl Group (Si(OEt)$_3$:Allyl=1:0.67)

To a 500 ml flask, 7.11 g of bisphenol A epoxy with an allyl group (Structural formula 1), 3.90 ml of triethoxysilane, 45 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 2.4H), 1.20 (t, J=7.0 Hz, 10.8H), 1.60 (s, 6H), 1.62-1.72 (m, 2.4H), 2.61 (t, J=7.6 Hz, 2.4H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 7.2H), 3.97 (dd, J=5.2 Hz, 2H), 4.14 (dd, J=3.2 Hz, 2H), 4.93-5.01 (m, 1.6H), 5.80-5.95 (m, 0.8H), 6.87-7.04 (m, 6H)

Synthetic Example 6: Synthesis of a Bisphenol A-Based Epoxy Compound Including an Ethoxysilyl Group and an Allyl Group (Si(OEt)$_3$:Allyl=1:0.33)

To a 500 ml flask, 12.68 g of bisphenol A epoxy with an allyl group (Structural formula 1), 8.34 ml of triethoxysilane, 102 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 3H), 1.20 (t, J=7.0 Hz, 13.5H), 1.60 (s, 6H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 9H), 3.97 (dd, J=5.2 Hz, 2H), 4.14 (dd, J=3.2 Hz, 2H), 4.93-5.01 (m, 1H), 5.80-5.95 (m, 0.5H), 6.87-7.04 (m, 6H)

Synthetic Example 7: Synthesis of a Bisphenol A-Based Epoxy Compound Including a Methoxysilyl Group and an Allyl Group (Si(OMe)$_3$:Allyl=1:9)

To a 500 ml flask, 40.09 g of bisphenolAepoxywithan allyl group (Structural formula 1), 2.74 ml of trimethoxysilane, 218 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, DMSO): δ=0.54 (t, J=8.0 Hz, 0.4H), 1.55 (s, 6.4H), 2.49-2.51 (m, 0.4H), 2.70 (dd, J=2.6 Hz, 2H), 2.82 (dd, J=4.2 Hz, 2H), 3.26-3.32 (m, 5.4H), 3.42 (s, 1.8H), 3.84 (dd, J=5.4 Hz, 2H), 4.26 (dd, J=3.2 Hz, 2H), 4.94-5.01 (m, 3.6H), 5.83-5.95 (m, 1.8H), 6.83-7.02 (m, 6H)

Synthetic Example 8: Synthesis of a Bisphenol A-Based Epoxy Compound Including a Methoxysilyl Group and an Allyl Group (Si(OMe)$_3$:Allyl=1:4)

To a 500 ml flask, 11.10 g of bisphenol A epoxy with an allyl group (Structural formula 1), 11.86 ml of trimethoxysilane, 59 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, DMSO): δ=0.54 (t, J=8.0 Hz, 0.8H), 1.55 (s, 6.8H), 2.49-2.51 (m, 0.8H), 2.70 (dd, J=2.6 Hz, 2H), 2.82 (dd, J=4.2 Hz, 2H), 3.26-3.32 (m, 4.8H), 3.42 (s, 3.6H), 3.84 (dd, J=5.4 Hz, 2H), 4.26 (dd, J=3.2 Hz, 2H), 4.94-5.01 (m, 3.2H), 5.83-5.95 (m, 1.6H), 6.83-7.02 (m, 6H)

Synthetic Example 9: Synthesis of a Bisphenol A-Based Epoxy Compound Including an Ethoxysilyl Group, a Methoxysilyl Group, and an Allyl Group (Si(OEt)$_3$:Si(OMe)$_3$:Allyl=1:1:8)

To a 500 ml flask, 40.02 g of bisphenol A epoxy with an allyl group (Structural formula 1), 3.68 ml of triethoxysilane, 2.73 ml of trimethoxysilane, 218 mg of a platinum oxide, and 100 ml of toluene were added and mixed, followed by stirring at 850C for 24 hours under argon gas. After a reaction, the obtained crude product was celite-filtered, and a solvent was removed using an evaporator to yield a final epoxy. NMR data of the obtained final product are as follows.

$^1$H NMR (400 MHz, DMSO): δ=0.50-0.56 (m, 0.8H), 1.04-1.13 (m, 1.8H), 1.55 (s, 6.8H), 2.49-2.51 (m, 0.8H), 2.70 (dd, J=2.6 Hz, 2H), 2.82 (dd, J=4.2 Hz, 2H), 3.26-3.32 (m, 4.8H), 3.42 (t, J=4.0 Hz, 1.8H), 3.84 (dd, J=5.4 Hz, 2H), 4.26 (dd, J=3.2 Hz, 2H), 4.94-5.01 (m, 3.2H), 5.83-5.95 (m, 1.6H), 6.83-7.02 (m, 6H)

Synthetic Example 10: Synthesis of a Naphthalene-Based Epoxy Compound Including an Ethoxysilyl Group and an Ethylsilyl Group (Si(OEt)$_3$:Si(Et)$_3$=3:1)

To a 500 ml flask, 18.66 g of naphthalene epoxy with an allyl group (Structural formula 2), 13.32 ml of triethoxysilane, 8.45 ml of triethylsilane, 239 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 2]

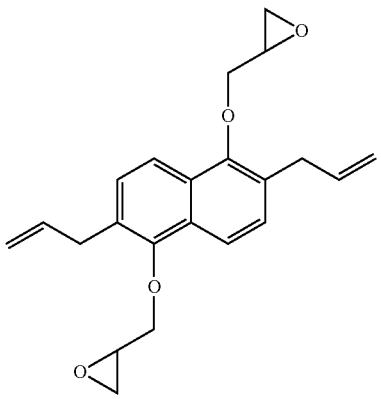

$^1$H NMR (400 MHz, CDCl$_3$): δ=0.64-0.72 (m, 10H), 0.84 (t, J=8.0 Hz, 4.5H), 1.20 (t, J=7.0 Hz, 13.5H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 7.28 (d, J=8.5 Hz, 2H), 7.75 (d, J=8.5 Hz, 2H).

Synthetic Example 11: Synthesis of a Naphthalene-Based Epoxy Compound Including an Ethoxysilyl Group, an Ethylsilyl Group, and an Allyl Group (Si(OEt)$_3$:Si(Et)$_3$:Allyl=2:1:1)

To a 500 ml flask, 18.66 g of naphthalene epoxy with an allyl group (Structural formula 2), 9.51 ml of triethoxysilane, 4.23 ml of triethylsilane, 239 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.72 (m, 7.5H), 0.84 (t, J=8.0 Hz, 2.3H), 1.20 (t, J=7.0 Hz, 9H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 4.5H), 3.97 (dd, J=5.2 Hz, 2H), 4.14 (dd, J=3.2 Hz, 2H), 5.07-5.12 (m, 1H), 5.98-6.08 (m, 0.5H), 7.28 (d, J=8.5 Hz, 2H), 7.75 (d, J=8.5 Hz, 2H).

Synthetic Example 12: Synthesis of a Naphthalene-Based Epoxy Compound Including an Ethoxysilyl Group and an Allyl Group (Si(OEt)$_3$:Allyl=1:1)

To a 500 ml flask, 18.39 g of naphthalene epoxy with an allyl group (Structural formula 2), 9.63 ml of triethoxysilane, 119 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 2H), 1.20 (t, J=7.0 Hz, 9H), 1.62-1.72 (m, 2H), 2.61 (t, J=7.6 Hz, 2H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 5.07-5.12 (m, 2H), 5.98-6.08 (m, 1H), 7.28-7.35 (m, 2H), 7.75-7.89 (m, 2H).

Synthetic Example 13: Synthesis of a Naphthalene-Based Epoxy Compound Including an Ethoxysilyl Group and an Allyl Group (Si(OEt)$_3$:Allyl=1:3)

To a 500 ml flask, 10.21 g of naphthalene epoxy with an allyl group (Structural formula 2), 2.67 ml of triethoxysilane, 66 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 1H), 1.20 (t, J=7.0 Hz, 4.5H), 1.62-1.72 (m, 1H), 2.61 (t, J=7.6 Hz, 1H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 3H), 3.97 (dd, J=5.2 Hz, 2H), 4.14 (dd, J=3.2 Hz, 2H), 5.07-5.12 (m, 3H), 5.98-6.08 (m, 1.5H), 7.28-7.35 (m, 2H), 7.75-7.89 (m, 2H).

Synthetic Example 14: Synthesis of a Naphthalene-Based Epoxy Compound Including an Ethoxysilyl Group and an Allyl Group (Si(OEt)$_3$:Allyl=1:0.33)

To a 500 ml flask, 12.51 g of naphthalene epoxy with g an allyl group (Structural formula 2), 9.82 ml of triethoxysilane, 121 mg of a platinum oxide, and 100 ml of toluene were added and mixed, followed by stirring at 85° C. for 24 hours under argon gas. After a reaction, the obtained crude product was celite-filtered, a solvent was removed using an evaporator to yield a final epoxy. NMR data of the obtained final product are as follows.

$^1$H NMR (400 MHz, CDCl$_3$): δ=0.64-0.69 (m, 3H), 1.20 (t, J=7.0 Hz, 13.5H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 9H), 3.97 (dd, J=5.2 Hz, 2H), 4.14 (dd, J=3.2 Hz, 2H), 5.07-5.12 (m, 1H), 5.98-6.08 (m, 0.5H), 7.28-7.35 (m, 2H), 7.75-7.89 (m, 2H).

Synthetic Example 15: Synthesis of a Naphthalene-Based Epoxy Compound Including a Methoxysilyl Group and an Allyl Group (Si(OMe)$_3$:Allyl=1:9)

To a 500 ml flask, 13.52 g of naphthalene epoxy with an allyl group (Structural formula 2), 0.98 ml of trimethoxysilane, 88 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.72-0.77 (m, 0.4H), 1.73-1.80 (m, 0.4H), 2.61 (t, J=7.6 Hz, 0.4H), 2.74 (dd, J=2.6 Hz, 2H), 2.86 (dd, J=4.2 Hz, 2H), 3.30-3.34 (m, 2H), 3.58 (s, 1.8H), 3.97 (dd, J=5.2 Hz, 2H), 4.14 (dd, J=3.2 Hz, 2H), 5.07-5.12 (m, 3.6H), 5.98-6.08 (m, 1.8H), 7.28-7.35 (m, 2H), 7.75-7.89 (m, 2H).

Synthetic Example 16: Synthesis of a Biphenyl-Based Epoxy Compound Including an Ethoxysilyl Group and an Ethylsilyl Group (Si(OEt)$_3$:Si(Et)$_3$=3:1)

To a 500 ml flask, 14.76 g of biphenyl epoxy with an allyl group (Structural formula 3), 9.32 ml of triethoxysilane, 5.54 ml of triethylsilane, 156 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

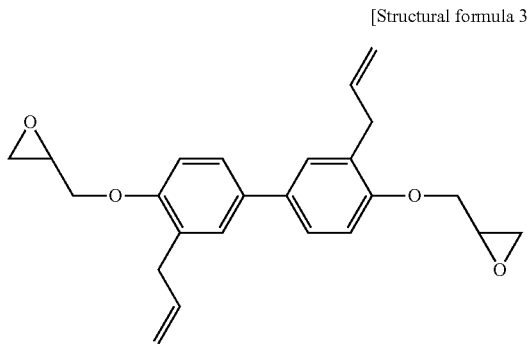

[Structural formula 3]

$^1$H NMR (400 MHz, CDCl$_3$): δ=0.42-0.53 (m, 10H), 0.84 (t, J=8.0 Hz, 4.5H), 1.20 (t, J=7.0 Hz, 13.5H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 6.70 (d, J=7.6 Hz, 2H), 6.94 (dd, J=2.8 Hz, 2H), 6.99 (d, J=7.6 Hz, 2H)

Synthetic Example 17: Synthesis of a Biphenyl-Based Epoxy Compound Including an Ethoxysilyl Group, an Ethylsilyl Group, and an Allyl Group (Si(OEt)$_3$:Si(Et)$_3$:Allyl=2:1:1)

To a 500 ml flask, 14.76 g of biphenyl epoxy with an allyl group (Structural formula 3), 6.21 ml of triethoxysilane, 2.77 ml of triethylsilane, 156 mg of a platinum oxide, and 150 ml of toluene were added and mixed, followed by stirring at 85° C. for 24 hours under argon gas. After a reaction, the obtained crude product was celite-filtered, and a solvent was removed using an evaporator to produce a final product, biphenyl epoxy including an alkoxysilyl group and an alkylsilyl group. NMR data of the obtained final product are as follows.

$^1$H NMR (400 MHz, CDCl$_3$): δ=0.42-0.53 (m, 9H), 0.84 (t, J=8.0 Hz, 4.5H), 1.20 (t, J=7.0 Hz, 9H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 4H), 3.97 (dd, J=5.2 Hz, 2H), 4.14 (dd, J=3.2 Hz, 2H), 4.93-5.01 (m, 1H), 5.80-5.95 (m, 0.5H), 6.59-6.71 (m, 0.4H), 6.87-7.04 (m, 5.6H)

Synthetic Example 18: Synthesis of a Biphenyl-Based Epoxy Compound Including an Ethoxysilyl Group and an Allyl Group (Si(OEt)$_3$:Allyl=1:1)

To a 500 ml flask, 32.84 g of biphenyl epoxy with an allyl group (Structural formula 3), 16.00 ml of triethoxysilane, 197 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 2H), 1.20 (t, J=7.0 Hz, 9H), 1.62-1.72 (m, 2H), 2.61 (t, J=7.6 Hz, 2H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 6H), 3.97 (dd, J=5.2 Hz, 2H), 4.14 (dd, J=3.2 Hz, 2H), 4.93-5.01 (m, 2H), 5.80-5.95 (m, 1H), 6.87-7.04 (m, 6H)

Synthetic Example 19: Synthesis of a Biphenyl-Based Epoxy Compound Including an Ethoxysilyl Group and an Allyl Group (Si(OEt)$_3$:Allyl=1:5)

To a 500 ml flask, 35.98 g of biphenyl epoxy with an allyl group (Structural formula 3), 14.03 ml of triethoxysilane, 216 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 1.6H), 1.20 (t, J=7.0 Hz, 7.2H), 1.62-1.72 (m, 1.6H), 2.61 (t, J=7.6 Hz, 1.6H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 4.8H), 3.97 (dd, J=5.2 Hz, 2H), 4.14 (dd, J=3.2 Hz, 2H), 4.93-5.01 (m, 2.4H), 5.80-5.95 (m, 1.2H), 6.87-7.04 (m, 6H).

Synthetic Example 20: Synthesis of a Biphenyl-Based Epoxy Compound Including an Ethoxysilyl Group and an Allyl Group (Si(OEt)$_3$:Allyl=1:0.33)

To a 500 ml flask, 8.20 g of biphenyl epoxy with an allyl group (Structural formula 3), 5.99 ml of triethoxysilane, 98 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, CDCl$_3$): δ=0.64-0.69 (m, 3H), 1.20 (t, J=7.0 Hz, 13.5H), 1.62-1.72 (m, 3H), 2.61 (t, J=7.6 Hz, 3H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 9H), 3.97 (dd, J=5.2 Hz, 2H), 4.14 (dd, J=3.2 Hz, 2H), 4.93-5.01 (m, 1H), 5.80-5.95 (m, 0.5H), 6.87-7.04 (m, 6H)

Synthetic Example 21: Synthesis of a Biphenyl-Based Epoxy Compound Including a Methoxysilyl Group and an Allyl Group (Si(OMe)$_3$:Allyl=1:9)

To a 500 ml flask, 10.26 g of biphenyl epoxy with an allyl group (Structural formula 3), 0.78 ml of trimethoxysilane, 62 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

$^1$H NMR (400 MHz, DMSO): δ=0.54 (t, J=8.0 Hz, 0.4H), 1.55 (m, 0.4H), 2.49-2.51 (m, 0.4H), 2.70 (dd, J=2.6 Hz, 2H), 2.82 (dd, J=4.2 Hz, 2H), 3.26-3.32 (m, 5.4H), 3.42 (s, 1.8H), 3.84 (dd, J=5.4 Hz, 2H), 4.26 (dd, J=3.2 Hz, 2H), 4.94-5.01 (m, 3.6H), 5.83-5.95 (m, 1.8H), 6.83-7.02 (m, 6H)

Synthetic Example 22: Synthesis of a Benzene-Based Epoxy Compound Including an Ethoxysilyl Group and an Allyl Group (Si(OEt)₃:Allyl=1:3)

To a 500 ml flask, 10 g of benzene-based epoxy with an allyl group (Structural formula 4), 3.36 ml of triethoxysilane, 75 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 4]

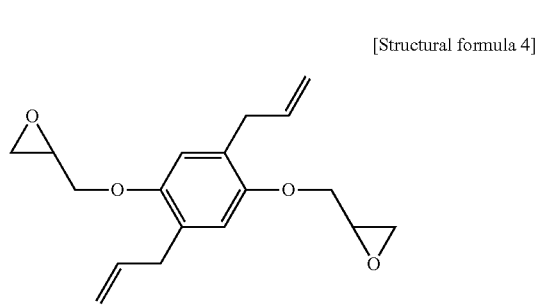 [SMILES: C=CCc1cc(OCC2CO2)c(CC=C)cc1OCC1CO1]

¹H NMR (400 MHz, CDCl₃): δ=0.64-0.69 (m, 1H), 1.20 (t, J=7.0 Hz, 4.5H), 1.62-1.72 (m, 1H), 2.61 (t, J=7.6 Hz, 1H), 2.74 (dd, J=2.6 Hz, 2H), 2.86 (dd, J=4.2 Hz, 2H), 3.11-3.35 (m, 5H), 3.79 (dt, J=19.2, 5.2, 1.6 Hz, 3H), 3.97 (dd, J=5.2 Hz, 2H), 4.14 (dd, J=3.2 Hz, 2H), 4.97-5.03 (m, 3H), 5.93-6.03 (m, 1.5H), 6.68 (s, 1H), 6.72 (s, 1H).

Synthetic Example 23: Synthesis of a Fluorene-Based Epoxy Compound Including an Ethoxysilyl Group and an Allyl Group (Si(OEt)₃:Allyl=1:3)

To a 500 ml flask, 10 g of fluorene-based epoxy with an allyl group (Structural formula 5), 1.87 ml of triethoxysilane, 42 mg of a platinum oxide, and 100 ml of toluene were added and mixed, followed by, stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 5]

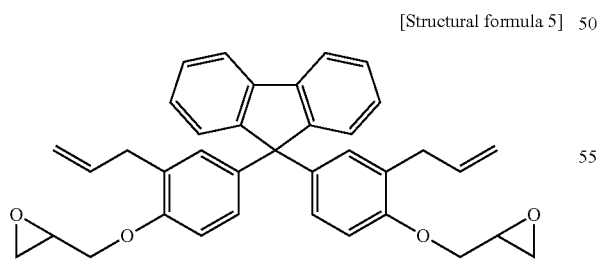

¹H NMR (400 MHz, CDCl₃): δ=0.64-0.69 (m, 1H), 1.20 (t, J=7.0 Hz, 4.5H), 1.62-1.72 (m, 1H), 2.61 (t, J=7.6 Hz, 1H), 2.74 (dd, J=2.6 Hz, 2H), 2.86 (dd, J=4.2 Hz, 2H), 3.11-3.35 (m, 5H), 3.79 (dt, J=19.2, 5.2, 1.6 Hz, 3H), 3.97 (dd, J=5.2 Hz, 2H), 4.14 (dd, J=3.2 Hz, 2H), 4.97-5.03 (m, 3H), 5.93-6.03 (m, 1.5H), 6.70 (d, J=7.6 Hz, 2H), 6.94 (dd, J=2.8 Hz, 2H), 6.99 (d, J=7.6 Hz, 2H), 7.22-7.36 (m, 6H), 7.74 (d, J=7.2 Hz, 2H).

Synthetic Example 24: Synthesis of a Tetraphenylmethane-Based Epoxy Compound Including an Ethoxysilyl Group and an Allyl Group (Si(OEt)₃:Allyl=1:3)

To a 500 ml flask, 10 g of tetraphenylmethane-based epoxy with an allyl group (Structural formula 6), 1.86 ml of triethoxysilane, 42 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 6]

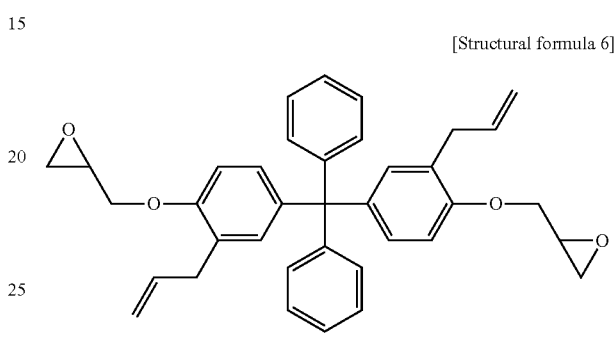

¹H NMR (400 MHz, CDCl₃): δ=0.64-0.69 (m, 1H), 1.20 (t, J=7.0 Hz, 4.5H), 1.62-1.72 (m, 1H), 2.61 (t, J=7.6 Hz, 1H), 2.74 (dd, J=2.6 Hz, 2H), 2.86 (dd, J=4.2 Hz, 2H), 3.11-3.35 (m, 5H), 3.79 (dt, J=19.2, 5.2, 1.6 Hz, 3H), 3.97 (dd, J=5.2 Hz, 2H), 4.14 (dd, J=3.2 Hz, 2H), 4.97-5.03 (m, 3H), 5.93-6.03 (m, 1.5H), 6.71-6.99 (m, 8H), 7.14-7.26 (m, 6H).

Synthetic Example 25: Synthesis of a Tetraphenylethane-Based Epoxy Compound Including an Ethoxysilyl Group and an Allyl Group (Si(OEt)₃:Allyl=1:1)

To a 500 ml flask, 10 g of tetraphenylethane-based epoxy with an allyl group (Structural formula 7), 2.80 g of triethoxysilane, 77 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 7]

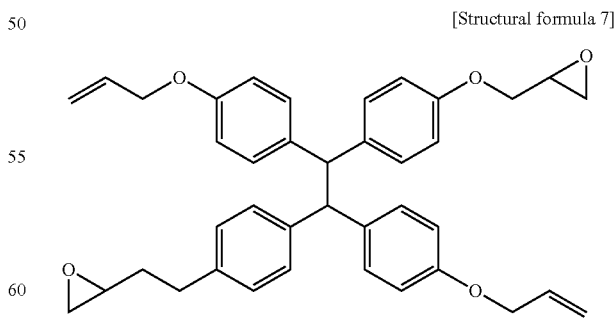

¹H NMR (400 MHz, DMSO): δ=6.98-6.87 (m, 8H), 6.66-6.55 (m, 8H), 5.94-5.82 (m, 1H), 5.28-5.11 (m, 2H), 4.54 (br. s, 2H), 4.47-4.43 (m, 2H), 4.11-4.05 (m, 2H), 3.84-3.80 (m, 8H), 3.29-3.25 (m, 4H), 2.86-2.83 (m, 2H), 2.69-2.67 (m, 2H), 1.80-1.70 (m, 2H), 1.22 (t, 9H, J=7.2 Hz), 0.67-0.60 (m, 2H)

Synthetic Example 26: Synthesis of a Tetraphenylethane-Based Epoxy Compound Including an Ethoxysilyl Group and an Ethylsilyl Group (Si(OEt)$_3$:Si(Et)$_3$=1:1)

To a 500 ml flask, 10 g of tetraphenylethane-based epoxy with a hydroxyl group (Structural formula 8), 5.10 g of diisopropylethylamine (DIPEA), 5.9 g of triethoxysilyl propylisocyanate, 3.92 g of trimethylsilyl propylisocyanate, and 200 ml of tetrahydrofuran (THF) were added and mixed, followed by stirring at 60° C. for 12 hours under argon gas. After a reaction, a reaction mixture was worked-up by using ethylacetate (EA) and H$_2$O. An organic layer was separated and MgSO$_4$ was added to the organic layer, thereby removing remaining H$_2$O. The reaction mixture was filtered using a celite filter, and a solvent was removed using an evaporator to yield a final epoxy. NMR data of the obtained final product are as follows.

[Structural formula 8]

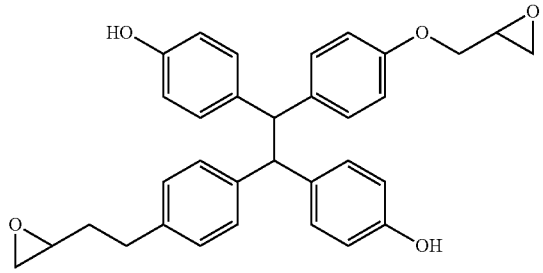

$^1$H NMR (400 MHz, DMSO): δ=7.31-7.11 (m, 12H), 6.68-6.55 (m, 4H), 5.32 (t, 2H, 6.0 Hz), 4.54 (s, 2H), 4.08-4.04 (m, 2H), 3.83-3.77 (m, 8H), 3.36-3.32 (m, 4H), 3.25-3.23 (m, 2H), 2.88-2.81 (m, 2H), 2.67-2.65 (m, 2H), 1.74-1.66 (m, 4H), 1.24 (t, 9H, J=7.2 Hz), 0.84-0.58 (m, 19H)

Synthetic Example 27: Synthesis of a Bisnaphthalene-Based Epoxy Compound Including an Ethoxysilyl Group and an Allyl Group (Si(OEt)$_3$:Allyl=1:1)

To a 500 ml flask, 10 g of bisnaphthalene-based epoxy with an allyl group (Structural formula 9), 3.13 g of triethoxysilane, 87 mg of a platinum oxide, and 100 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

[Structural formula 9]

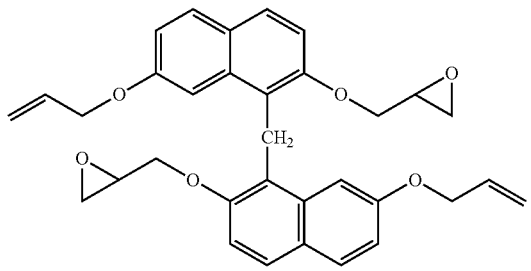

$^1$H NMR (400 MHz, DMSO): δ=7.78-7.66 (m, 4H), 7.34-7.25 (m, 4H), 6.92-6.89 (m, 2H), 5.96-5.80 (m, 1H), 5.30-5.10 (m, 2H), 4.75 (s, 2H), 4.49 (m, 2H), 4.12-4.06 (m, 2H), 3.84-3.78 (m, 8H), 3.31-3.25 (m, 2H), 2.89-2.83 (m, 4H), 2.69-2.64 (m, 2H), 1.75-1.70 (m, 2), 1.22 (t, 9H, J=7.2 Hz), 0.67-0.60 (m, 2H)

Synthetic Example 28: Synthesis of a Bisnaphthalene-Based Epoxy Compound Including an Ethoxysilyl Group and an Ethylsilyl Group (Si(OEt)$_3$:Si(Et)$_3$=1:1)

To a 500 ml flask, 10 g of bisnaphthalene-based epoxy with a hydroxyl group (Structural formula 10), 5.82 g of diisopropylethylamine (DIPEA), 6.7 g of triethoxysilyl propylisocyanate, 4.49 g of trimethylsilyl propylisocyanate, and 200 ml of tetrahydrofuran (THF) were added and mixed, followed by stirring at 60° C. for 12 hours under argon gas. After a reaction, a reaction mixture was worked-up by using ethylacetate (EA) and H$_2$O. An organic layer was separated and MgSO$_4$ was added to the organic layer, thereby removing remaining H$_2$O. The reaction mixture was filtered using a celite filter, and a solvent was removed using an evaporator to yield a final epoxy. NMR data of the obtained final product are as follows.

[Structural formula 10]

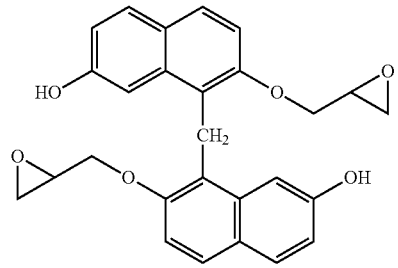

$^1$H NMR (400 MHz, DMSO): δ=7.78-7.66 (m, 4H), 7.34-7.25 (m, 4H), 6.92-6.89 (m, 2H), 4.75 (s, 2H), 4.12-4.06 (m, 2H), 3.84-3.78 (m, 8H), 3.36-3.25 (m, 6H), 2.89-2.83 (m, 2H), 2.69-2.64 (m, 2H), 1.75-1.70 (m, 4H), 1.22 (t, 9H, J=7.2 Hz), 0.88-0.57 (m, 19H)

Synthetic Example 29: Synthesis of a Phenol Novolac-Based Epoxy Compound Including an Ethoxysilyl Group and an Allyl Group (Si(OEt)$_3$:Allyl=1:1)

To a flask, 10 g of phenol novolac epoxy with an allyl group (Structural formula 11), 98 mg of a platinum oxide, 3.57 g of triethoxysilane, and 150 ml of toluene were added, followed by stirring at room temperature for 5 minutes. Then, a reaction mixture was heated and stirred at 85° C. for 24 hours. After a reaction, the obtained crude product was celite-filtered, and a solvent was removed using an evaporator to yield a final epoxy in which a concentration ratio of an epoxy group to an ethoxysilyl group to an allyl group was 1:1:1. NMR data of the obtained final product are as follows.

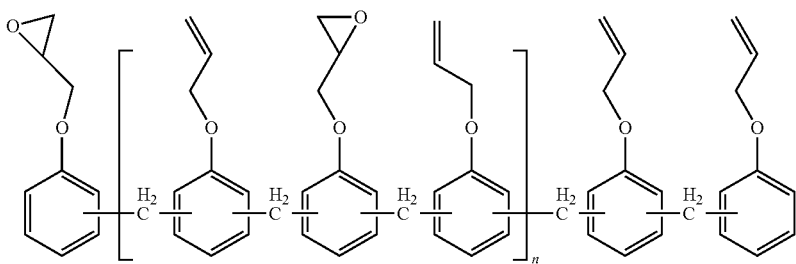

[Structural formula 11]

¹H NMR (400 MHz, CDCl₃): δ=7.15-6.70 (m, 21.68H), 6.04-6.00 (m, 2.21H), 5.41-5.20 (m, 4.65H), 4.49-4.47 (m, 4.58H), 4.20-3.79 (m, 32.48H), 3.33-3.25 (m, 2.35H), 2.73-2.59 (m, 5.99H), 1.82-1.70 (m, 4.48H), 1.24-1.20 (m, 18.75H), 0.80-0.61 (m, 4.16H)

Synthetic Example 30: Synthesis of a Cresol Novolac-Based Epoxy Compound Including an Ethoxysilyl Group and an Allyl Group (Si(OEt)₃:Allyl=1:1)

To a flask, 10 g of cresol novolac-based epoxy with an allyl group (Structural formula 12), 92 mg of a platinum oxide, 4.00 g of triethoxysilane, and 150 ml of toluene were added, followed by stirring at room temperature for 5 minutes. Then, a reaction mixture was heated and stirred at 85° C. for 24 hours. After a reaction, the obtained crude product was celite-filtered, and a solvent was removed using an evaporator to yield a final epoxy in which a concentration ratio of an epoxy group to an ethoxysilyl group to an allyl group was 1:1:1. NMR data of the obtained final product are as follows.

¹H NMR (400 MHz, DMSO): δ=7.02-6.89 (m, 10H), 6.05-6.01 (m, 1.43H), 5.43-5.20 (m, 3.04H), 4.50-4.46 (m, 3.28H), 4.24-3.36 (m, 23.4H), 3.34-3.19 (m, 1.55H), 2.84-2.52 (m, 3.7H), 2.24-2.10 (m, 12.3H), 1.83-1.70 (m, 2.74H), 1.24-1.20 (m, 12.11H), 0.80-0.61 (m, 2.53H)

Synthetic Example 31: Synthesis of a Bisphenol Novolac-Based Epoxy Compound Including an Ethoxysilyl Group and an Allyl Group (Si(OEt)₃:Allyl=1:1)

To a flask, 10 g of bisphenol novolac-based epoxy with an allyl group (Structural formula 13), 92 mg of a platinum oxide, 4.0 g of triethoxysilane, and 150 ml of toluene were added, thereby stirring for 5 minutes at room temperature. Then, a reaction mixture was heated and stirred at 85° C. for 24 hours. After a reaction, the obtained crude product was celite-filtered, and a solvent was removed using an evaporator to yield a final epoxy in which a concentration ratio of an epoxy group to an ethoxysilyl group to an allyl group was 1:1:1. NMR data of the obtained final product are as follows.

[Structural formula 12]

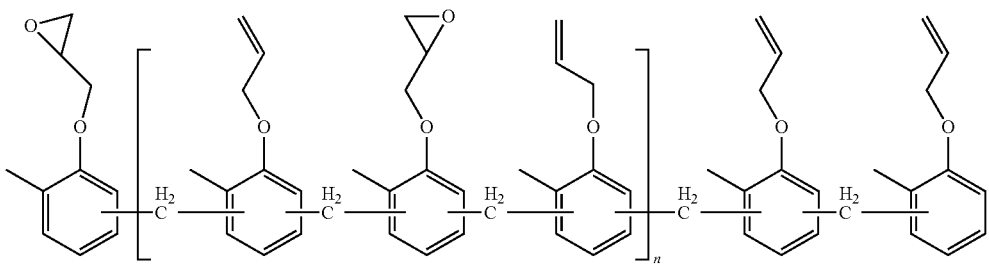

[Structural formula 13]

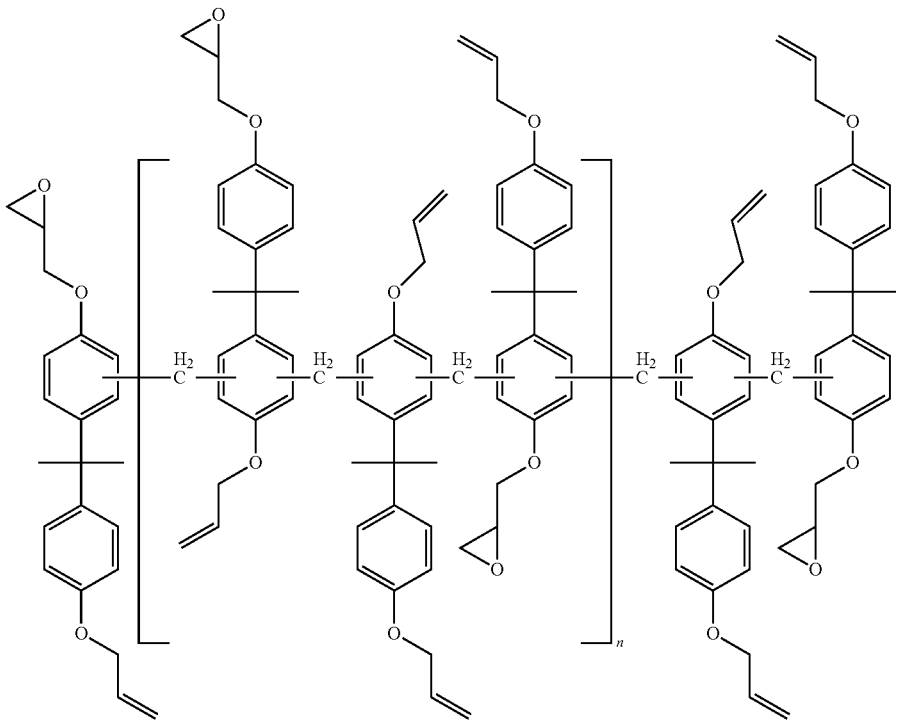

¹H NMR (400 MHz, DMSO): δ=7.32-7.24 (m, 12H), 6.75-6.65 (m, 20H), 6.06-6.15 (m, 1.72H), 5.42-5.22 (m, 3.54H), 4.51-4.47 (m, 3.91H), 4.22-3.79 (m, 42.14H), 3.36-3.28 (m, 15.01H), 2.77-2.58 (m, 14.55H), 1.83-1.69 (m, 3.55H), 1.62 (m, 32.9H), 1.27-1.20 (m, 17.04H), 0.83-0.62 (m, 3.12H)

Synthetic Example 32: Synthesis of a Naphthalene Novolac-Based Epoxy Compound Including an Ethoxysilyl Group and an Allyl Group (Si(OEt)₃:Allyl=1:1)

To a flask, 10 g of naphthalene novolac-based epoxy with an allyl group (Structural formula 14), 82 mg of a platinum oxide, 3.56 g of triethoxysilane, and 150 ml of toluene were added, followed by stirring for 5 minutes at room temperature. Then, a reaction mixture was heated and stirred at 85° C. for 24 hours. After a reaction, the obtained crude product was celite-filtered, and a solvent was removed using an evaporator to yield a final epoxy in which a concentration ratio of an epoxy group to an ethoxysilyl group to an allyl group was 1:1:1. NMR data of the obtained final product are as follows.

¹H NMR (400 MHz, DMSO): δ=8.03-8.02 (m, 1.27H), 7.88-7.51 (m, 9.99H), 7.39-7.02 (m, 10.43H), 6.59-6.54 (m, 4.41H), 6.05-6.01 (m, 1.17H), 5.40-5.20 (m, 2.45H), 4.50-4.46 (m, 2.47H), 4.42H (s, 3.84H), 4.21-3.80 (m, 15.4H), 3.35-3.25 (m, 7.2H), 2.74-2.59 (m, 9.8H), 1.83-1.69 (m, 1.22H), 1.25-1.21 (m, 5.97H), 0.80-0.61 (m, 1.09H)

Synthetic Example 33: Synthesis of a Bisaniline-Based Epoxy Compound Including an Ethoxysilyl Group and an Allyl Group (Si(OEt)₃:Allyl=1:1)

To a flask, 20 g of bisaniline-based epoxy with an allyl group (Structural formula 15), 0.12 g of a platinum oxide (PtO₂), 9.7 g of triethoxysilane, and 250 ml of toluene were added, thereby stirring for 5 minutes at room temperature. Then, a reaction mixture was heated and stirred at 85° C. for 12 hours. After a reaction, the obtained crude product was celite-filtered, and a solvent was removed using an evaporator to yield a final epoxy in which a concentration ratio of an epoxy group to an ethoxysilyl group to an allyl group is 2:1:1. NMR data of the obtained final product are as follows.

[Structural formula 14]

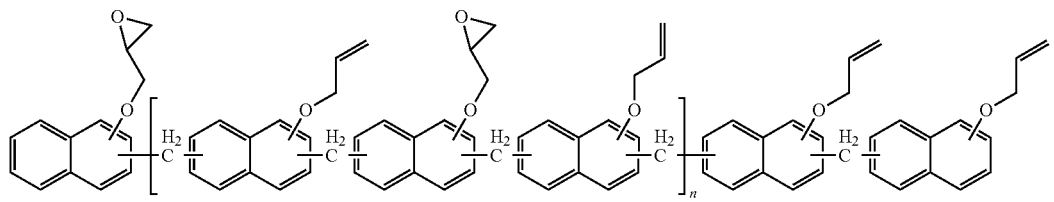

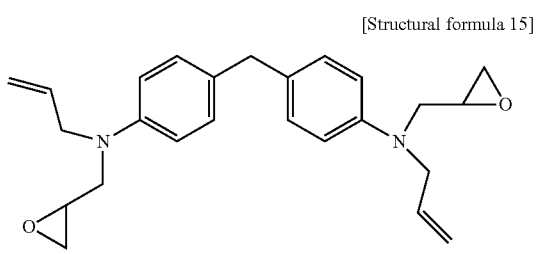 [SMILES: C=CCN(CC1CO1)c1ccc(Cc2ccc(N(CC=C)CC3CO3)cc2)cc1]

[Structural formula 15]

¹H NMR (400 MHz, CDCl₃): δ=7.12-7.08 (m, 4H), 6.77-6.74 (m, 4H), 5.93-5.80 (m, 1.01H), 5.48-5.30 (m, 2.11H), 3.84 (q, 6.06H, J=6.8 Hz), 3.82 (s, 2H), 3.76-3.62 (m, 4.25H), 3.49-3.40 (m, 1.8H), 3.22-3.16 (m, 3.99H), 2.81-2.78 (m, 1.8H), 2.60-2.58 (m, 1.8H), 1.80-1.70 (m, 2.01H), 1.22 (t, 8.82H, J=7.2 Hz), 0.67-0.60 (m, 1.79H)

Synthetic Example 34: Synthesis of a Diamine-Based Epoxy Compound Including an Ethoxysilyl Group and an Allyl Group (Si(OEt)₃:Allyl=1:1)

To a flask, 10 g of a diamine-based epoxy compound with an allyl group (Structural formula 16), 0.14 g of a platinum oxide (PtO₂), 12.0 g of triethoxysilane, and 250 ml of toluene were added, followed by stirring for 5 minutes at room temperature. Then, a reaction mixture was heated and stirred at 80° C. for 12 hours. After a reaction, the obtained crude product was celite-filtered, and a solvent was removed using an evaporator to yield a final epoxy in which a concentration ratio of an epoxy group to an ethoxysilyl group to an allyl group is 2:1:1. NMR data of the obtained final product are as follows.

[Structural formula 16]

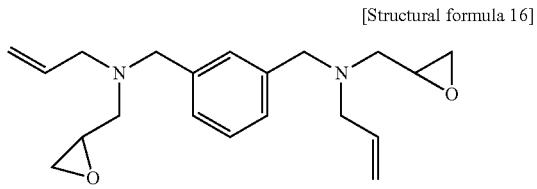 [SMILES: C=CCN(Cc1cccc(CN(CC=C)CC2CO2)c1)CC1CO1]

¹H NMR (400 MHz, CDCl₃): δ=7.41-7.09 (m, 4H), 5.93-5.80 (m, 1H), 5.44-5.21 (m, 2H), 3.84-3.54 (m, 12H), 3.25-3.11 (m, 2H), 2.85-2.42 (m, 10H), 1.81-1.69 (m, 2H), 1.22 (t, 9H, J=7.2 Hz), 0.66-0.60 (m, 2H)

Comparative Synthetic Example 1: Synthesis of a Bisphenol A-Based Epoxy Compound Including an Ethoxysilyl Group (Si(OEt)₃:Si(Et)₃:Allyl=1:0:0)

To a 500 ml flask, 26.25 g of bisphenol A epoxy with an allyl group (Structural formula 1), 25.35 ml of triethoxysilane, 250 mg of a platinum oxide, and 200 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

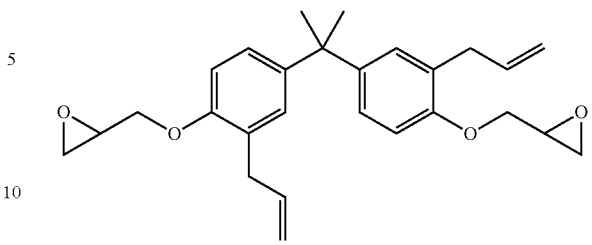

[Structural formula 1]

¹H NMR (400 MHz, CDCl₃): δ=0.64-0.69 (m, 4H), 1.20 (t, J=7.0 Hz, 18H), 1.60 (s, 6H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (dt, J=19.2, 5.2, 1.6 Hz, 12H), 3.97 (dd, J=5.2 Hz, 2H), 4.14 (dd, J=3.2 Hz, 2H), 6.70 (d, J=7.6 Hz, 2H), 6.94 (dd, J=2.8 Hz, 2H), 6.99 (d, J=7.6 Hz, 2H).

Comparative Synthetic Example 2: Synthesis of a Bisphenol A-Based Epoxy Compound Including a Methoxysilyl Group (Si(OMe)₃:Si(Me)₃:Allyl=1:0:0)

To a 500 ml flask, 17.28 g of bisphenol A epoxy with an allyl group (Structural formula 1), 31.38 ml of trimethoxysilane, 279 mg of a platinum oxide, and 150 ml of toluene were added and mixed, followed by stirring at 85° C. for 24 hours under argon gas. After a reaction, the obtained crude product was celite-filtered, and a solvent was removed using an evaporator to yield a final epoxy. NMR data of the obtained final product are as follows.

¹H NMR (400 MHz, CDCl₃): δ=0.64-0.69 (m, 4H), 1.60 (s, 6H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.45 (s, 9H), 3.97 (dd, J=5.2 Hz, 2H), 4.14 (dd, J=3.2 Hz, 2H), 6.70 (d, J=7.6 Hz, 2H), 6.94 (dd, J=2.8 Hz, 2H), 6.99 (d, J=7.6 Hz, 2H).

Evaluation of physical properties: Preparation of cured product and characterization of thermal resistance properties 1. Preparation of Epoxy Composite (1) Preparation of Epoxy Glass Fiber Composite (Cured Product)

An epoxy compound, silica slurry (a solids content of 70 wt %, a 2-methoxyethanol, an average silica size of 1 μm), and polyvinyl acetal were dissolved in methylethylketone according to a formulation in Table 1. The solids content was 40 wt %. After the mixture was stirred at a rate of 1500 rpm for 1 hour, a curing agent was added to the mixed solution and additionally mixed for 50 minutes. Into this epoxy mixture, a glass fiber (Nittobo Co., Glass fiber fabric T-glass) was impregnated to prepare a glass fiber composite. Then, the composite was placed into a vacuum oven heated to 100° C. and a solvent was removed, followed by curing in a hot press preheated to 120° C., at 120° C. for 2 hours, at 180° C. for 2 hours, and at a temperature >200° C. for 2 hours, thereby obtaining a glass fiber composite film (4 mm×6 mm×0.1 mm). When a composite film is prepared, a resin content of the composite film is adjusted according to pressure of a press and viscosity of a resin, and a resin content in the composite film is described in Table 1.

(2) Preparation of Epoxy Filler Composite (Cured Product)

An epoxy compound, silica slurry (a solids content of 70 wt %, a 2-methoxyethanol, an average silica particle size of 1 μm), and polyvinyl acetal were dissolved in methylethylketone according to a formulation in Table 2. The solids content was 40 wt %. After the mixture was stirred at a rate of 1500 rpm for 1 hour, a curing agent was added to the mixed solution and additionally mixed for 50 minutes. The mixture was placed into a vacuum oven heated to 100° C. and a solvent was removed, followed by curing in a hot press preheated to 120° C., at 120° C. for 2 hours, at 180° C. for 2 hours, and at a temperature >200° C. for 2 hours, thereby obtaining an epoxy filler (inorganic particles) composite (5 mm×5 mm×5 mm).

2. Characterization of Thermal Resistant Properties

A dimensional changes with a temperature of a cured product obtained in Examples in Tables 1 and 2 were measured by using a thermo-mechanical analyzer, and are shown in Tables 1 and 2. The specimen of an epoxy glass fiber composite film was prepared with the dimension of 4×16×0.1 (mm³), and a specimen of a filler composite was prepared with the dimension of 5×5×3 (mm³).

TABLE 1

| | | Epoxy Compound (Synthetic Example No.) | Example 1 | Example 2 | Example 3 | Example 4 | Example 5 | Example 6 | Example 7 | Example 8 |
|---|---|---|---|---|---|---|---|---|---|---|
| Composition: Epoxy Formulation (g) | Epoxy | Synthetic example 1 | 5.00 | 5.00 | | | | | | |
| | | Synthetic example 2 | | | 5.00 | | | | | |
| | | Synthetic example 3 | | | | 5.00 | | | | |
| | | Synthetic example 4 | | | | | 5.00 | | | |
| | | Synthetic example 5 | | | | | | 5.00 | | |
| | | Synthetic example 6 | | | | | | | 5.00 | |
| | | Synthetic example 7 | | | | | | | | 5.00 |
| | | Synthetic example 8 | | | | | | | | |
| | | Synthetic example 9 | | | | | | | | |
| | | Synthetic example 10 | | | | | | | | |
| | | Synthetic example 11 | | | | | | | | |
| | | Synthetic example 12 | | | | | | | | |
| | | Synthetic example 13 | | | | | | | | |
| | | Synthetic example 14 | | | | | | | | |
| | | Synthetic example 15 | | | | | | | | |
| | | Synthetic example 16 | | | | | | | | |
| | | Synthetic example 17 | | | | | | | | |
| | | Synthetic example 18 | | | | | | | | |
| | | Synthetic example 19 | | | | | | | | |
| | | Synthetic example 20 | | | | | | | | |
| | | Synthetic example 21 | | | | | | | | |
| | | Synthetic example 25 | | | | | | | | |
| | | Synthetic example 27 | | | | | | | | |
| | | Synthetic example 29 | | | | | | | | |
| | | DGEBA[1] | | | | | | | | |
| | | EXA4700[2] | | 2.23 | | | | | | |
| | | YX4000H[3] | | | | | | | | |
| | | Polydis[4] | | | | | | | | |
| | | HF-1M[5] | | | | | 2.33 | 2.08 | | |
| | | TPP[6] | | | | | | | | |
| | | 2E4MZ[7] | 0.35 | 0.36 | 0.25 | 0.25 | 0.04 | 0.04 | 0.35 | 0.15 |
| | | Polyvinyl acetal | 0.56 | 0.80 | 0.56 | 0.56 | 0.56 | 0.56 | 0.56 | 0.56 |
| | | Silica | 10.97 | 15.58 | 10.78 | 10.78 | 14.70 | 14.24 | 5.91 | 10.60 |

TABLE 1-continued

| | | | | | | | | | | |
|---|---|---|---|---|---|---|---|---|---|---|
| | | | Epoxy Glass Fiber Composite | | | | | | | |
| | | Type of Glass Fiber | T | T | T | T | T | T | T | T |
| | | Resin Content (wt %) | 51% | 50% | 50% | 47% | 50% | 50% | 44% | 51% |
| Thermal Properties | CTE (ppm/° C.) | $\alpha_1$ (T < Tg) | 3.0 | 3.7 | 4.4 | 3.9 | 3.5 | 4.1 | 3.3 | 4.7 |
| | | Tg (° C.) | Tg-Less | Tg-Less | Tg-Less | Tg-Less | Tg-Less | Tg-Less | Tg-Less | Tg-Less |

| | | | Example 9 | Example 10 | Example 11 | Example 12 | Example 13 | Example 14 | Example 15 | Example 16 |
|---|---|---|---|---|---|---|---|---|---|---|
| | | Epoxy Compound (Synthetic Example No.) | | | | | | | | |
| Composition: Epoxy Formulation (g) | Epoxy | Synthetic example 1 | | | | | | | | |
| | | Synthetic example 2 | | | | | | | | |
| | | Synthetic example 3 | | | | | | | | |
| | | Synthetic example 4 | | | | | | | | |
| | | Synthetic example 5 | | | | | | | | |
| | | Synthetic example 6 | | | | | | | | |
| | | Synthetic example 7 | | | | | | | | |
| | | Synthetic example 8 | 5.00 | | | | | | | |
| | | Synthetic example 9 | | 5.00 | | | | | | |
| | | Synthetic example 10 | | | 5.00 | 5.00 | | | | |
| | | Synthetic example 11 | | | | | 5.00 | | | |
| | | Synthetic example 12 | | | | | | 5.00 | | |
| | | Synthetic example 13 | | | | | | | 5.00 | |
| | | Synthetic example 14 | | | | | | | | 5.00 |
| | | Synthetic example 15 | | | | | | | | |
| | | Synthetic example 16 | | | | | | | | |
| | | Synthetic example 17 | | | | | | | | |
| | | Synthetic example 18 | | | | | | | | |
| | | Synthetic example 19 | | | | | | | | |
| | | Synthetic example 20 | | | | | | | | |
| | | Synthetic example 21 | | | | | | | | |
| | | Synthetic example 25 | | | | | | | | |
| | | Synthetic example 27 | | | | | | | | |
| | | Synthetic example 29 | | | | | | | | |
| | | DGEBA[1] | | | | | | | | |
| | | EXA4700[2] | | | | 2.45 | | | | |
| | | YX4000H[3] | | | | | | | | |
| | | Polydis[4] | | | | | | | | |
| | | HF-1M[5] | | | | | | | | |
| | | TPP[6] | | | | | | | | |
| | | 2E4MZ[7] | 0.15 | 0.25 | 0.15 | 0.37 | 0.15 | 0.15 | 0.15 | 0.15 |
| | | Polyvinyl acetal | 0.56 | 0.56 | 0.56 | 0.83 | 0.56 | 0.56 | 0.56 | 0.56 |
| | | Silica | 10.60 | 10.78 | 10.60 | 16.07 | 10.60 | 10.60 | 10.60 | 10.60 |
| | | Type of Glass Fiber | T | T | T | T | T | T | T | T |
| | | Resin Content (wt %) | 47% | 50% | 50% | 52% | 48% | 49% | 51% | 51% |
| Thermal Properties | CTE (ppm/° C.) | $\alpha_1$ (T < Tg) | 3.3 | 2.1 | 3.0 | 3.6 | 4.2 | 4.0 | 4.9 | 3.4 |

TABLE 1-continued

| | | | Epoxy Glass Fiber Composite | | | | | | | | |
|---|---|---|---|---|---|---|---|---|---|---|---|
| | | Tg (° C.) | Tg-Less | Tg-Less | Tg-Less | Tg-Less | Tg-Less | Tg-Less | Tg-Less | Tg-Less |
| | | Epoxy Compound (Synthetic Example No.) | Example 17 | Example 18 | Example 19 | Example 20 | Example 21 | Example 22 | Example 23 | Example 24 |
| Composition: Epoxy Formulation (g) | Epoxy | Synthetic example 1 | | | | | | | | |
| | | Synthetic example 2 | | | | | | | | |
| | | Synthetic example 3 | | | | | | | | |
| | | Synthetic example 4 | | | | | | | | |
| | | Synthetic example 5 | | | | | | | | |
| | | Synthetic example 6 | | | | | | | | |
| | | Synthetic example 7 | | | | | | | | |
| | | Synthetic example 8 | | | | | | | | |
| | | Synthetic example 9 | | | | | | | | |
| | | Synthetic example 10 | | | | | | | | |
| | | Synthetic example 11 | | | | | | | | |
| | | Synthetic example 12 | | | | | | | | |
| | | Synthetic example 13 | | | | | | | | |
| | | Synthetic example 14 | | | | | | | | |
| | | Synthetic example 15 | 5.00 | | | | | | | |
| | | Synthetic example 16 | | 5.00 | 5.00 | | | | | |
| | | Synthetic example 17 | | | | 5.00 | | | | |
| | | Synthetic example 18 | | | | | 5.00 | | | |
| | | Synthetic example 19 | | | | | | 5.00 | | |
| | | Synthetic example 20 | | | | | | | 5.00 | |
| | | Synthetic example 21 | | | | | | | | 5.00 |
| | | Synthetic example 25 | | | | | | | | |
| | | Synthetic example 27 | | | | | | | | |
| | | Synthetic example 29 | | | | | | | | |
| | | DGEBA[1] | | | | | | | | |
| | | EXA4700[2] | | | 2.36 | | | | | |
| | | YX4000H[3] | | | | | | | | |
| | | Polydis[4] | | | | | | | | |
| | | HF-1M[5] | | | | | | | | |
| | | TPP[6] | | | | | | | | |
| | | 2E4MZ[7] | 0.15 | 0.25 | 0.37 | 0.25 | 0.25 | 0.25 | 0.25 | 0.25 |
| | | Polyvinyl acetal | 0.56 | 0.56 | 0.82 | 0.56 | 0.56 | 0.56 | 0.56 | 0.56 |
| | | Silica | 10.60 | 10.78 | 15.87 | 10.78 | 10.78 | 10.78 | 10.78 | 10.78 |
| | | Type of Glass Fiber | T | T | T | T | T | T | T | T |
| | | Resin Content (wt %) | 49% | 49% | 50% | 50% | 54% | 49% | 56% | 50% |
| Thermal Properties | CTE (ppm/° C.) | $\alpha_1$ (T < Tg) | 4.1 | 2.9 | 3.5 | 3.8 | 3.5 | 3.6 | 3.1 | 4.2 |
| | | Tg (° C.) | Tg-Less | Tg-Less | Tg-Less | Tg-Less | Tg-Less | Tg-Less | Tg-Less | Tg-Less |

TABLE 1-continued

| Epoxy Glass Fiber Composite | | | | | | | | |
|---|---|---|---|---|---|---|---|---|
| | | Epoxy Compound (Synthetic Example No.) | Example 25 | Example 26 | Example 27 | Comparative Ex. 1 | Comparative Ex. 2 | Comparative Ex. 3 |
| Composition: Epoxy Formulation (g) | Epoxy | Synthetic example 5 | | | | | | |
| | | Synthetic example 6 | | | | | | |
| | | Synthetic example 7 | | | | | | |
| | | Synthetic example 8 | | | | | | |
| | | Synthetic example 9 | | | | | | |
| | | Synthetic example 10 | | | | | | |
| | | Synthetic example 11 | | | | | | |
| | | Synthetic example 12 | | | | | | |
| | | Synthetic example 13 | | | | | | |
| | | Synthetic example 14 | | | | | | |
| | | Synthetic example 15 | | | | | | |
| | | Synthetic example 16 | | | | | | |
| | | Synthetic example 17 | | | | | | |
| | | Synthetic example 18 | | | | | | |
| | | Synthetic example 19 | | | | | | |
| | | Synthetic example 20 | | | | | | |
| | | Synthetic example 21 | | | | | | |
| | | Synthetic example 25 | 5.00 | | | | | |
| | | Synthetic example 27 | | 5.00 | | | | |
| | | Synthetic example 29 | | | 5.00 | | | |
| | | DHS-(Si(OEt)$_3$) 100% | | | | 5.00 | | |
| | | DHS-(Si(OMe)$_3$) 100% | | | | | 5.00 | |
| | | DGEBA[1] | | | | | | 5.00 |
| | | EXA4700[2] | | | | | | |
| | | YX4000H[3] | | | | | | |
| | | Polydis[4] | | | | | | |
| | | HF-1M[5] | 1.70 | 1.86 | 1.03 | 1.35 | 1.61 | 2.84 |
| | | TPP[6] | | | | 0.05 | 0.05 | |
| | | 2E4MZ[7] | 0.04 | 0.04 | 0.04 | | | 0.04 |
| | | Polyvinyl acetal | 0.56 | 0.56 | 0.56 | | | 0.56 |
| | | Silica | 13.55 | 13.84 | 12.29 | 6.40 | | 15.67 |
| | | Type of Glass Fiber | T | T | T | T | | T |
| | | Resin Content (wt %) | 52% | 54% | 52% | 45% | | 49% |
| Thermal Properties | CTE (ppm/° C.) | $\alpha_1$ (T < Tg) | 3.4 | 3.6 | 3.6 | 2.9 | Impossible to produce measurement sample | 5.9 |
| | | Tg (° C.) | Tg-Less | Tg-Less | Tg-Less | Tg-Less | | 180 |

TABLE 2

| | | Filler Composite | | | | | | | |
|---|---|---|---|---|---|---|---|---|---|
| | Compound (Synthetic Example No.) | | Example 28 | Example 29 | Example 30 | Example 31 | Example 32 | Example 33 | Example 34 | Example 35 |
| Composition: formulation (g) | Silyl Compound & Epoxy | Synthetic example 1 | 3.00 | | | | | | | |
| | | Synthetic example 3 | | 3.00 | | | | | | |
| | | Synthetic example 5 | | | 3.00 | | | | | |
| | | Synthetic example 6 | | | | 3.00 | 2.50 | | | |
| | | Synthetic example 11 | | | | | | 3.00 | 2.70 | |
| | | Synthetic example 12 | | | | | | | | 3.00 |
| | | Synthetic example 16 | | | | | | | | |
| | | Synthetic example 18 | | | | | | | | |
| | | Synthetic example 21 | | | | | | | | |
| | | Synthetic example 25 | | | | | | | | |
| | | Synthetic example 27 | | | | | | | | |
| | | Synthetic example 31 | | | | | | | | |
| | | DGEBA[1] | | | | | | | | |
| | | EXA4700[2] | | | | | 0.50 | | 0.30 | |
| | | YX4000H[3] | | | | | | | | |
| | | Polydis[4] | 0.37 | 0.37 | 0.37 | 0.37 | 0.37 | 0.37 | 0.37 | 0.37 |
| | HF-1M[5] | | | | | | | | | |
| | TPP[6] | | | | | | | | | |
| | 2E4MZ[7] | | 0.17 | 0.24 | 0.17 | 0.24 | 0.12 | 0.17 | 0.12 | 0.17 |
| | Polyvinyl acetal | | 0.74 | 0.74 | 0.74 | 0.74 | 0.74 | 0.74 | 0.74 | 0.74 |
| | Silica | | 17.12 | 17.40 | 17.12 | 17.40 | 16.92 | 17.12 | 16.92 | 17.12 |
| | Filler Content (wt %) | | 80 | 80 | 80 | 80 | 80 | 80 | 80 | 80 |
| Thermal Properties | CTE (ppm/° C.) | $\alpha_1$ (T < Tg) | 6.34 | 8.85 | 5.14 | 5.99 | 5.93 | 5.22 | 5.19 | 5.47 |
| | Tg (° C.) | | Tg-Less | Tg-Less | Tg-Less | Tg-Less | Tg-Less | Tg-Less | Tg-Less | Tg-Less |
| | Compound (Synthetic Example No.) | | Example 36 | Example 37 | Example 38 | Example 39 | Example 40 | Example 41 | Example 42 | Comparative Ex. 4 |
| Composition: formulation (g) | Silyl Compound & Epoxy | Synthetic example 1 | | | | | | | | |
| | | Synthetic example 3 | | | | | | | | |
| | | Synthetic example 5 | | | | | | | | |
| | | Synthetic example 6 | | | | | | | | |
| | | Synthetic example 11 | | | | | | | | |
| | | Synthetic example 12 | | | | | | | | |
| | | Synthetic example 16 | 3.00 | | | | | | | |
| | | Synthetic example 18 | | 3.00 | 2.7 | | | | | |
| | | Synthetic example 21 | | | | 3.00 | | | | |
| | | Synthetic example 25 | | | | | 3.00 | | | |
| | | Synthetic example 27 | | | | | | 3.00 | | |
| | | Synthetic example 31 | | | | | | | 2.50 | |
| | | DGEBA[1] | | | | | | | | 5.00 |
| | | EXA4700[2] | | | | | | | 0.50 | |
| | | YX4000H[3] | | | 0.30 | | | | | |
| | | Polydis[4] | 0.37 | 0.37 | 0.37 | 0.37 | 0.37 | 0.37 | 0.37 | |
| | HF-1M[5] | | 1.24 | | | 2.04 | 1.14 | 1.24 | 1.00 | 2.84 |
| | TPP[6] | | 0.02 | | | 0.02 | | | 0.02 | 0.05 |
| | 2E4MZ[7] | | | 0.17 | 0.12 | | 0.02 | 0.02 | | |
| | Polyvinyl acetal | | 0.74 | 0.74 | 0.74 | 0.74 | 0.74 | 0.74 | 0.74 | |

TABLE 2-continued

| | | Filler Composite | | | | | | | |
|---|---|---|---|---|---|---|---|---|---|
| | Silica | 21.48 | 17.12 | 16.92 | 24.68 | 21.08 | 21.48 | 20.52 | 31.56 |
| | Filler Content (wt %) | 80 | 80 | 80 | 80 | 80 | 80 | 80 | 80 |
| Thermal Properties | CTE $\alpha_1$ (ppm/° C.) (T < Tg) | 6.29 | 4.42 | 6.29 | 8.73 | 8.03 | 7.86 | 7.24 | 14.44 |
| | Tg (° C.) | Tg-Less | Tg-Less | Tg-Less | Tg-Less | Tg-Less | Tg-Less | Tg-Less | 110 |

*Note:
Compounds used in Tables 1 and 2 are as follows.
(1)DGEBA: Diglycidyl ether of bisphenol A (Mw = 377, Aldrich Co.)
(2)EXA4700: Bisnaphthalene-based epoxy (EEW = 162)

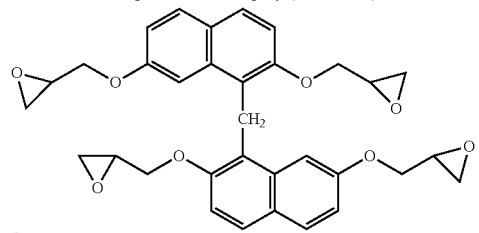

(3)YX4000H: Biphenyl-based epoxy

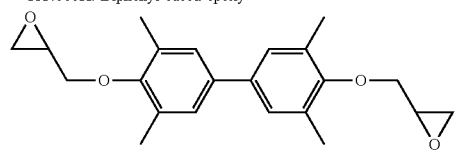

(4)Polydis ®: Rubber-modified epoxy (Struktol Co.)
(5)HF-1M: Phenol novolac-based curing agent (Meiwa Plastic Industries, HEW = 107)

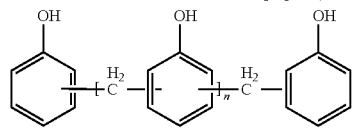

(6)TPP: Triphenyl phosphine (Aldrich Co.)
(7)2E4MZ: 2-ethyl-4-methylimidazole (Aldrich Co.)

Figure 1B:
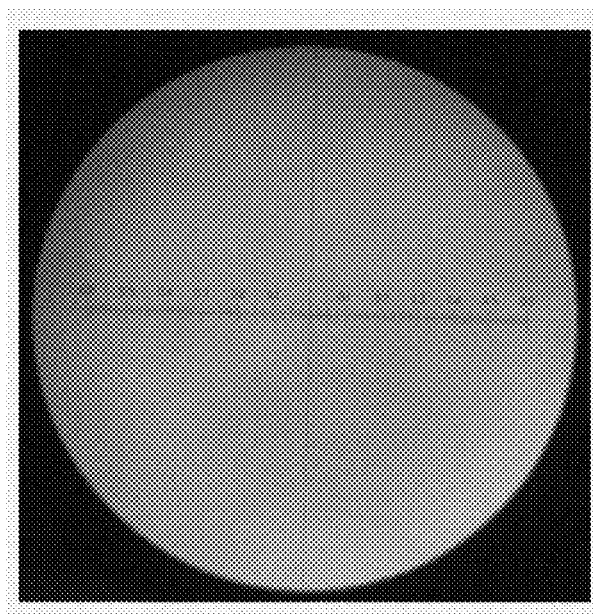
FIG. 1B is a microscope image (100× magnification) of the surface of a glass fiber composite produced using Synthesis Example 4.

As shown in Tables 1 and 2, a glass fiber composite and a silica composite, prepared by an epoxy compound according to an exemplary embodiment in the present disclosure, exhibit a low CTE, and do not exhibit a glass transition temperature (Tg-less), thereby improving thermal resistance. In addition, the brittleness of a composite prepared using an epoxy compound according to an exemplary embodiment in the present disclosure is improved due to the introduction of a non-reactive functional group. As shown in FIGS. 1A and 1B, cracks are observed in a surface of a specimen of a glass fiber composite of an epoxy compound (Comparative Synthetic Example 1) with only an ethoxysilyl group. In comparison, in a case of an epoxy compound (Synthetic Example 4) with an allyl group and an ethoxysilyl group at the same time, a crack is not observed in a surface of a cured glass fiber composite.

Figure 2A:
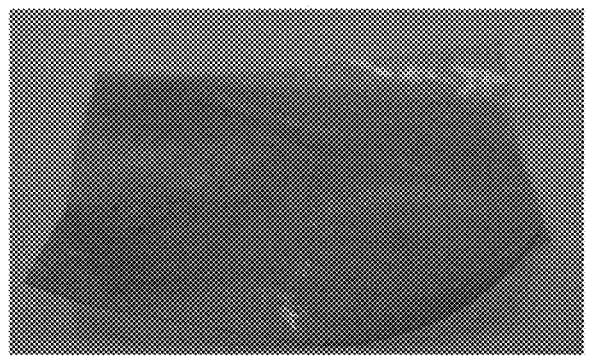
FIG. 2A is an appearance of a glass fiber composite made by Comparative Synthesis Example 2.
Figure 2B:
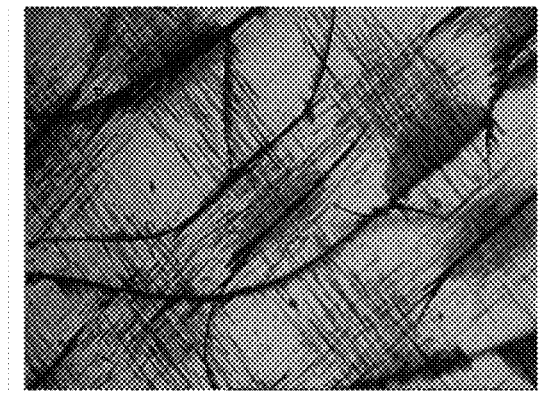
FIG. 2B is a microscope image (100× magnification) which shows the internal cracking of the glass fiber composite made by Comparative Synthesis Example 2

In a case of an epoxy compound (Comparative Synthetic Example 2) with only a methoxysilyl group, as shown in FIGS. 2A and 2B, a curing rate is significantly fast and the resulting specimen is significantly brittle, and thus, it was impossible to prepare a glass fiber composite which can be used as a test specimen. However, in the case of an epoxy compound with a methoxysilyl group and allyl group together, brittleness of a cured product are improved, and thus, a measurable glass fiber composite may be prepared and a crack is not observed even in a surface of a cured product.

The invention claimed is:
1. An epoxy compound comprising:
a core, and the following groups directly bonded to the core:

i) at least two epoxy groups independently selected from epoxy groups of the following Formulae E1 and E2;

ii) at least one alkoxysilyl group selected from the group consisting of the following Formulae A1 to A5; and iii) at least one non-reactive silyl group, selected from the group consisting of the following Formulae A6 to A10, wherein the core is selected from the group consisting of the following Formulae AC to OC,

(AC)

(BC)

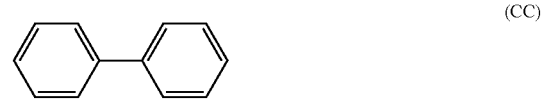

(CC)

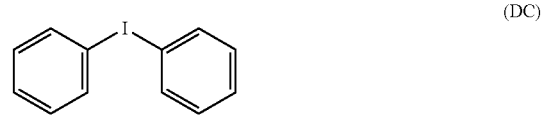

(DC)

-continued (EC)

(FC)

(GC)

(HC)

(IC)

(JC)

(KC)

(LC)

-continued $H_2N$—⟨⟩—M—⟨⟩—$NH_2$ (MC)

$H_2N$—CH₂—⟨⟩—CH₂—$NH_2$ and (NC)

$H_2N$—CH₂—⟨⟩—CH₂—$NH_2$ (OC)

in the above Formula DC, I is —$CH_2$—, —$C(CH_3)_2$—, —$C(CF_3)_2$—, —S—, —$SO_2$—, $$-\underset{\underset{CH_3}{|}}{\overset{\overset{CH_3}{|}}{C}}-⟨⟩-\underset{\underset{CH_3}{|}}{\overset{\overset{CH_3}{|}}{C}}- \text{ or}$$

and
in the above Formula HC, J is a direct linkage, —$CH_2$—, or wherein, Rx is H or a $C_1$-$C_3$ alkyl group,
in the above Formula IC, K is one of the following Formulae 1ac to 1fc, 1ac 1bc 1cc -continued

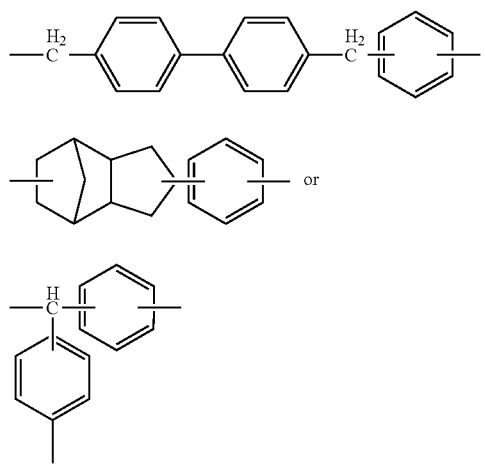

1dc

1ec

1fc in the above Formula LC, L is

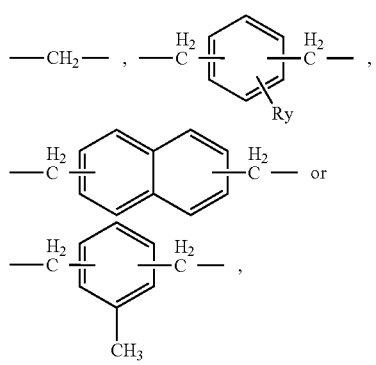

Ry is a linear or branched C1-C10 alkyl group, in the above Formula MC, M is —CH$_2$—, —C(CH$_3$)$_2$—, —C(CF$_3$)$_2$—, —S—, —SO$_2$—, or

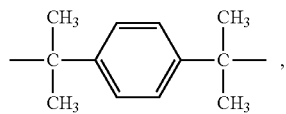

and R is H or C$_1$-C$_3$ alkyl, in the above Formula IC, when K is 1ac to 1ec, n is an integer of 3 or more, and when K is 1fc, n is an integer of 2 or more, in the above Formula JC, n is an integer of 2 or more, in the above Formula KC, n is an integer of 0 or more, in the above Formula LC, when L is

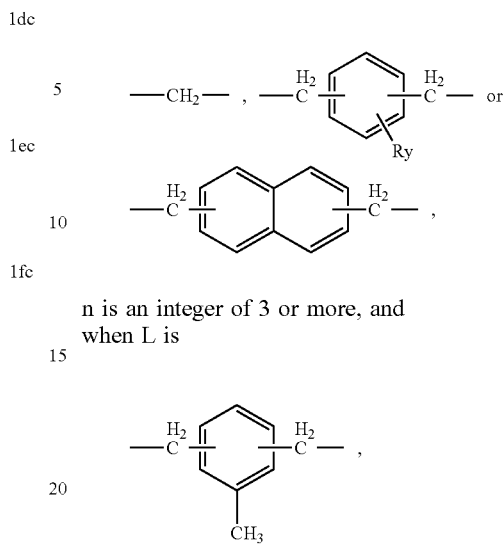

n is an integer of 3 or more, and when L is

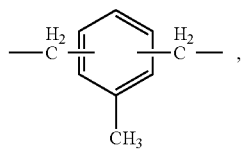

n is an integer of 2 or more,

| | |
|---|---|
| <image> | [Formula E1] |
| <image> | [Formula E2] |
| —CR$_b$R$_c$—CHR$_a$—CH$_2$—SiR$_1$R$_2$R$_3$ | [Formula A1] |
| —O—(CH$_2$)$_{m+2}$—SiR$_1$R$_2$R$_3$ | [Formula A2] |
| —O—CONH(CH$_2$)$_m$—SiR$_1$R$_2$R$_3$ | [Formula A3] |
| —(CH$_2$)$_{m+2}$—SiR$_1$R$_2$R$_3$ | [Formula A4] |
| —CONH(CH$_2$)$_m$—SiR$_1$R$_2$R$_3$ | [Formula A5] | in Formula A1, R$_a$, R$_b$ and R$_c$ are independently H or an alkyl group of 1 to 6 carbon atoms, and in Formulae A1 to A5, at least one of R$_1$ to R$_3$ is an alkoxy group of 1 to 6 carbon atoms, and the remainder are an alkyl group of 1 to 10 carbon atoms, wherein the alkyl group and the alkoxy group in the at least one of R$_1$ to R$_3$ are linear or branched, are cyclic or acyclic, and have or do not have an N, O, S, or P heteroatom, and m is an integer of 1 to 10,

| | |
|---|---|
| —CR$_b$R$_c$—CHR$_a$—CH$_2$—SiR$_4$R$_5$R$_6$ | [Formula A6] |
| —O—(CH$_2$)$_{m+2}$—SiR$_4$R$_5$R$_6$ | [Formula A7] |
| —O—CONH(CH$_2$)$_m$—SiR$_4$R$_5$R$_6$ | [Formula A8] |
| —(CH$_2$)$_{m+2}$—SiR$_4$R$_5$R$_6$ | [Formula A9] |
| —CONH(CH$_2$)$_m$—SiR$_4$R$_5$R$_6$ | [Formula A10] | in Formula A6, R$_a$, R$_b$ and R$_c$ are independently H or an alkyl group of 1 to 6 carbon atoms, and in the above Formulae A6 to A10, R$_4$ to R$_6$ are a non-reactive groups of the aliphatic, alicyclic, or aromatic moieties of 1 to 20 carbon atoms, wherein the non-reactive group are linear or branched, are cyclic or acyclic, and have or do not have an N, O, S, or P heteroatom, and m is an integer of 1 to 10.

2. The epoxy compound of claim 1, further comprising an alkenyl group selected from the group consisting of the following Formulae A11 and A12,

  [Formula A11]

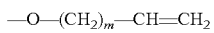  [Formula A12]

in Formula A11, $R_a$, $R_b$ and $R_c$ are independently H or an alkyl group of 1 to 6 carbon atoms, and m in Formulae A12 is an integer of 1 to 10.

3. The epoxy compound of claim 1, wherein the core is selected from the above Formulae AC to HC and MC to OC, the epoxy compound further comprises one or more additional cores of the same formula, and
wherein cores of Formulae AC to HC are connected by the following linking group LG1, and cores of Formulae MC to OC are connected by the following linking group LG2,

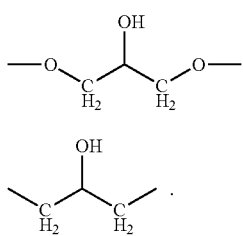

[Formula LG1]

[Formula LG2]

4. The epoxy compound of claim 1, wherein the epoxy compound is represented by any one of the following Formulae AF to OF,

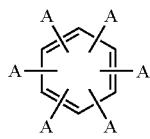
(AF)

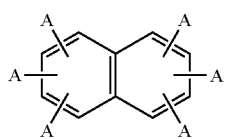
(BF)

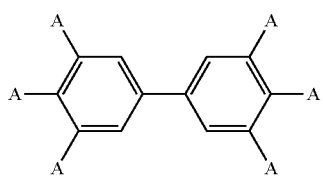
(CF)

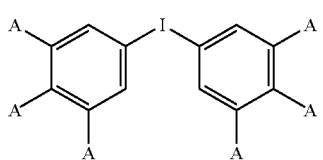
(DF)

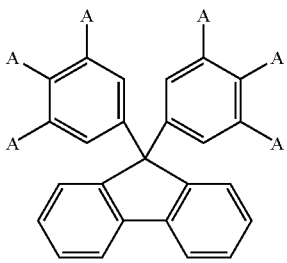
(EF)

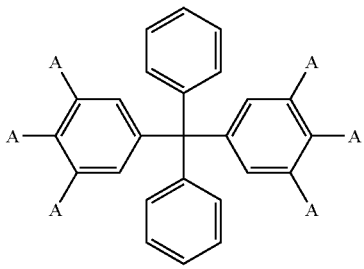
(FF)

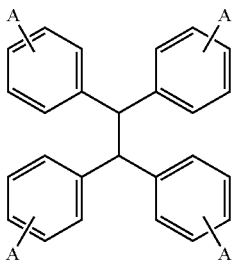
(GF)

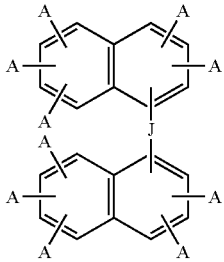
(HF)

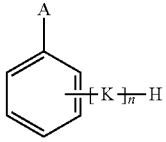
(IF)

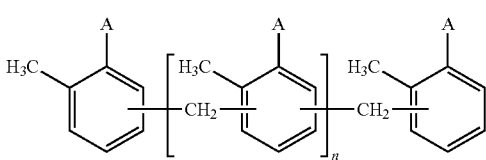
(JF)

-continued

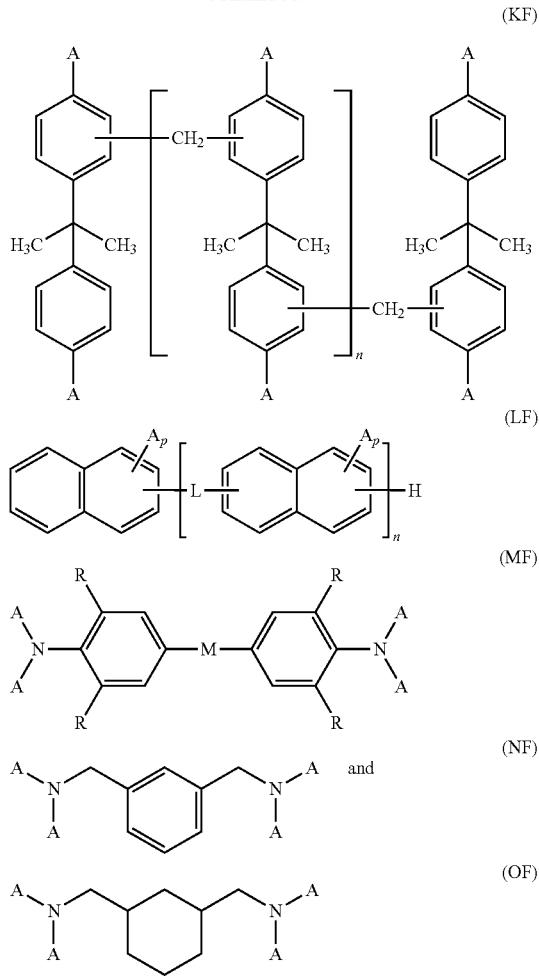

at least two of substituents A of the above Formulae AF to FF are independently selected from the following Formulae E1 and E2, at least one of substituents A thereof is selected from the group consisting of the following Formulae A1 to A3, at least one of the substituents A is independently selected from the group consisting of the following Formulae A6 to A8, and the remainder are independently selected from the group consisting of the following Formula A11, Formula A12, and hydrogen, two of substituents A of the above Formula GF are represented by the following Formula E1, one of substituents A thereof is represented by the following Formula A2 or Formula A3, and one of substituents A thereof is selected from the following Formulae A7 and A8, at least two of substituents A of the above Formulae HF to LF are represented by the following Formula E1, at least one of substituents A thereof is represented by the following Formula A2 or Formula A3, at least one of substituents A thereof is independently selected from the group consisting of the following Formulae A7 and A8, and the remainder thereof are independently selected from the group consisting of the following Formula A12, and hydrogen, two of substituents A of the above Formulae MF to OF are represented by the following Formula E2, one of substituents A thereof is selected from the following Formulae A4 and A5, and one of substituents A thereof is selected from the group consisting of the following Formulae A9 and A10, in the above Formula DF, I is $CH_2$—, —$C(CH_3)_2$—, —$C(CF_3)_2$—, —S—, —$SO_2$—,

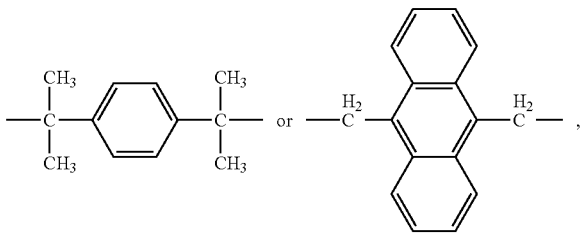

in the above Formula HF, J is a direct linkage, —$CH_2$— or

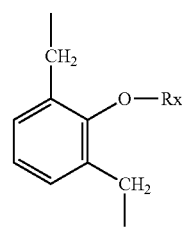

wherein, Rx is H or a $C_1$-$C_3$ alkyl group, in the above Formula IF, K is one of the following formulae 1A to 1F,

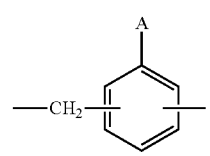

1A

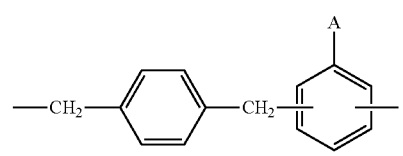

1B

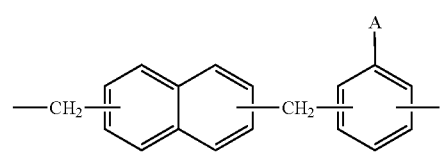

1C

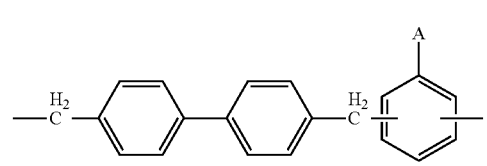

1D

-continued

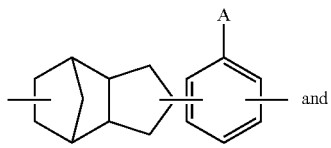
1E

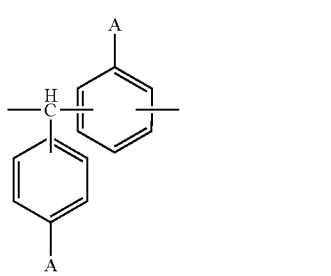
1F in the above Formula LF, L is

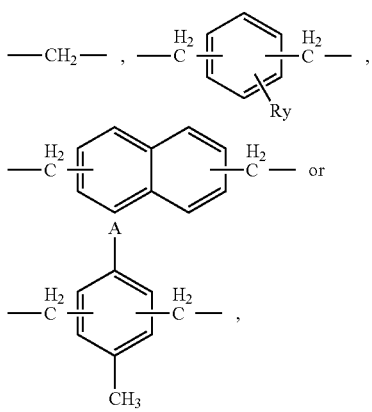

Ry is a linear or branched C1-C10 alkyl group, in the above Formula MF, M is —$CH_2$—, —$C(CH_3)_2$—, —$C(CF_3)_2$—, —S—, —$SO_2$—, or

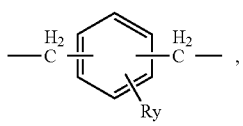

and R is H or $C_1$-$C_3$ alkyl, in the above Formula IF, when K is 1A to 1E, n is an integer of 3 or more, and when K is 1F, n is an integer of 2 or more, in the above Formula JF, n is an integer of 2 or more, in the above Formula KF, n is an integer of 0 or more, in the above Formula LF, when L is

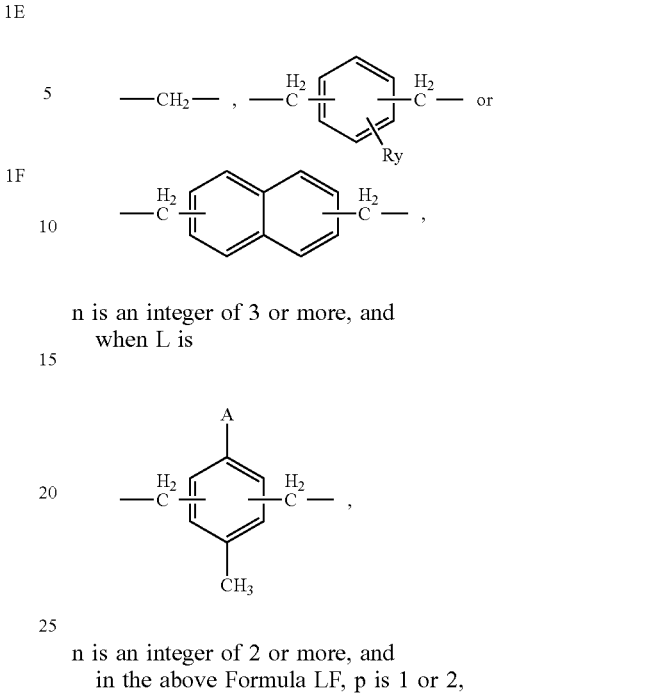

n is an integer of 3 or more, and when L is

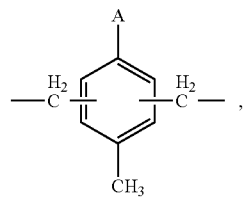

n is an integer of 2 or more, and in the above Formula LF, p is 1 or 2,

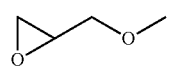     [Formula E1]

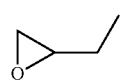     [Formula E2]

—$CR_bR_c$—$CHR_a$—$CH_2$—$SiR_1R_2R_3$    [Formula A1]

—O—$(CH_2)_{m+2}$—$SiR_1R_2R_3$    [Formula A2]

—O—$CONH(CH_2)_m$—$SiR_1R_2R_3$    [Formula A3]

—$(CH_2)_{m+2}$—$SiR_1R_2R_3$    [Formula A4]

—$CONH(CH_2)_m$—$SiR_1R_2R_3$    [Formula A5]

in Formula A1, $R_a$, $R_b$ and $R_c$ are independently H or an alkyl group of 1 to 6 carbon atoms, and in the above Formulae A1 to A5, at least one of $R_1$ to $R_3$ is an alkoxy group of 1 to 6 carbon atoms, and the remainder are alkyl groups of 1 to 10 carbon atoms, wherein the alkyl groups and the alkoxy group in the at least one of $R_1$ to $R_3$ are linear or branched, are cyclic or acyclic, and have or do not have an N, O, S, or P heteroatom, and m is an integer of 1 to 10, —$CR_bR_c$—$CHR_a$—$CH_2$—$SiR_4R_5R_6$    [Formula A6]

—O—$(CH_2)_{m+2}$—$SiR_4R_5R_6$    [Formula A7]

—O—$CONH(CH_2)_m$—$SiR_4R_5R_6$    [Formula A8]

—$(CH_2)_{m+2}$—$SiR_4R_5R_6$    [Formula A9]

—$CONH(CH_2)_m$—$SiR_4R_5R_6$    [Formula A10]

in the above Formula A6, $R_a$, $R_b$ and $R_c$ are independently H or an alkyl group of 1 to 6 carbon atoms, and in the above Formulae A6 to A10, $R_4$ to $R_6$ are non-reactive groups of the aliphatic, alicyclic, or aromatic moieties of 1 to 20 carbon atoms, wherein the non-reactive groups are linear or branched, are cyclic or acyclic, and have or do not have an N, O, S, or P heteroatom, and m is an integer of 1 to 10, —CR$_b$R$_c$—CR$_a$=CH$_2$     [Formula A11]

—O—(CH$_2$)$_m$—CH=CH$_2$     [Formula A12]

in Formula A11, R$_a$, R$_b$ and R$_c$ are independently H or an alkyl group of 1 to 6 carbon atoms, and in Formula A12, m is an integer of 1 to 10.

5. The epoxy compound of claim 1, wherein at least one of R$_1$ to R$_3$ in the at least one alkoxysilyl group represented by the above Formulae A1 to A5 is an alkoxy group of 2 to 4 carbon atoms.

6. The epoxy compound of claim 1, wherein R$_1$ to R$_3$ in the at least one alkoxysilyl group represented by the above Formulae A1 to A5 are all ethoxy groups.

7. The epoxy compound of claim 2, wherein all of R$_1$ to R$_3$ in the at least one alkoxysilyl group represented by the above Formulae A1 to A5 are methoxy groups.

8. A mixture of an epoxy compound, comprising the epoxy compound of claim 1,
wherein a ratio of the at least one alkoxysilyl group to the at least one non-reactive silyl group is within a range of 1:99 to 99:1.

9. An epoxy composition comprising the epoxy mixture of claim 8.

10. The epoxy composition of claim 9, further comprising at least one type of filler selected from the group consisting of inorganic particles or fiber.

11. An epoxy composition comprising the epoxy compound of claim 1.

12. The epoxy composition of claim 11, further comprising at least one type of filler selected from the group consisting of inorganic particles or fiber.

13. A cured product of the epoxy composition of claim 11.

14. The cured product of claim 13, having a coefficient of thermal expansion of 60 ppm/° C. or lower.

15. The cured product of claim 13, having a glass transition temperature higher than 100° C. or not exhibiting a glass transition temperature.

16. A method of producing an epoxy compound of any one of the following Formulae AF to OF, comprising the reaction of a starting material of any one of the following Formulae AS1 to OS1, alkoxysilane of the following Formula AS5, and non-reactive silane of the following Formula AS6, in the presence of a platinum catalyst and an optional solvent, HSiR$_1$R$_2$R$_3$     [Formula AS5]

in the above Formula AS5, at least one of R$_1$ to R$_3$ is a C1-C6 alkoxy group, and the remainder thereof are C1-C10 alkyl groups, wherein the alkoxy group and the alkyl groups in the at least one of R$_1$ to R$_3$ are linear or branched, are cyclic or acyclic, and have or do not have an N, O, S, or P heteroatom, HSiR$_4$R$_5$R$_6$     [Formula AS6]

in the above Formula AS6, R$_4$ to R$_6$ are non-reactive groups of the aliphatic, alicyclic, or aromatic moieties of 1 to 20 carbon atoms, wherein the non-reactive groups are linear or branched, are cyclic or acyclic, and have or do not have an N, O, S, or P heteroatom,

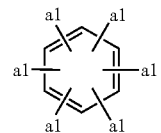
(AS1)

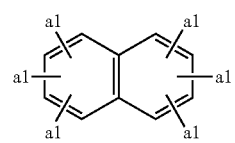
(BS1)

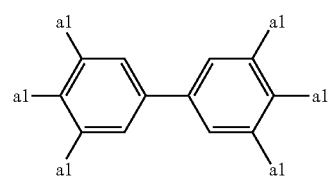
(CS1)

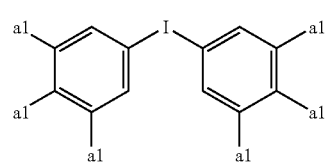
(DS1)

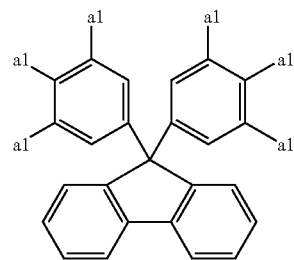
(ES1)

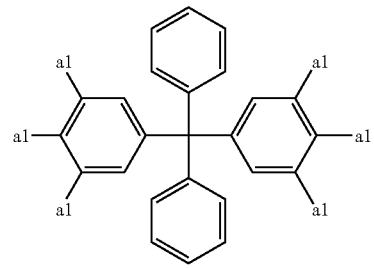
(FS1)

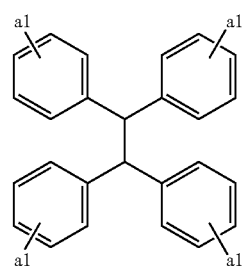
(GS1)

-continued (HS1) 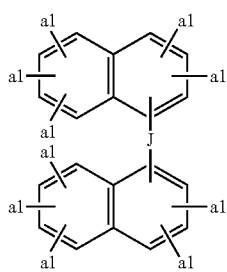

(IS1) 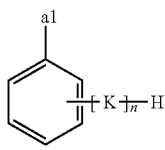

(JS1) 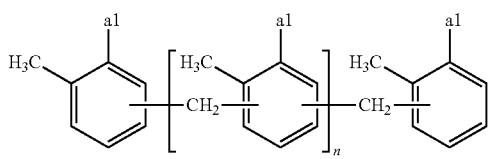

(KS1) 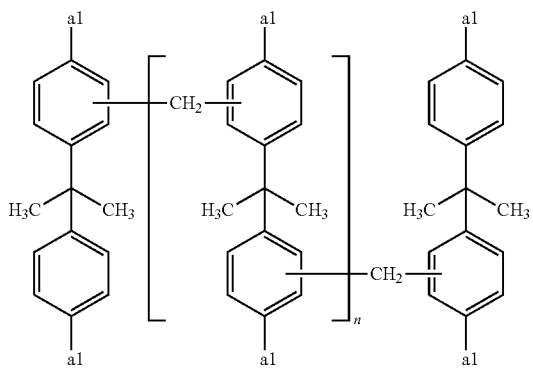

(LS1) 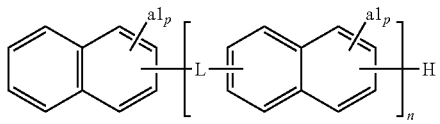

(MS1) 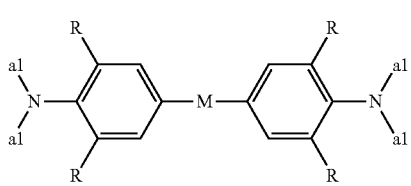

(NS1) 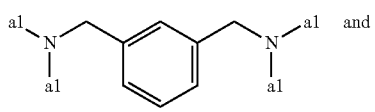

(OS1) 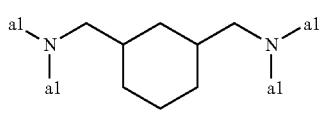

at least two of a plurality of substituents a1 of the above Formulae AS1 to FS1 are represented by the following Formula E1 or E2, at least two of the plurality of substituents a1 are represented by the following Formula A11 or A12, and the remainder thereof are hydrogen, two of substituents a1 of the above Formula GS1 are represented by the following Formula E1, and two of the substituents a1 are represented by the following Formula A12, at least two of substituents a1 of the above Formulae HS1 to LS1 are represented by the following Formula E1, at least two of the substituents a1 are represented by the following Formula A12, and the remainder thereof are hydrogen, two of substituents a1 of the above Formulae MS1 to OS1 are represented by the following Formula E2, and the remainder thereof are represented by the following Formula A13, and in the above Formula DS1, I is —CH$_2$—, —C(CH$_3$)$_2$—, —C(CF$_3$)$_2$—, —S—, —SO$_2$—,

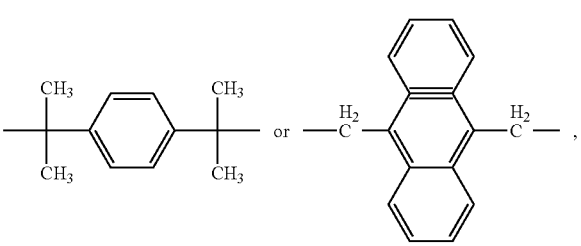

in the above Formula HS1, J is a direct linkage, —CH$_2$— or

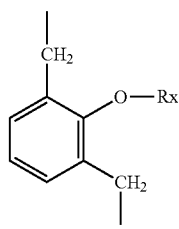

(Rx is H or a C$_1$-C$_3$ alkyl group), in the above Formula IS1, K is one of the following Formulae 1a1 to 1f1, 1a1

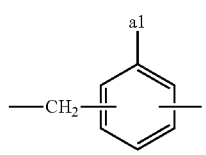

1b1

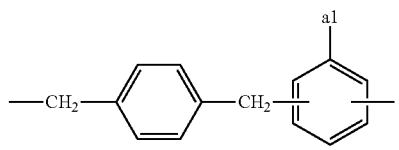

-continued

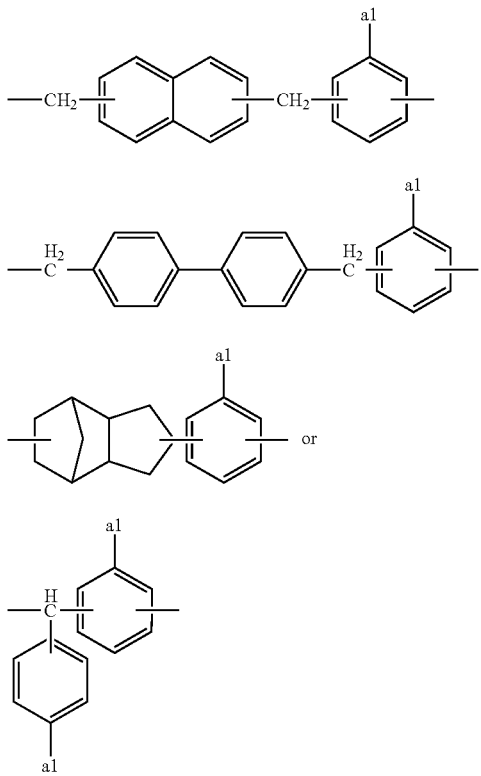

in the above Formula LS1, L is

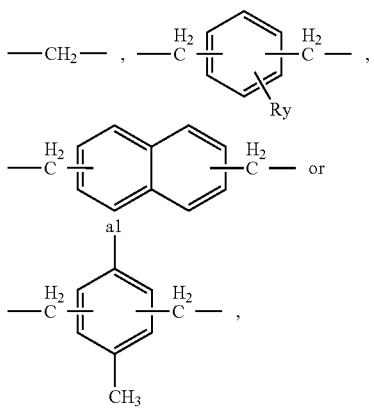

Ry is a linear or branched C1-C10 alkyl group, in the above Formula MS1, M is —CH$_2$—, —C(CH$_3$)$_2$—, —C(CF$_3$)$_2$—, —S—, —SO$_2$—, or

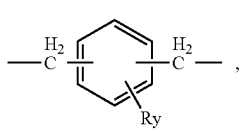

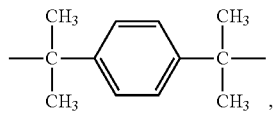

and R is H or C$_1$-C$_3$ alkyl, in the above Formula IS1, when K is 1a1 to 1e1, n is an integer of 3 or more, and when K is 1f1, n is an integer of 2 or more, in the above Formula JS1, n is an integer of 2 or more, in the above Formula KS1, n is an integer of 0 or more, in the above Formula LS1, when L is

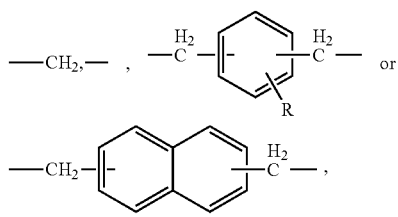

n is an integer of 3 or more, and when L is

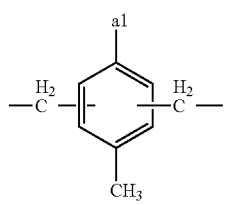

n is an integer of 2 or more, and in the above Formula LS1, p is 1 or 2,

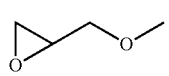     [Formula E1]

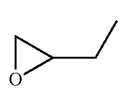     [Formula E2]

—CR$_b$R$_c$—CR$_a$=CH$_2$     [Formula A11]

—O—(CH$_2$)$_m$—CH=CH$_2$     [Formula A12]

—(CH$_2$)$_m$—CH=CH$_2$     [Formula A13]

in Formula A11, R$_a$, R$_b$ and R$_c$ are independently H or an alkyl group of 1 to 6 carbon atoms, and in Formulae A12 and A13, m is an integer of 1 to 10, (AF)

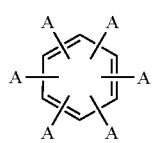

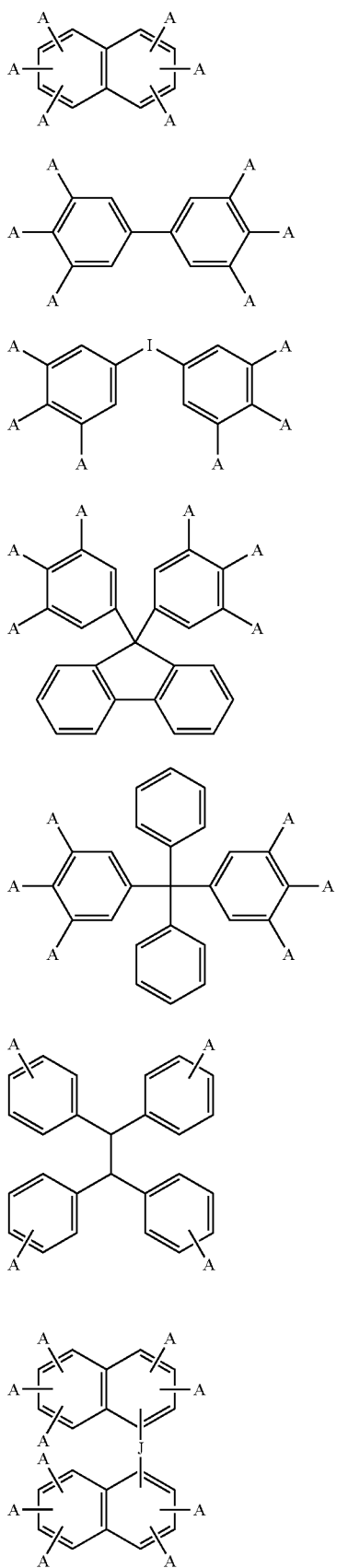

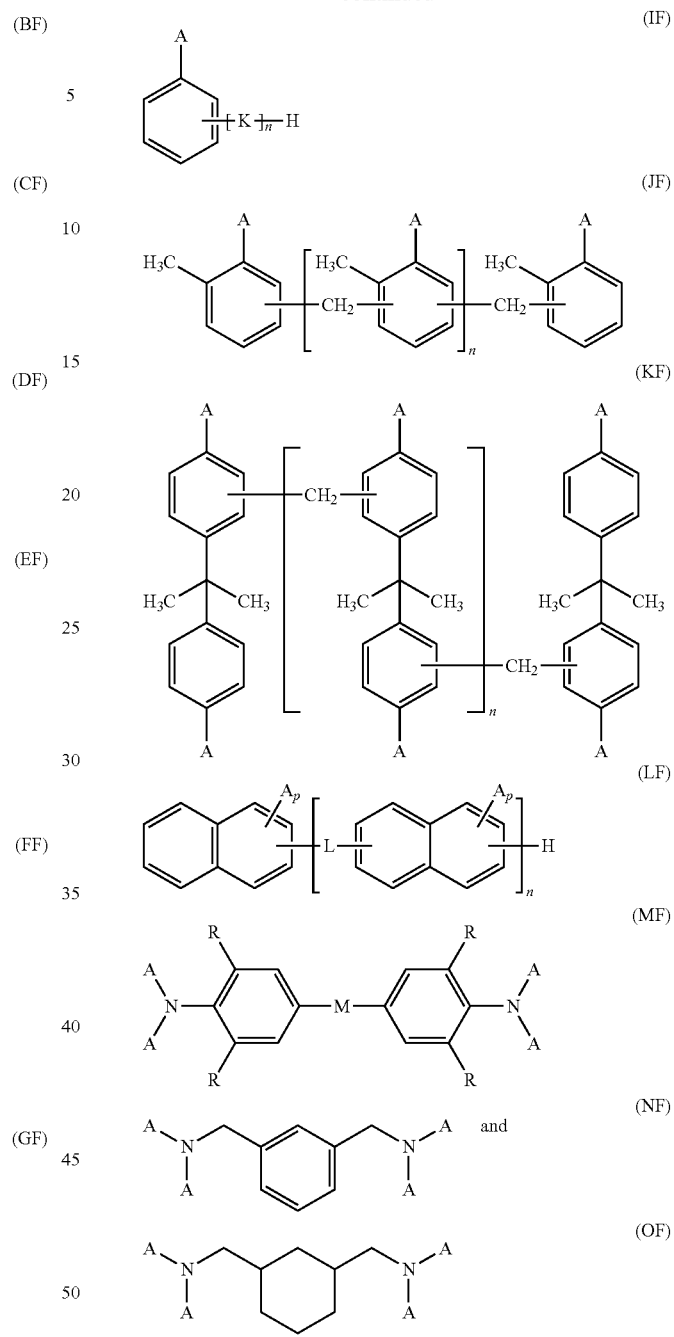

at least two of substituents A of the above Formulae AF to FF are represented by the above Formula E1 or E2, at least one of substituents A thereof is selected from the group consisting of the following Formulae A1 and A2, at least one of substituent A thereof is independently selected from the group consisting of the following Formulae A6 and A7, and the remainder thereof are independently selected from the group consisting of the following Formulae A11, A12 and hydrogen, two of substituents A of the above Formula GF are represented by the following Formula E1, one of substituents A thereof is represented by the following Formula A2, and one of substituents A thereof is represented by the following Formula A7, at least two of substituents A of the above Formulae HF to LF are represented by the following Formula E1, at least one of substituents A thereof is represented by the following Formula A2, at least one of substituents A thereof is represented by the following Formula A7, and the remainder thereof are independently selected from the group consisting of the following Formula A12, and hydrogen, two of substituents A of the above Formulae MF to OF are represented by the following Formula E2, one of substituents A thereof is represented by the following Formula A4, and one of substituents A thereof is represented by the following Formula A9, in the above Formula DF, I is —CH$_2$—, —C(CH$_3$)$_2$—, —C(CF$_3$)$_2$—, —S—, —SO$_2$—,

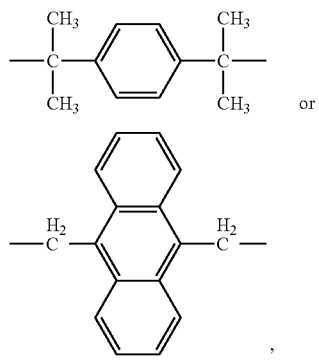
or

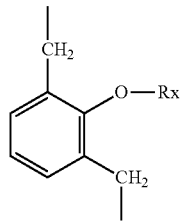
, in the above Formula HF, J is a direct linkage, —CH$_2$— or

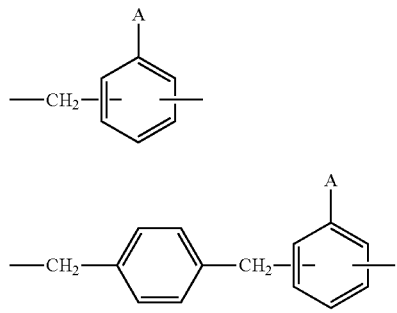

(Rx is H or a C$_1$-C$_3$ alkyl group), in the above Formula IF, K is one of the following formulae 1A to 1F,

1A

—CH$_2$—⟨A-phenyl⟩—

1B

—CH$_2$—⟨phenyl⟩—CH$_2$—⟨A-phenyl⟩—

1C

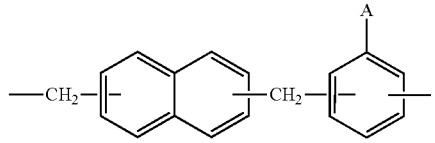

1D

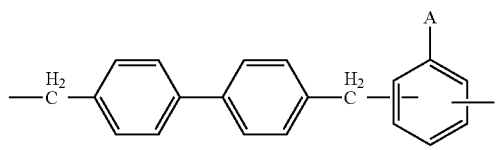

1E

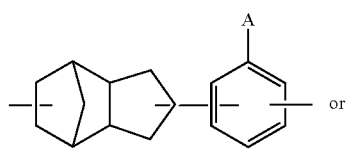
or

1F

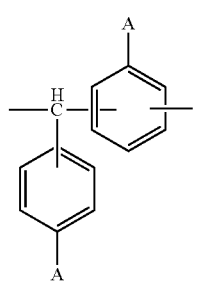

in the above Formula LF, L is

—CH$_2$—,

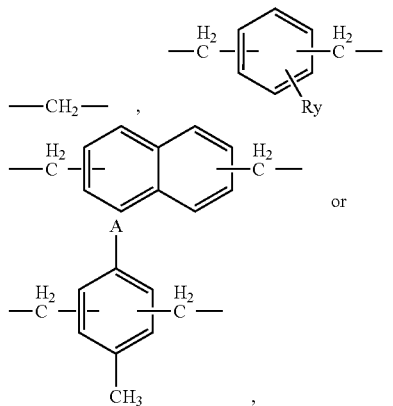

Ry is a linear or branched C1-C10 alkyl group, in the above Formula MF, M is —CH$_2$—, —C(CH$_3$)$_2$—, —C(CF$_3$)$_2$—, —S—, —SO$_2$—, or

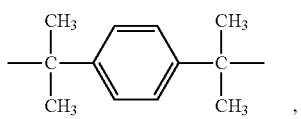

and R is H or $C_1$-$C_3$ alkyl, in the above Formula IF, when K is 1A to 1E, n is an integer of 3 or more, and when K is 1F, n is an integer of 2 or more, in the above Formula JF, n is an integer of 2 or more, in the above Formula KF, n is an integer of 0 or more, in the above Formula LF, when L is

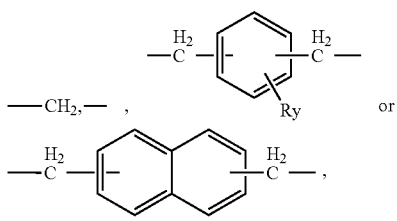

n is an integer of 3 or more, and
when L is

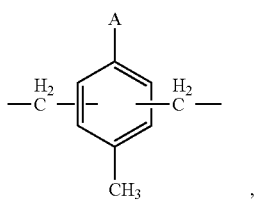

n is an integer of 2 or more, and
in the above Formula LF, p is 1 or 2,

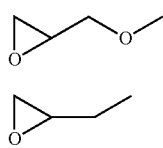 [Formula E1]

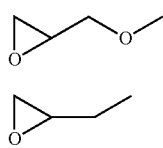 [Formula E2]

—$CR_bR_c$—$CHR_a$—$CH_2$—$SiR_1R_2R_3$ [Formula A1]

—O—$(CH_2)_{m+2}$—$SiR_1R_2R_3$ [Formula A2]

—$(CH_2)_{m+2}$—$SiR_1R_2R_3$ [Formula A4]

in Formula A1, $R_a$, $R_b$ and $R_c$ are independently H or an alkyl group of 1 to 6 carbon atoms, and in the above Formulae A1, A2, and A4, at least one of $R_1$ to $R_3$ is an alkoxy group of 1 to 6 carbon atoms, and the remainder are alkyl groups having 1 to 10 carbon atoms, wherein the alkyl groups and the alkoxy group in the at least one of $R_1$ to $R_3$ are linear or branched, are cyclic or acyclic, and have or do not have an N, O, S, or P heteroatom, and m is an integer of 1 to 10, —$CR_bR_c$—$CHR_a$—$CH_2$—$SiR_4R_5R_6$ [Formula A6]

—O—$(CH_2)_{m+2}$—$SiR_4R_5R_6$ [Formula A7]

—$(CH_2)_{m+2}$—$SiR_4R_5R_6$ [Formula A9]

in the above Formula A6, $R_a$, $R_b$ and $R_c$ are independently H or an alkyl group of 1 to 6 carbon atoms, and in the above Formulae A6, A7 and A9, $R_4$ to $R_6$ are non-reactive groups of the aliphatic, alicyclic, or aromatic moieties of 1 to 20 carbon atoms, wherein the non-reactive groups are linear or branched, are cyclic or acyclic, and have or do not have an N, O, S, or P heteroatom, and m is an integer of 1 to 10, —$CR_bR_c$—$CR_a$=$CH_2$ [Formula A11]

—O—$(CH_2)_m$—CH=$CH_2$ [Formula A12]

in Formula A11, $R_a$, $R_b$ and $R_c$ are independently H or an alkyl group of 1 to 6 carbon atoms, and in Formula A12, m is an integer of 1 to 10.

17. A method of producing an epoxy compound of any one of the following Formulae AF to OF, comprising:

reaction of a starting material of any one of the above Formulae AS2 to OS2, alkoxysilane of the following Formula AS3, and non-reactive silane of the following Formula AS4, in the presence of an optional solvent, OCN—$(CH_2)_m$—$SiR_1R_2R_3$ [Formula AS3]

in the above Formula AS3, at least one of $R_1$ to $R_3$ is a C1-C6 alkoxy group, and the remainder thereof are C1-C10 alkyl groups, wherein the alkoxy group and the alkyl groups in the at least one of $R_1$ to $R_3$ are linear or branched, are cyclic or acyclic, and have or do not have an N, O, S, or P heteroatom, and m is an integer of 1 to 10, OCN—$(CH_2)_m$—$SiR_4R_5R_6$ [Formula AS4]

in the above Formula AS4, $R_4$ to $R_6$ are non-reactive groups of the aliphatic, alicyclic, or aromatic moieties of 1 to 20 carbon atoms, wherein the non-reactive groups are linear or branched, are cyclic or acyclic, and have or do not have an N, O, S, or P heteroatom, and m is an integer of 1 to 10,

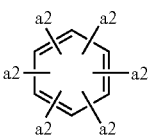 (AS2)

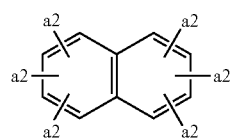 (BS2)

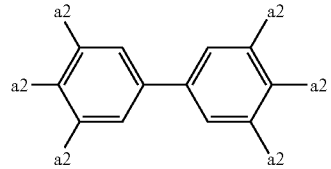 (CS2)

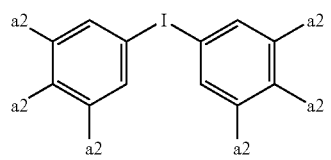 (DS2)

-continued (ES2)
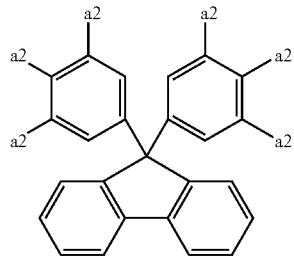

(FS2)
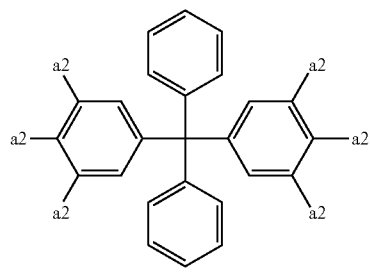

(GS2)
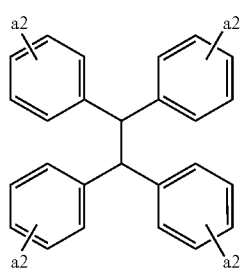

(HS2)
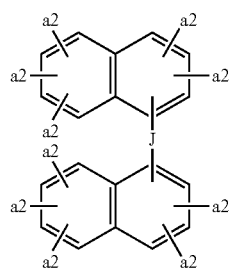

(IS2)
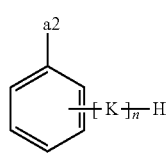

(JS2)
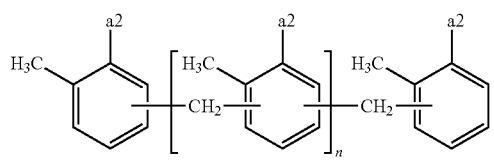

-continued (KS2)
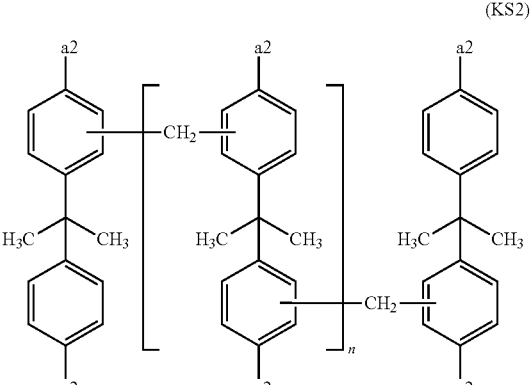

(LS2)
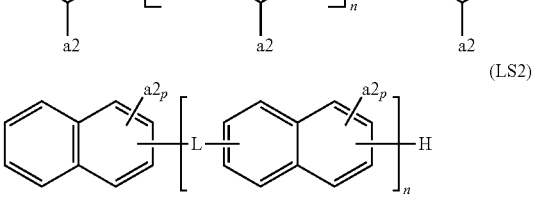

(MS2)
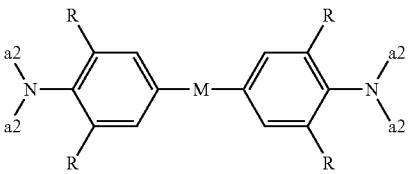

(NS2)
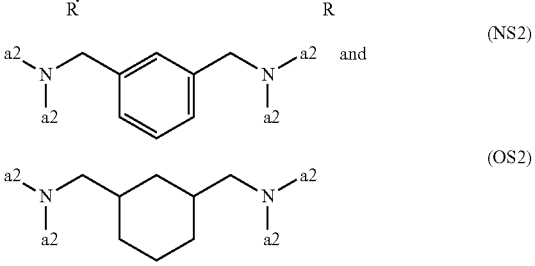

(OS2)
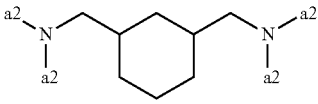

at least two of substituents a2 of the above Formulae AS2 to FS2 are represented by the following Formula E2, at least two of the substituents a2 are hydroxy groups, and the remainder thereof are independently selected from the group consisting of hydrogen and the following Formula A11, two of substituents a2 of the above Formulae GS2 are represented by the following Formula E1, and two of the substituents a2 are hydroxy groups, at least two of substituents a2 of the above Formulae HS2 to LS2 are represented by the following Formula E1, at least two of the substituents a2 are hydroxy groups, and the remainder thereof are hydrogen, two of substituents a2 of the above Formulae MS2 to OS2 are represented by the above Formula E2, and the remainder thereof are hydrogen, and in the above Formula DS2, I is —CH$_2$—, —C(CH$_3$)$_2$—, —C(CF$_3$)$_2$—, —S—, —SO$_2$,

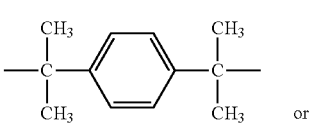 or

-continued

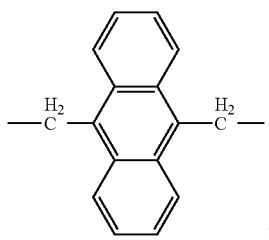

in the above Formula HS2, J is a direct linkage, —CH$_2$— or

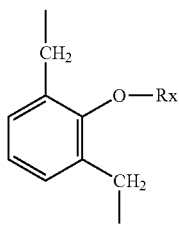

(Rx is H or a C$_1$-C$_3$ alkyl group), in the above Formula IS2, K is one of the following Formulae 1a2 to 1f2, 1a2
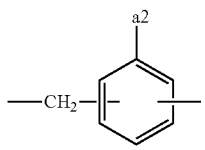

1b2
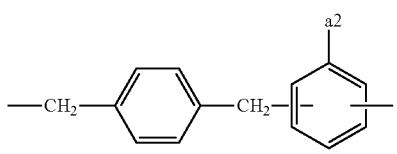

1c2
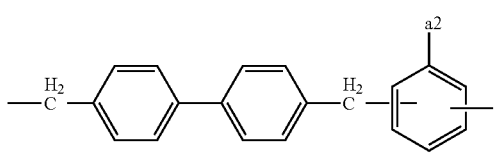

1d2
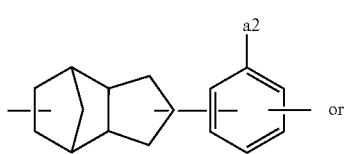

1e2

-continued

1f2
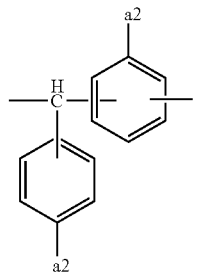

in the above Formula LS2, L is

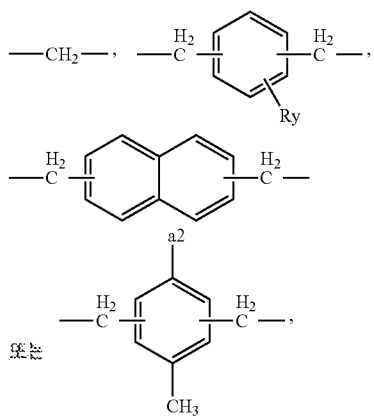

and, in

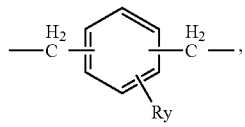

Ry is a linear or branched C1-C10 alkyl group, in the above Formula MS2, M is —CH$_2$—, —C(CH$_3$)$_2$—, —C(CF$_3$)$_2$—, —S—, —SO$_2$—, or

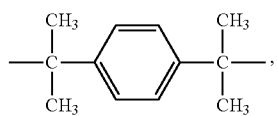

and R is H or C$_1$-C$_3$ alkyl, in the above Formula IS2, when K is 2a to 2e, n is an integer of 3 or more, and when K is 2f, n is an integer of 2 or more,
in the above Formula JS2, n is an integer of 2 or more,
in the above Formula KS2, n is an integer of 0 or more,
in the above Formula LS2, when L is

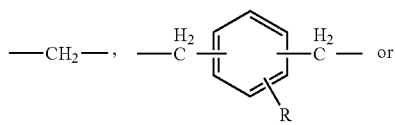

-continued
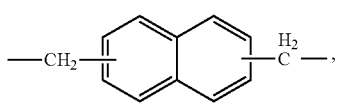
n is an integer of 3 or more, and when L is
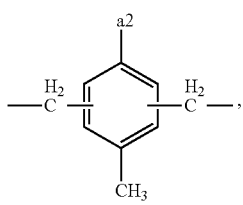
n is an integer of 2 or more, and
in the above Formula LS2, p is 1 or 2,
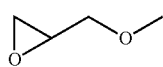 [Formula E1]
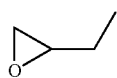 [Formula E2]
—CR$_b$R$_c$—CR$_a$=CH$_2$ [Formula A11]
in Formula A11, R$_a$, R$_b$ and R$_c$ are independently H or an alkyl group of 1 to 6 carbon atoms,
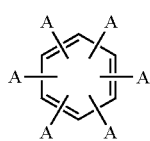 (AF)
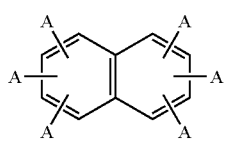 (BF)
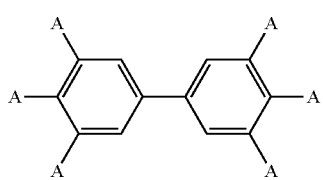 (CF)
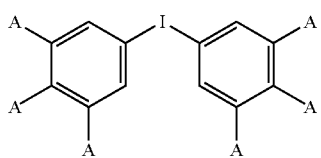 (DF)
-continued
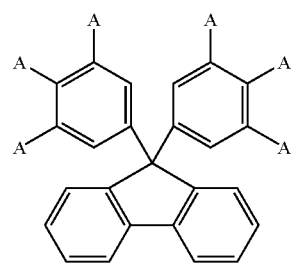 (EF)
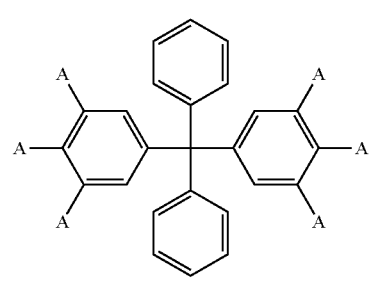 (FF)
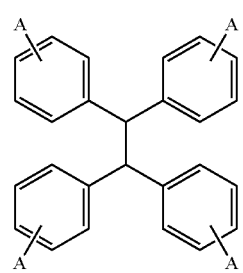 (GF)
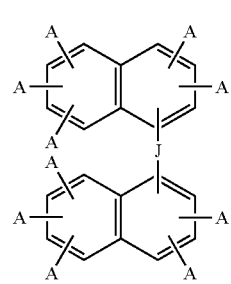 (HF)
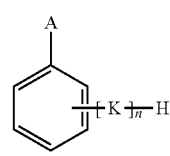 (IF)
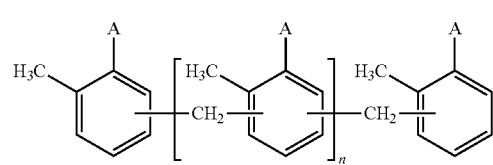 (JF)

-continued

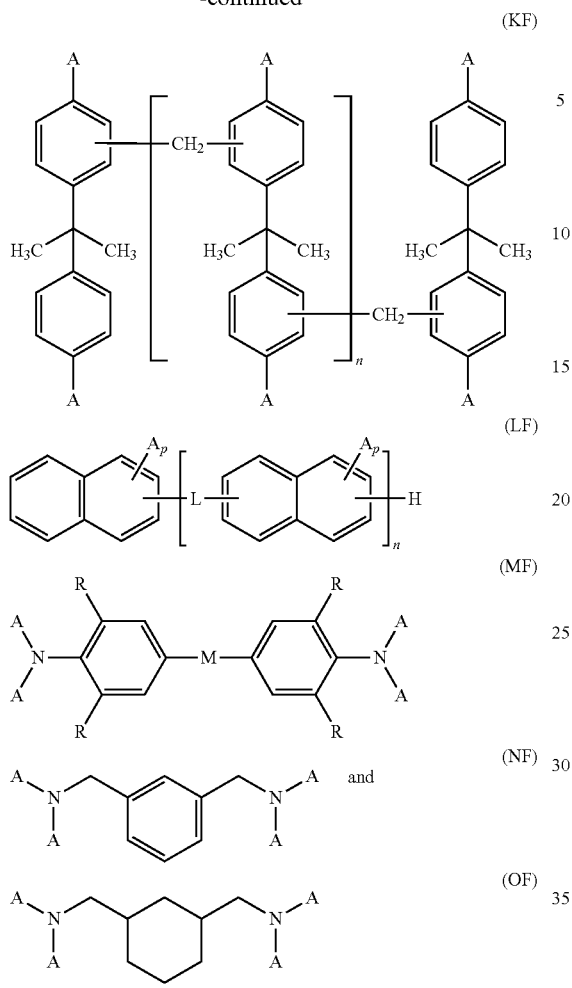

(KF)

(LF)

(MF)

(NF)

(OF)

at least two of substituents A of the above Formulae AF to FF are represented by the following Formula E2, at least one of substituents A thereof is represented by the following Formula A3, at least one of substituents A thereof is represented by the following Formula A8, and the remainder thereof are independently selected from the following Formula A11, and hydrogen, two of substituents A of the above Formula GF are represented by the following Formula E1, one of substituent A thereof is represented by the following Formula A3, and one of substituent A thereof is represented by the following Formula A8, at least two of substituents A of the above Formulae HF to LF are represented by the following Formula E1, at least one of substituent A thereof is represented by the following Formula A3, at least one of substituent A thereof is represented by the following Formula A8, and the remainder thereof are hydrogen, two of substituents A of the above Formulae MF to OF are represented by the following Formula E2, one of substituent A thereof is represented by the following Formula A5, and one of substituent A thereof is represented by the following Formula A10, in the above Formula DF, I is —CH$_2$—, —C(CH$_3$)$_2$—, —C(CF$_3$)$_2$—, —S—, —SO$_2$—,

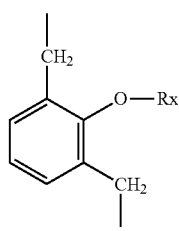

in the above Formula HF, J is a direct linkage, —CH$_2$— or

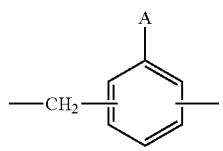

(Rx is H or a C$_1$-C$_3$ alkyl group),
in the above Formula IF, K is one of the following formulae 1A to 1F,

1A

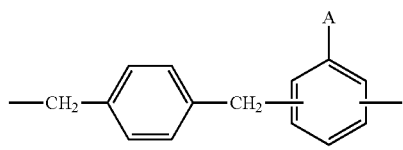

1B

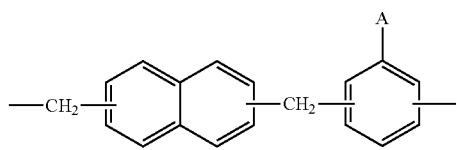

1C

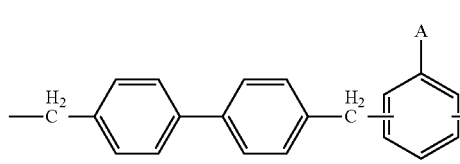

1D

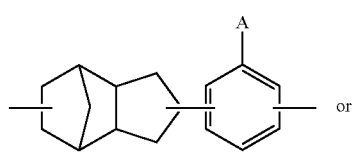

1E or

-continued

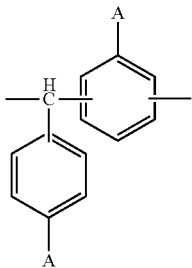

in the above Formula LF, L is

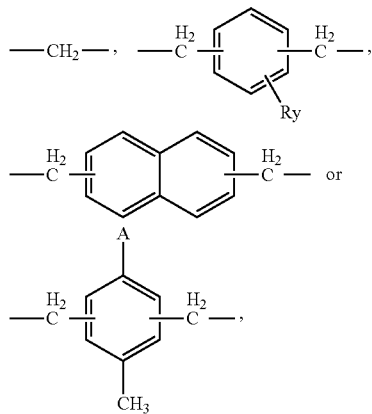

and in

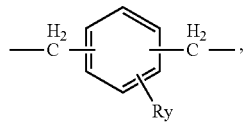

Ry is a linear or branched C1-C10 alkyl group,
in the above Formula MF, M is —CH$_2$—, —C(CH$_3$)$_2$—, —C(CF$_3$)$_2$—, —S—, —SO$_2$—, or

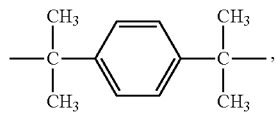

and R is H or C$_1$-C$_3$ alkyl,
in the above Formula IF, when K is 1A to 1E, n is an integer of 3 or more, and when K is 1F, n is an integer of 2 or more,
in the above Formula JF, n is an integer of 2 or more,
in the above Formula KF, n is an integer of 0 or more,
in the above Formula LF, when L is

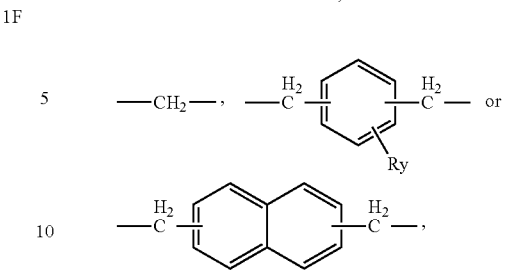

n is an integer of 3 or more, and when L is

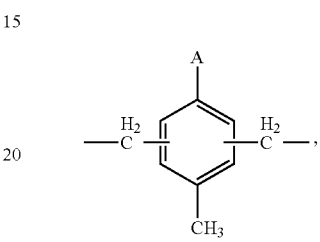

n is an integer of 2 or more, and
in the above Formula LF, p is 1 or 2,

—O—CONH(CH$_2$)$_m$—SiR$_1$R$_2$R$_3$     [Formula A3]

—CONH(CH$_2$)$_m$—SiR$_1$R$_2$R$_3$     [Formula A5]

in the above Formulae A3 and A5, at least one of R$_1$ to R$_3$ is an alkoxy group of 1 to 6 carbon atoms, and the remainder thereof are alkyl groups having 1 to 10 carbon atoms, wherein the alkyl groups and the alkoxy group in the at least one of R$_1$ to R$_3$ are linear or branched, are cyclic or acyclic, and have or do not have an N, O, S, or P heteroatom, and m is an integer of 1 to 10, —O—CONH(CH$_2$)$_m$—SiR$_4$R$_5$R$_6$     [Formula A8]

—CONH(CH$_2$)$_m$—SiR$_4$R$_5$R$_6$     [Formula A10]

in the above Formulae A8 and A10, R$_4$ to R$_6$ are non-reactive groups of the aliphatic, alicyclic, or aromatic moieties of 1 to 20 carbon atoms, wherein the non-reactive groups are linear or branched, are cyclic or acyclic, and have or do not have an N, O, S, or P heteroatom, and m is an integer of 1 to 10, —CR$_b$R$_c$—CR$_a$=CH$_2$     [Formula A11]

in Formula A11, R$_a$, R$_b$ and R$_c$ are independently H or an alkyl group of 1 to 6 carbon atoms.

* * * * *